(12) United States Patent
Hyoue et al.

(10) Patent No.: US 9,044,177 B2
(45) Date of Patent: Jun. 2, 2015

(54) LANCET PRICKING DEVICE

(75) Inventors: Tomoyuki Hyoue, Maniwa (JP); Hideaki Saeki, Maniwa (JP); Hirokazu Imori, Maniwa (JP)

(73) Assignees: ASAHI POLYSLIDER COMPANY, LIMITED, Osaka (JP); IZUMI-COSMO COMPANY, LIMITED, Osaka (JP)

( * ) Notice: Subject to any disclaimer, the term of this patent is extended or adjusted under 35 U.S.C. 154(b) by 233 days.

(21) Appl. No.: 13/500,127

(22) PCT Filed: Oct. 6, 2010

(86) PCT No.: PCT/JP2010/067529
§ 371 (c)(1),
(2), (4) Date: May 9, 2012

(87) PCT Pub. No.: WO2011/043368
PCT Pub. Date: Apr. 14, 2011

(65) Prior Publication Data
US 2012/0215246 A1    Aug. 23, 2012

(30) Foreign Application Priority Data

Oct. 7, 2009  (JP) ............................. P2009-233428
Oct. 20, 2009 (JP) ............................. P2009-241385

(51) Int. Cl.
*A61B 17/32* (2006.01)
*A61B 17/34* (2006.01)
(Continued)

(52) U.S. Cl.
CPC ......... *A61B 5/1411* (2013.01); *A61B 5/150022* (2013.01); *A61B 5/15019* (2013.01);
(Continued)

(58) Field of Classification Search
USPC .................................. 606/181, 182; 600/583
See application file for complete search history.

(56) References Cited

U.S. PATENT DOCUMENTS

| 1,275,318 A | 8/1918 | Stevens |
| 2,737,666 A | 3/1956 | Herider et al. |

(Continued)

FOREIGN PATENT DOCUMENTS

| EP | 0 264 276 | 4/1988 |
| EP | 1 493 937 | 1/2005 |

(Continued)

OTHER PUBLICATIONS

Supplementary European Search Report issued Jan. 21, 2013 in European Patent Application No. EP 10 82 2038.
(Continued)

*Primary Examiner* — Gregory Anderson
*Assistant Examiner* — Christopher L Templeton
(74) *Attorney, Agent, or Firm* — Wenderoth, Lind & Ponack, L.L.P.

(57) ABSTRACT

A lancet pricking device comprises a lancet, a launching spring, a trigger part and a holder housing the lancet, launching spring and trigger part. The lancet comprises a lancet body, lancet cap and pricking needle. The pricking needle is in both the lancet body and lancet cap. The trigger part has a pair of arms positioned inside the holder. The launching spring is attached to the lancet body. The lancet body is secured to the arms of the trigger part by an abutment of the lancet body on the arms such that the launching spring is compressed before a pricking operation. The trigger part cannot be pushed toward the inside of the holder before the lancet cap is removed, but can be pushed toward the inside of the holder after the cap is removed. The lancet body warps when pressed to release the secured lancet body.

11 Claims, 55 Drawing Sheets

(51) Int. Cl.
*A61B 5/15* (2006.01)
*A61B 5/151* (2006.01)
*F16F 1/12* (2006.01)

(52) U.S. Cl.
CPC ..... *A61B5/150259* (2013.01); *A61B 5/150435* (2013.01); *A61B 5/150519* (2013.01); *A61B 5/150549* (2013.01); *A61B 5/150618* (2013.01); *A61B 5/150916* (2013.01); *A61B 5/15111* (2013.01); *A61B 5/15113* (2013.01); *A61B 5/15117* (2013.01); *A61B 5/15142* (2013.01); *A61B 5/1405* (2013.01); *F16F 1/122* (2013.01); *F16F 1/123* (2013.01); *A61B 5/151* (2013.01); *A61B 5/15107* (2013.01); *A61B 5/15144* (2013.01)

(56) References Cited

U.S. PATENT DOCUMENTS

| | | | |
|---|---|---|---|
| 4,371,154 A | 2/1983 | Winbigler | |
| 4,388,925 A * | 6/1983 | Burns | 606/182 |
| 4,521,005 A | 6/1985 | Calderoni | |
| 4,535,769 A * | 8/1985 | Burns | 606/182 |
| 4,653,513 A * | 3/1987 | Dombrowski | 600/578 |
| 5,147,375 A * | 9/1992 | Sullivan et al. | 606/182 |
| 5,350,392 A * | 9/1994 | Purcell et al. | 606/182 |
| 5,385,571 A | 1/1995 | Morita | |
| 5,540,709 A * | 7/1996 | Ramel | 606/183 |
| 5,707,384 A * | 1/1998 | Kim | 606/181 |
| 6,258,112 B1 * | 7/2001 | Schraga | 606/181 |
| 6,432,120 B1 | 8/2002 | Teo | 606/182 |
| 6,852,119 B1 * | 2/2005 | Abulhaj et al. | 606/182 |
| 7,175,643 B2 * | 2/2007 | Shi | 606/181 |
| 7,775,991 B2 * | 8/2010 | Feaster et al. | 600/584 |
| 8,109,959 B2 * | 2/2012 | Chang et al. | 606/181 |
| 8,172,867 B2 * | 5/2012 | Nicholls | 606/182 |
| 2002/0087180 A1 * | 7/2002 | Searle et al. | 606/181 |
| 2003/0216767 A1 | 11/2003 | List et al. | |
| 2004/0193201 A1 * | 9/2004 | Kim | 606/181 |
| 2005/0017422 A1 | 1/2005 | Wakamori et al. | |
| 2005/0085840 A1 * | 4/2005 | Yi et al. | 606/182 |
| 2005/0143771 A1 | 6/2005 | Stout et al. | |
| 2005/0234487 A1 * | 10/2005 | Shi | 606/181 |
| 2006/0052809 A1 | 3/2006 | Karbowniczek et al. | |
| 2006/0116705 A1 * | 6/2006 | Schraga | 606/181 |
| 2007/0049959 A1 | 3/2007 | Feaster et al. | |
| 2007/0162065 A1 * | 7/2007 | Li et al. | 606/182 |
| 2008/0039886 A1 * | 2/2008 | Shi | 606/182 |
| 2008/0188882 A1 * | 8/2008 | Dicesare et al. | 606/182 |
| 2008/0195132 A1 * | 8/2008 | Schraga | 606/182 |
| 2008/0319469 A1 * | 12/2008 | D'Agostino | 606/182 |
| 2009/0069832 A1 | 3/2009 | Kitamura et al. | |
| 2009/0275969 A1 | 11/2009 | Kitamura et al. | |
| 2009/0299397 A1 * | 12/2009 | Ruan et al. | 606/182 |

FOREIGN PATENT DOCUMENTS

| | | |
|---|---|---|
| EP | 2 033 577 | 3/2009 |
| WO | 2007/018215 | 2/2007 |
| WO | 2007/123509 | 11/2007 |
| WO | 2008/009985 | 1/2008 |
| WO | 2008/130259 | 10/2008 |
| WO | 2009/035084 | 3/2009 |
| WO | 2009/041110 | 4/2009 |
| WO | 2011/158669 | 12/2011 |

OTHER PUBLICATIONS

English translation of International Preliminary Report on Patentability issued Dec. 21, 2010 in International (PCT) Application No. PCT/JP2010/067529.

International Search Report issued Dec. 21, 2010 in International (PCT) Application No. PCT/JP2010/067529.

European Search Report (ESR) issued Sep. 13, 2013 in European patent Application No. 13 17 5872.

* cited by examiner

Fig. 1
(a)
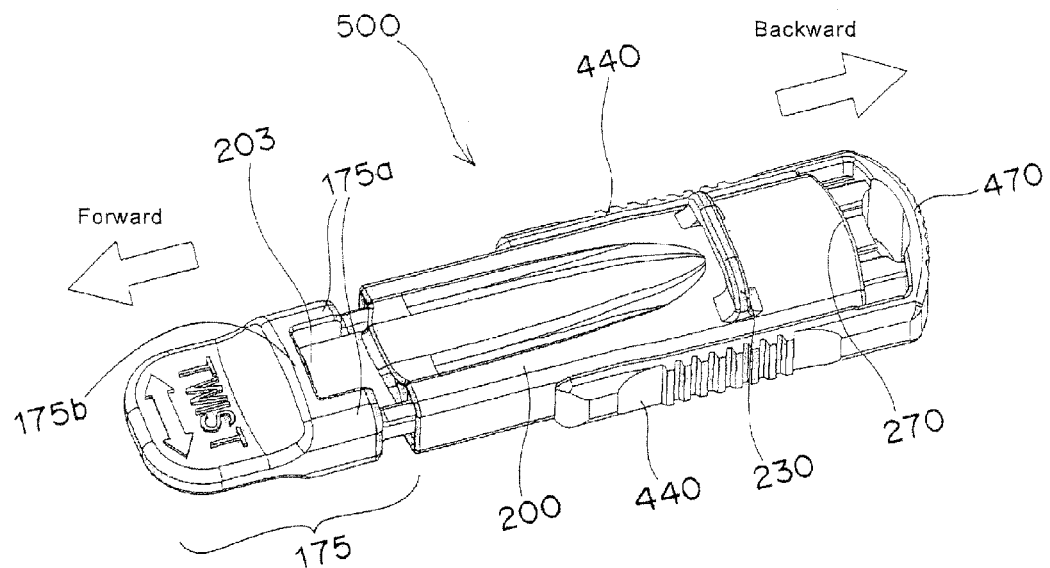
(b)
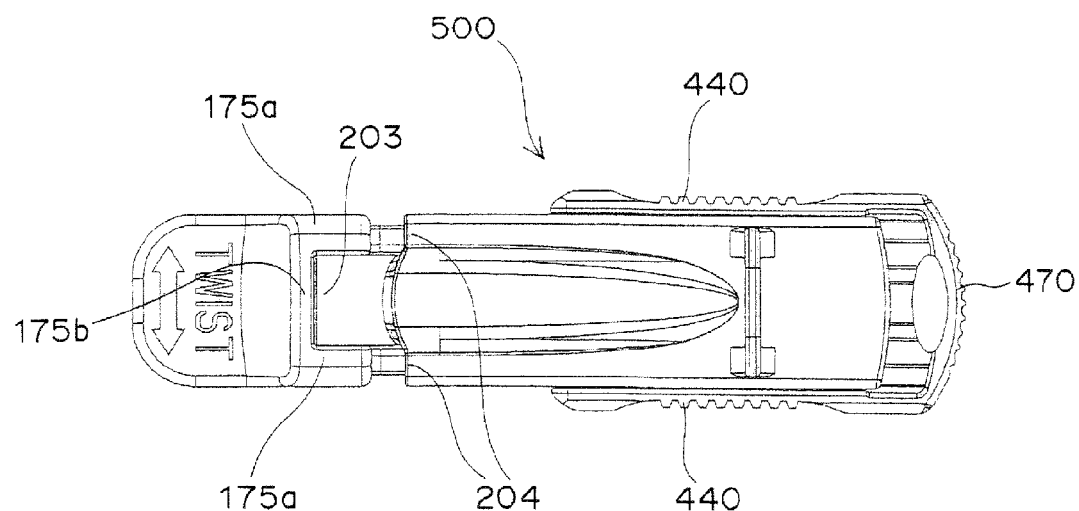

Fig. 2
Forward ← → Backward
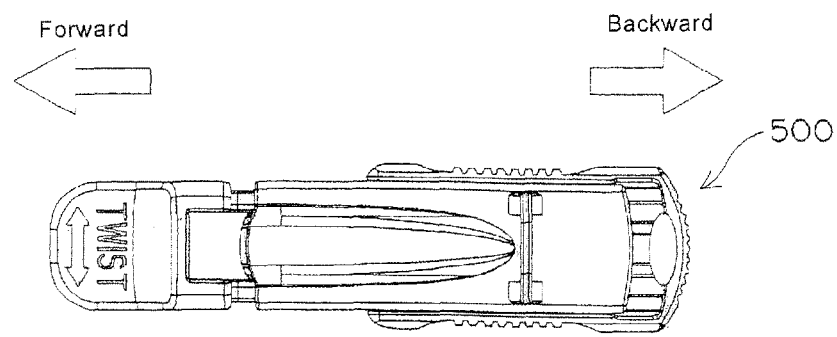
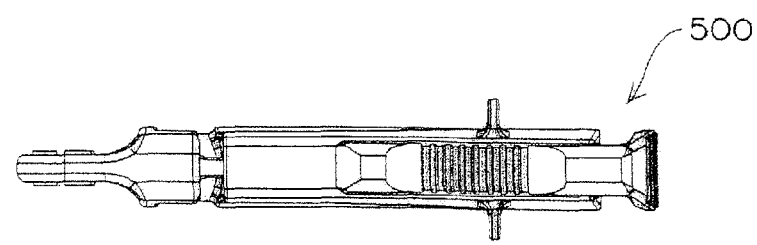
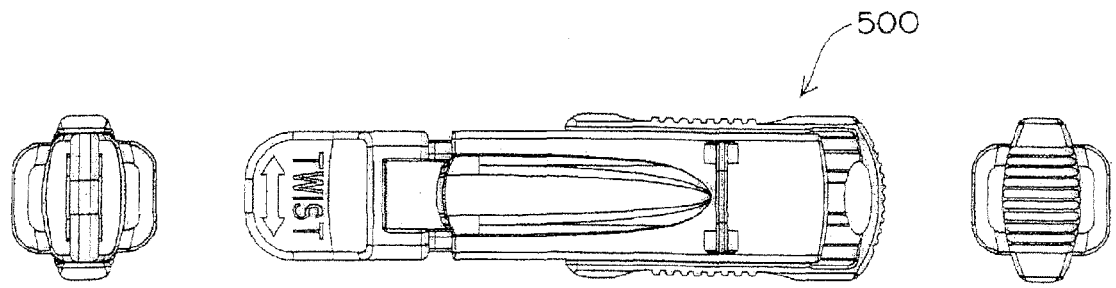
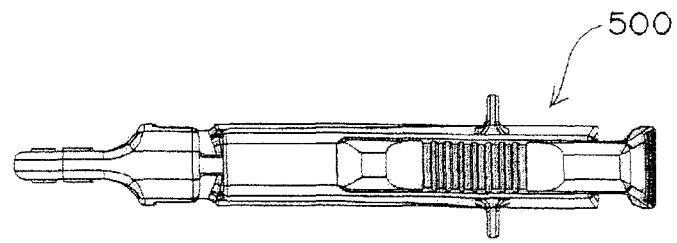

Fig. 4
(a)
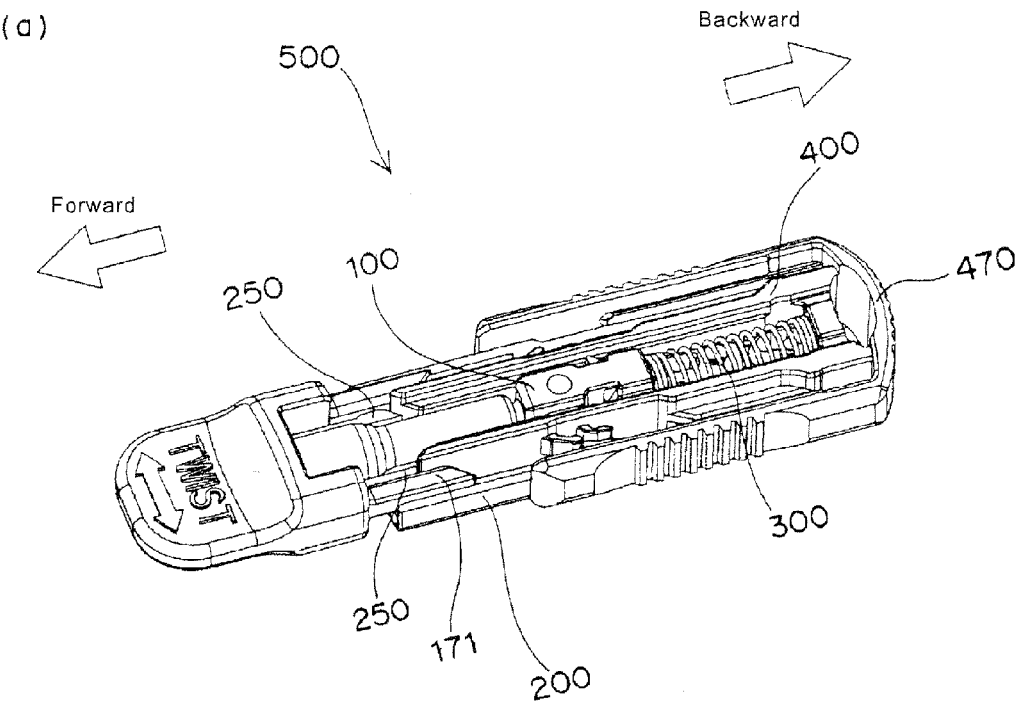
(b)
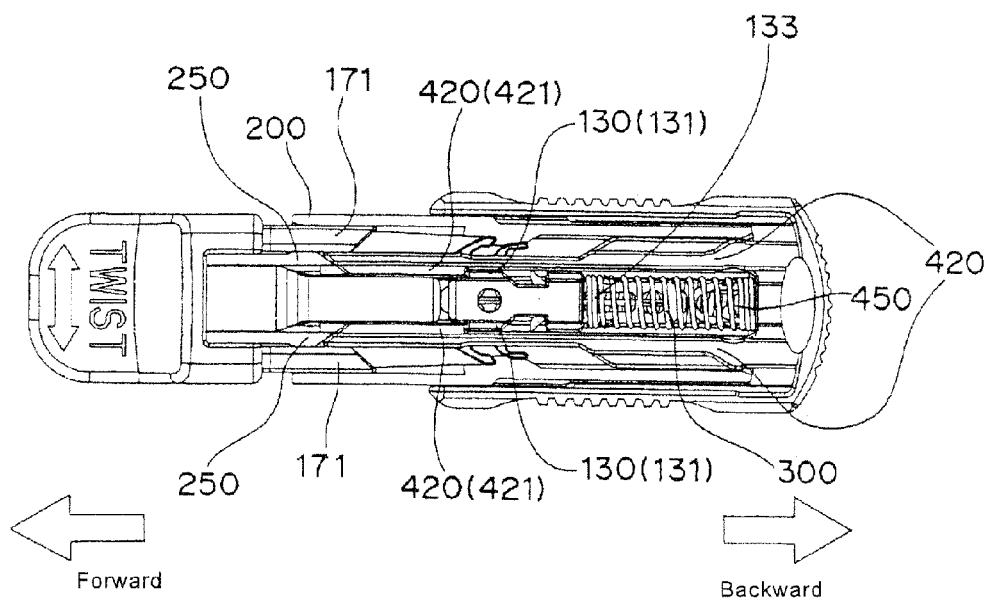

Fig. 5
(a)
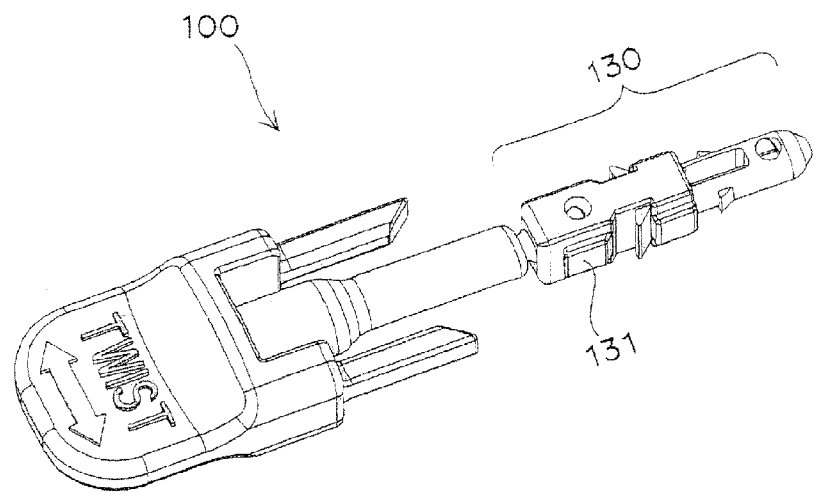
(b)
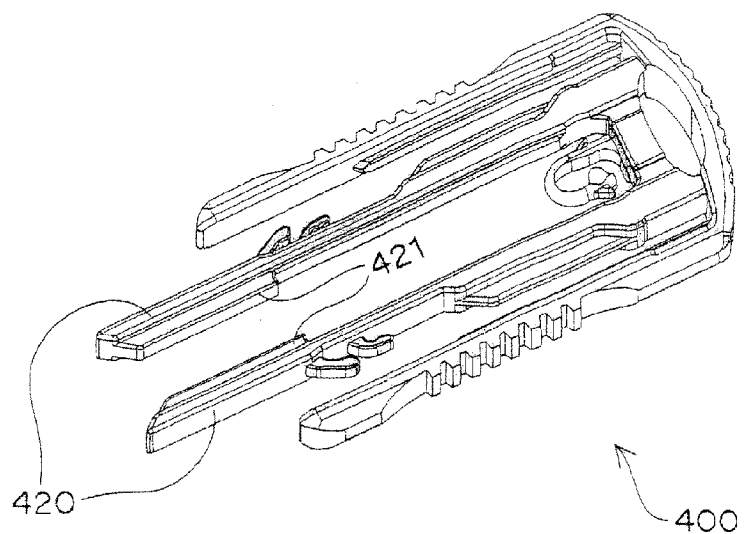

Fig. 6
(a)
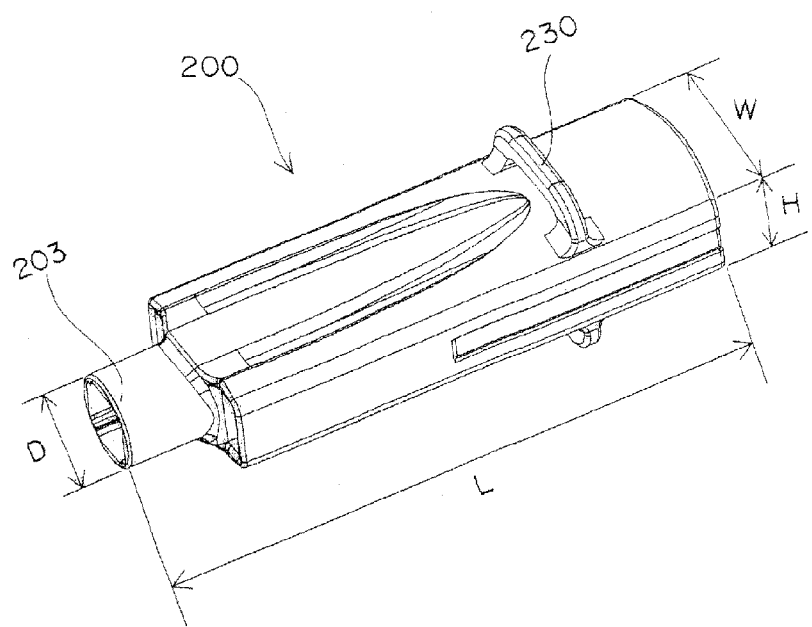
(b)
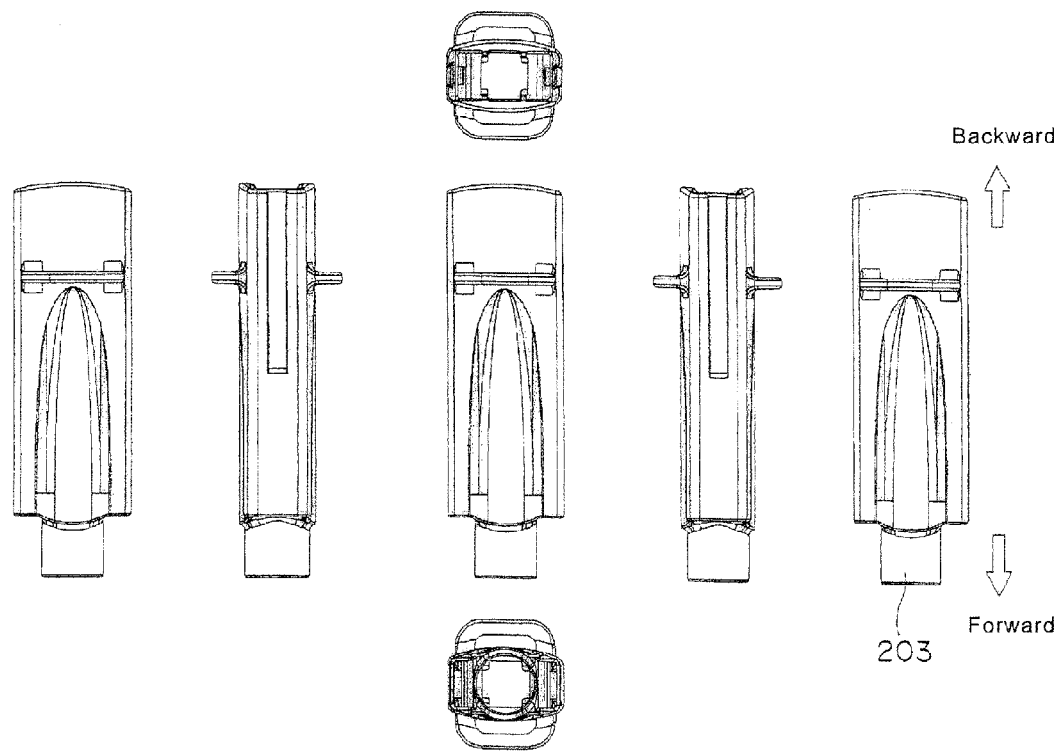

Fig. 8
(a)
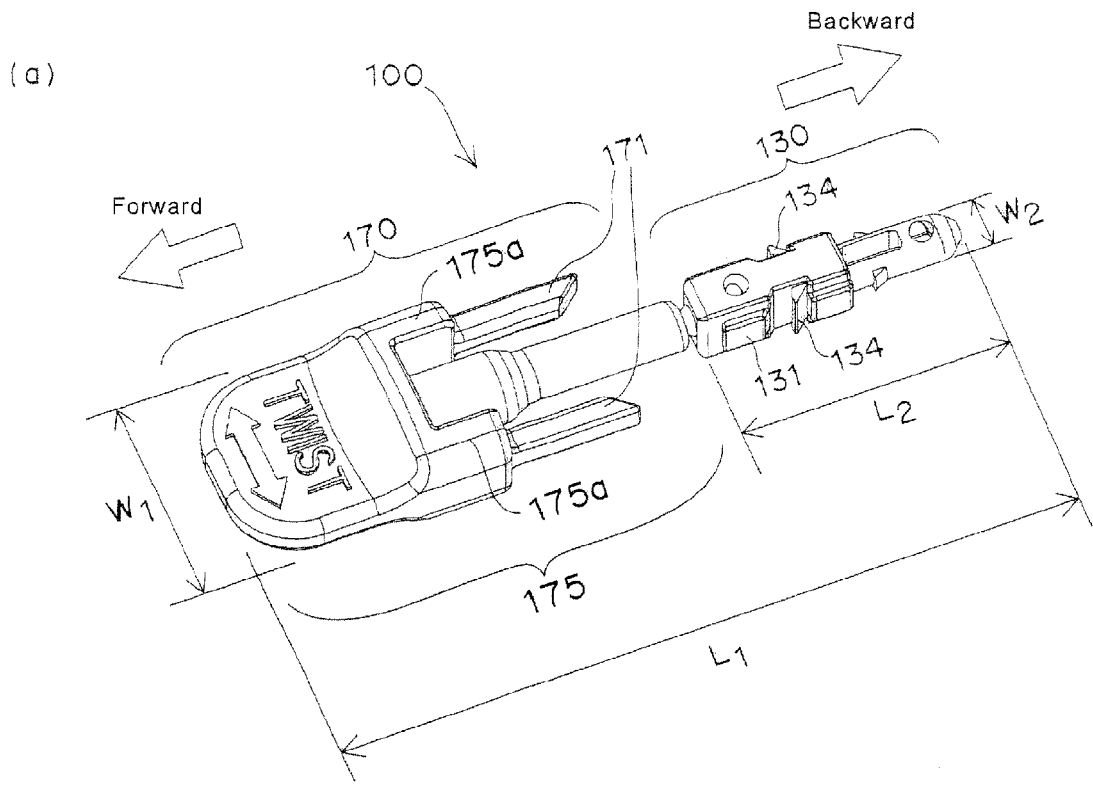
(b)
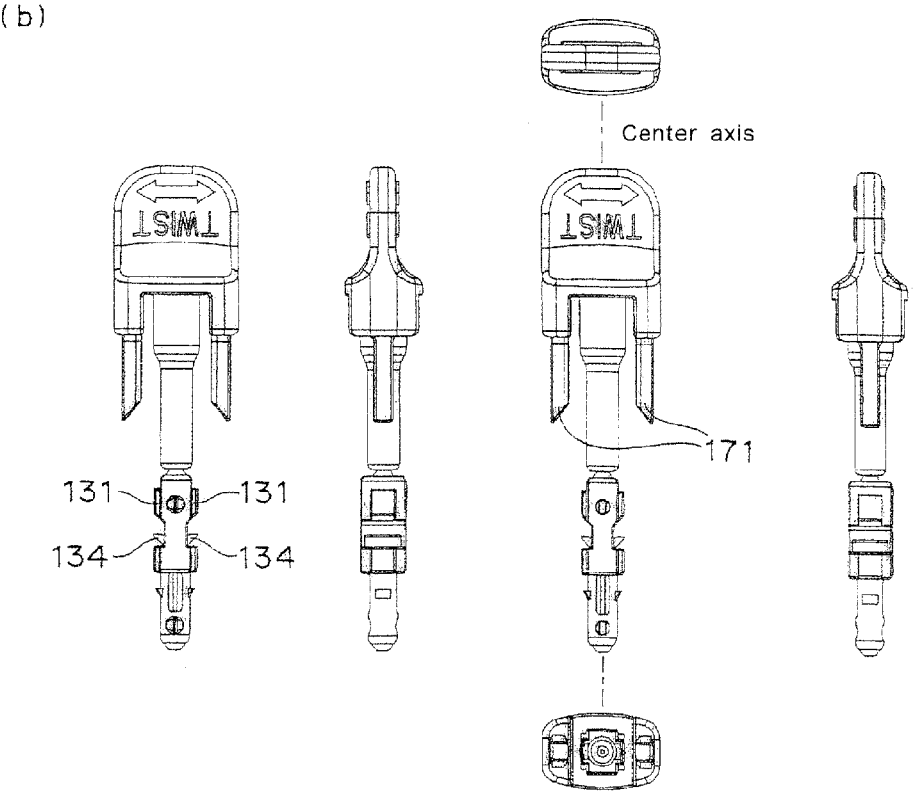

Fig. 10
(a)
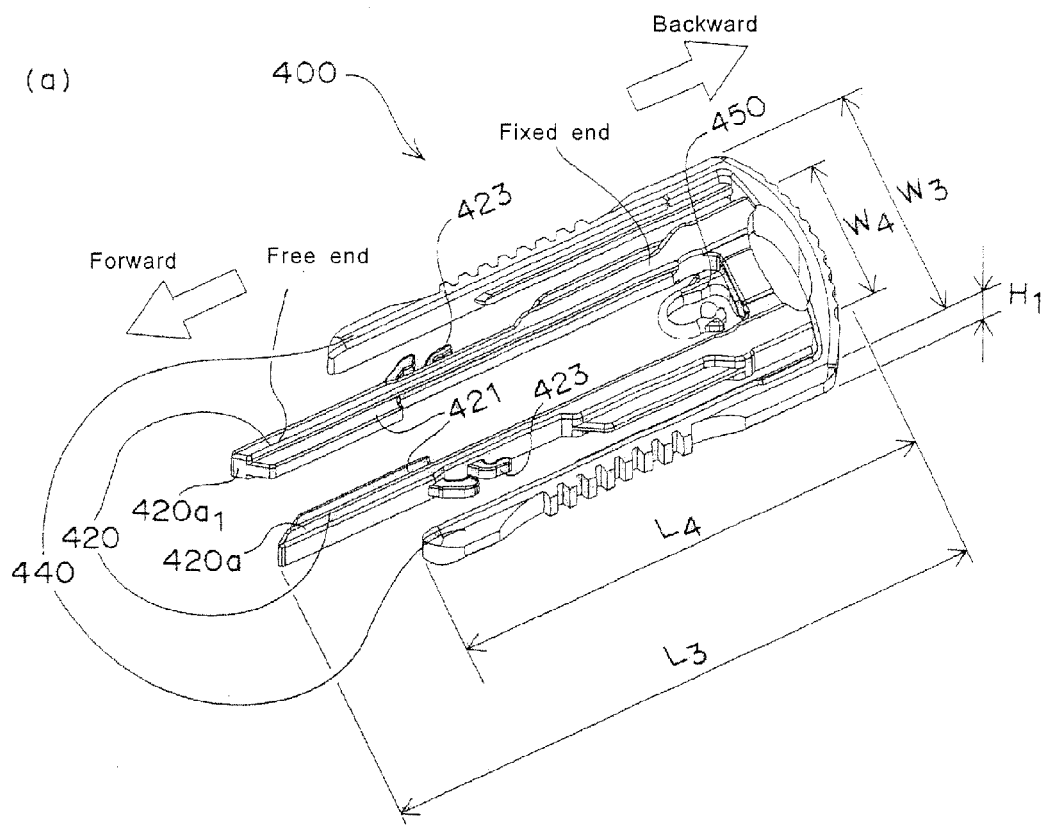
(b)
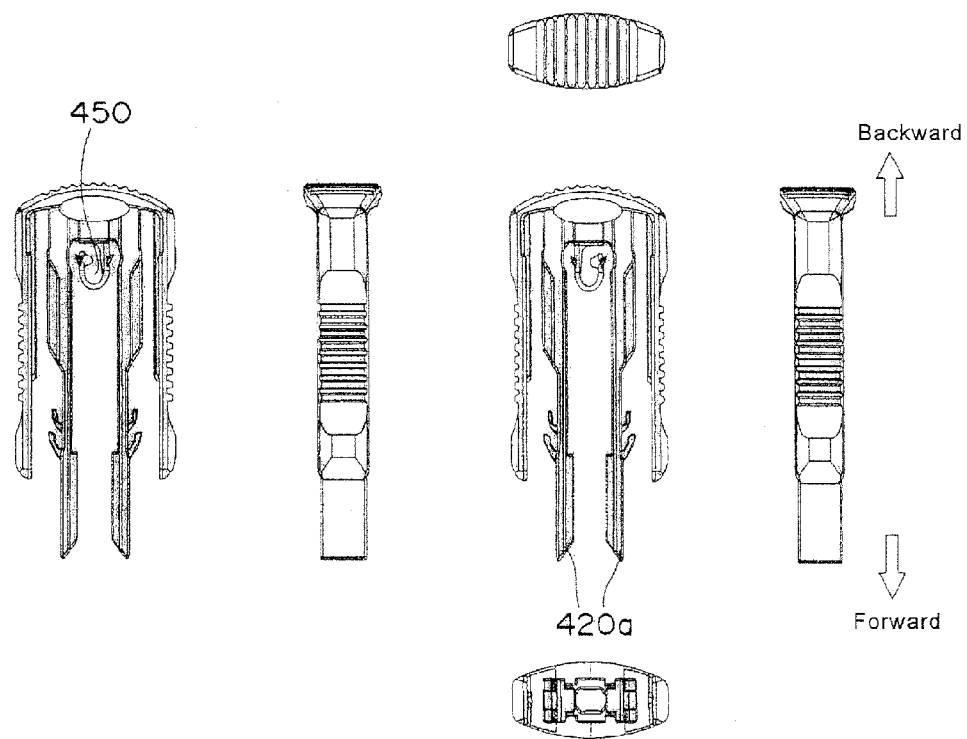

Fig. 11
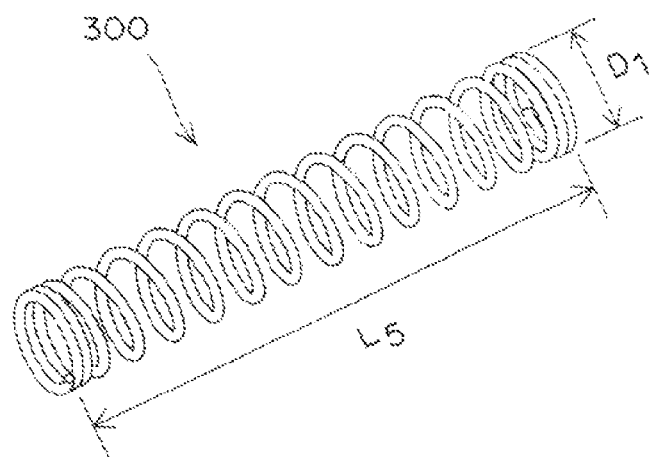
Fig. 12
(a)
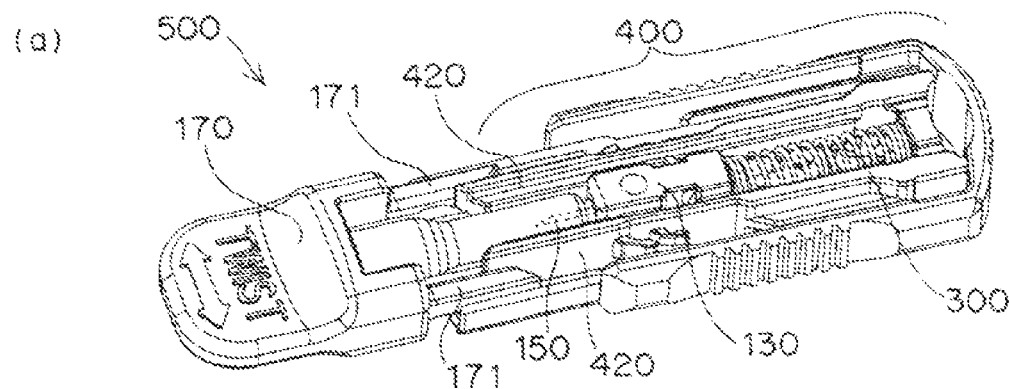
(b)
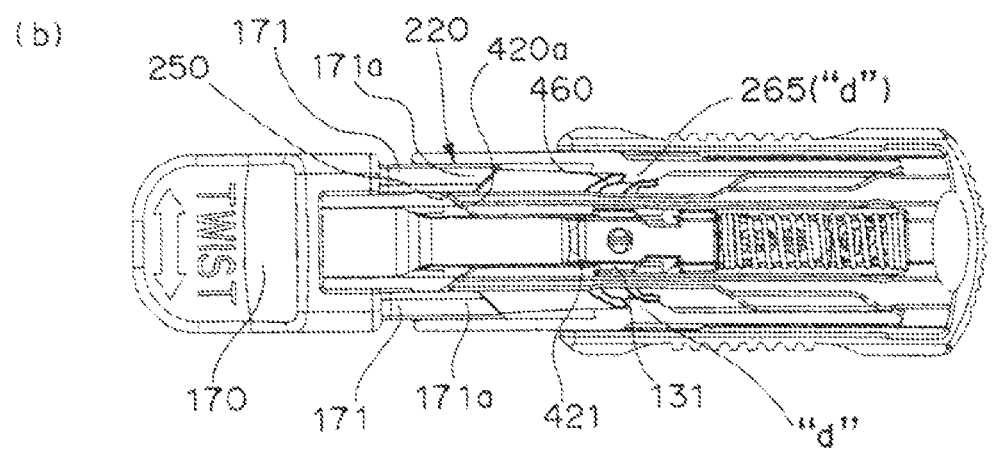

Fig. 13
(a)
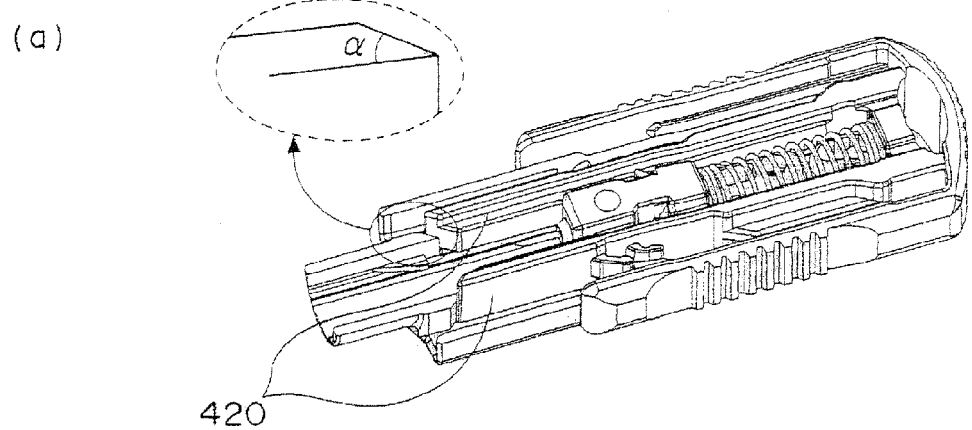
(b)
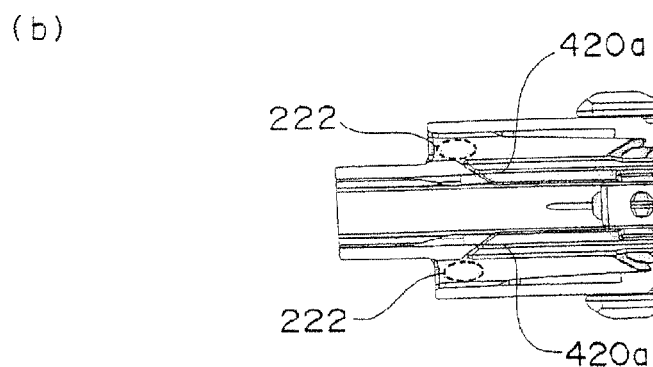

Fig. 14
(a)
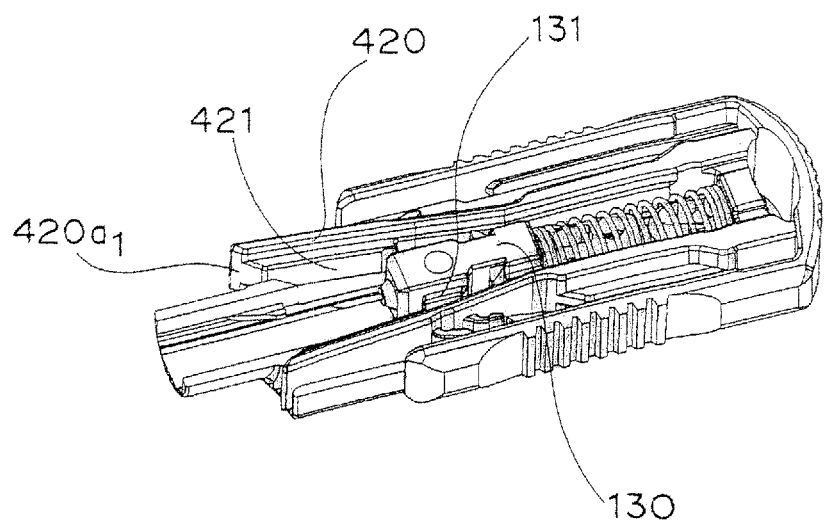
(b)
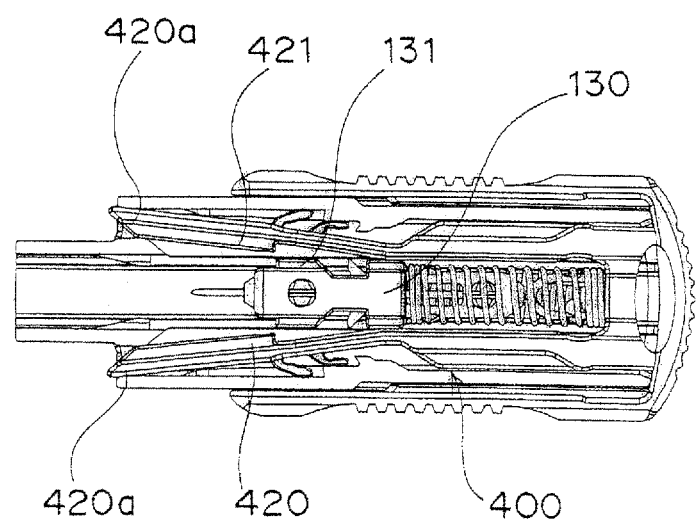

Fig. 16
(a)
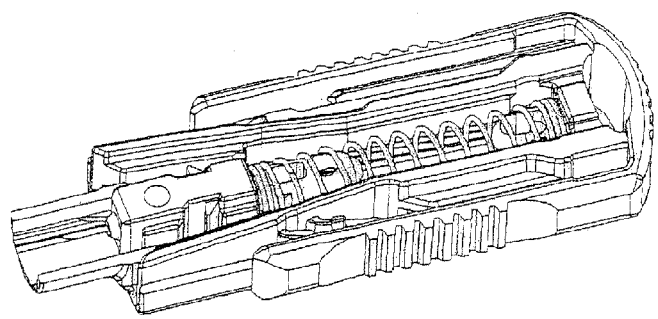
(b)
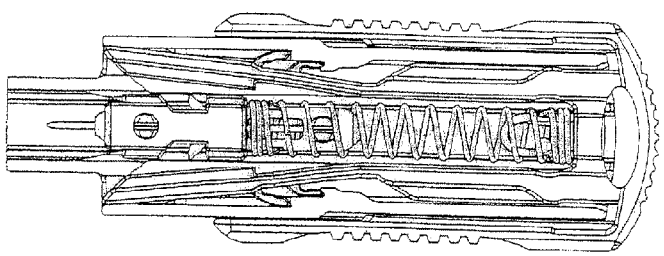
Fig. 17
(a)
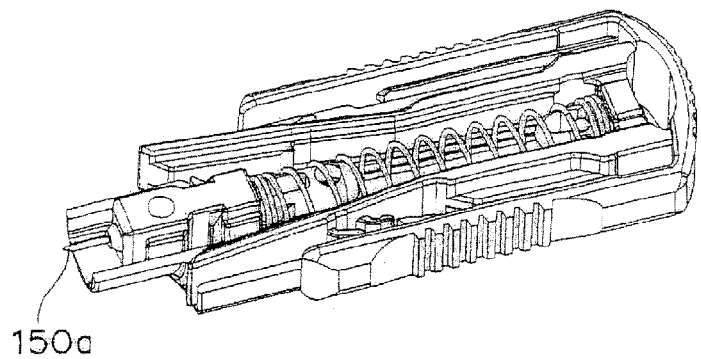
(b)
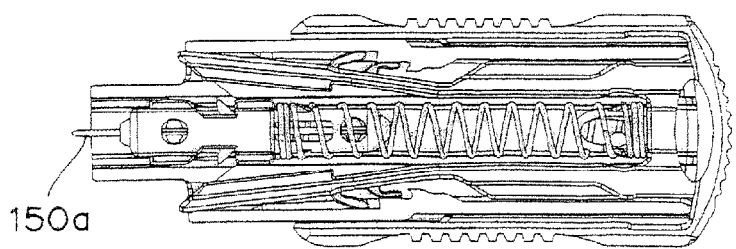

Fig. 18
(a)
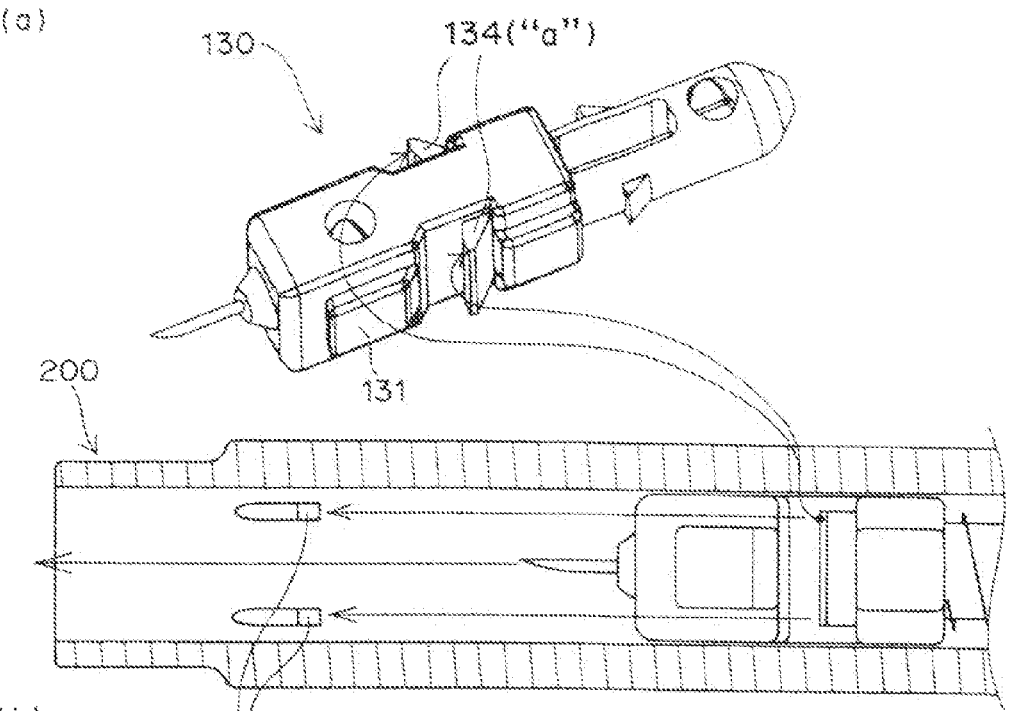
(b)
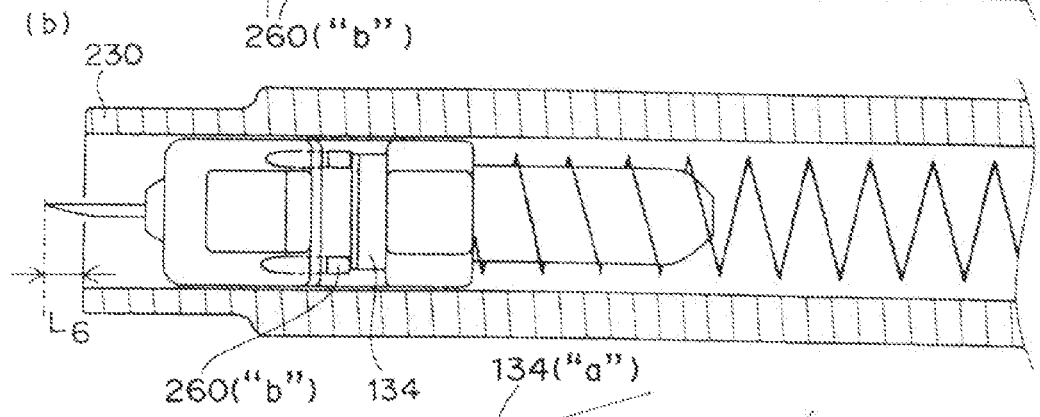
(c)
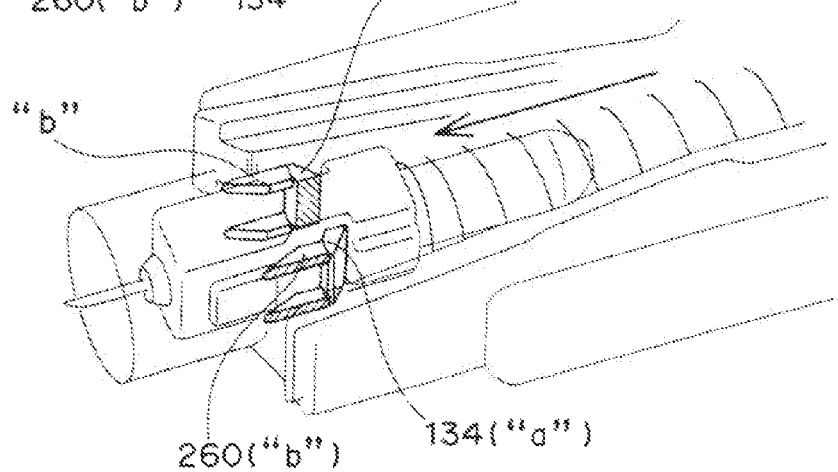

Fig. 22
(a)
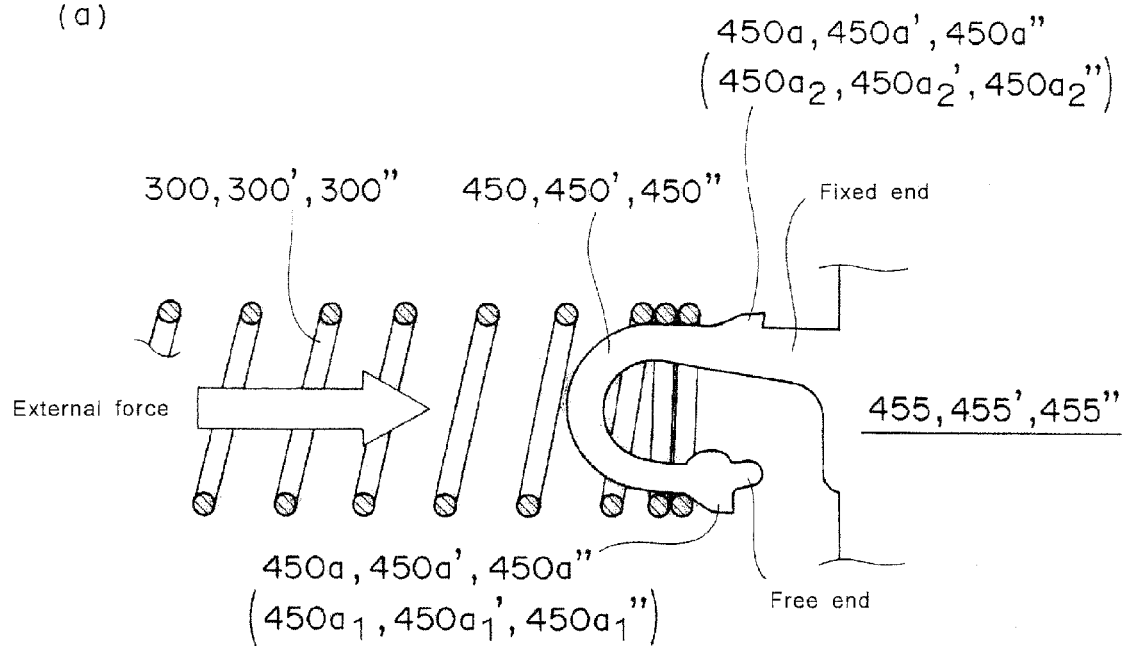
(b)
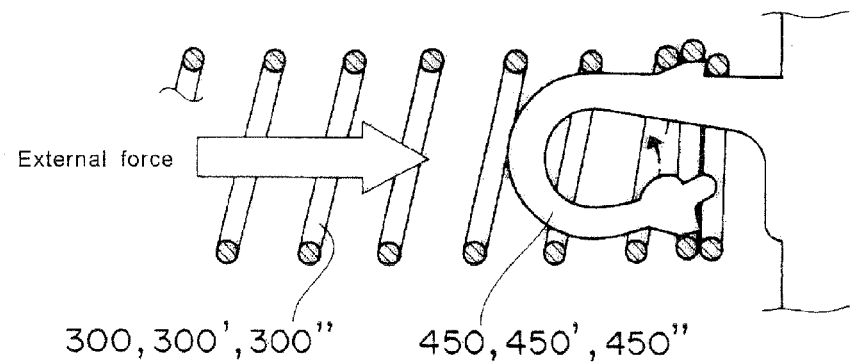
(c)
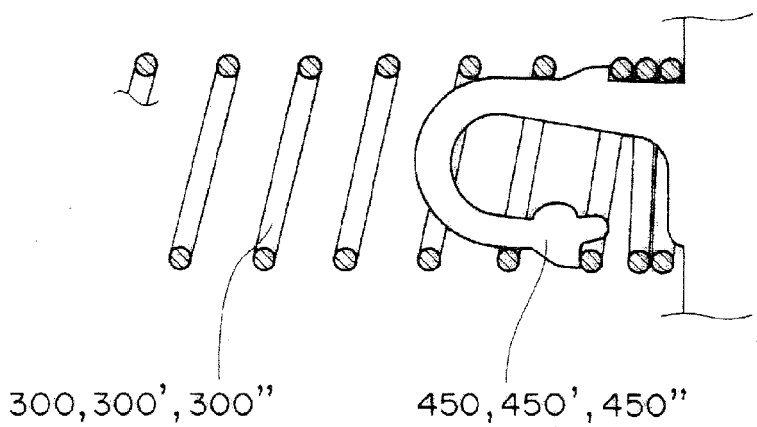

Fig. 23
(a)
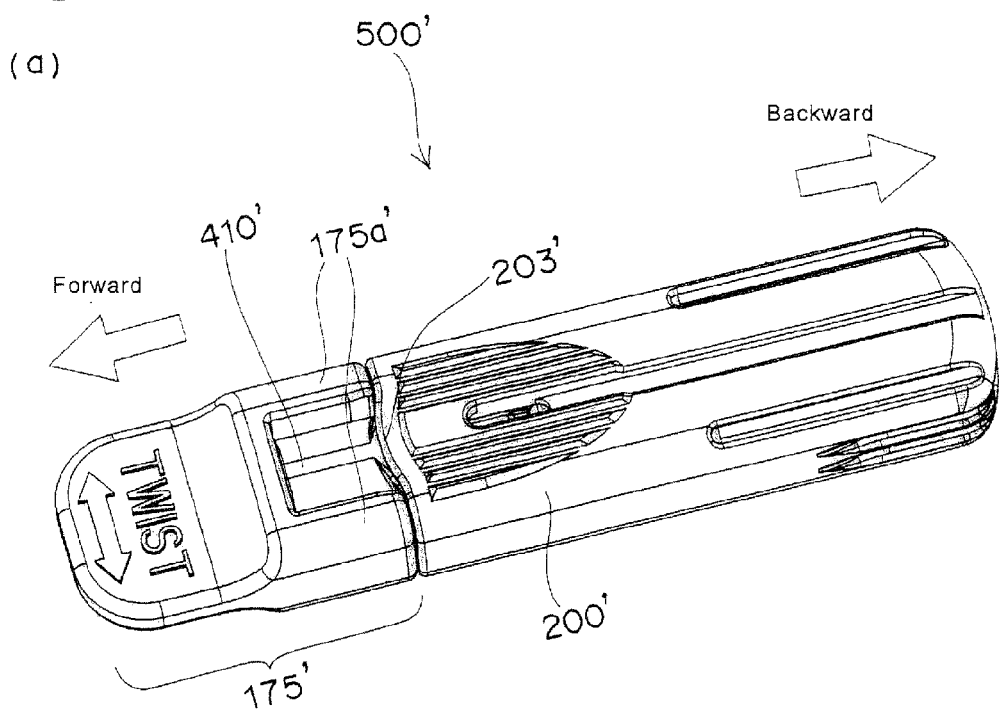
(b)
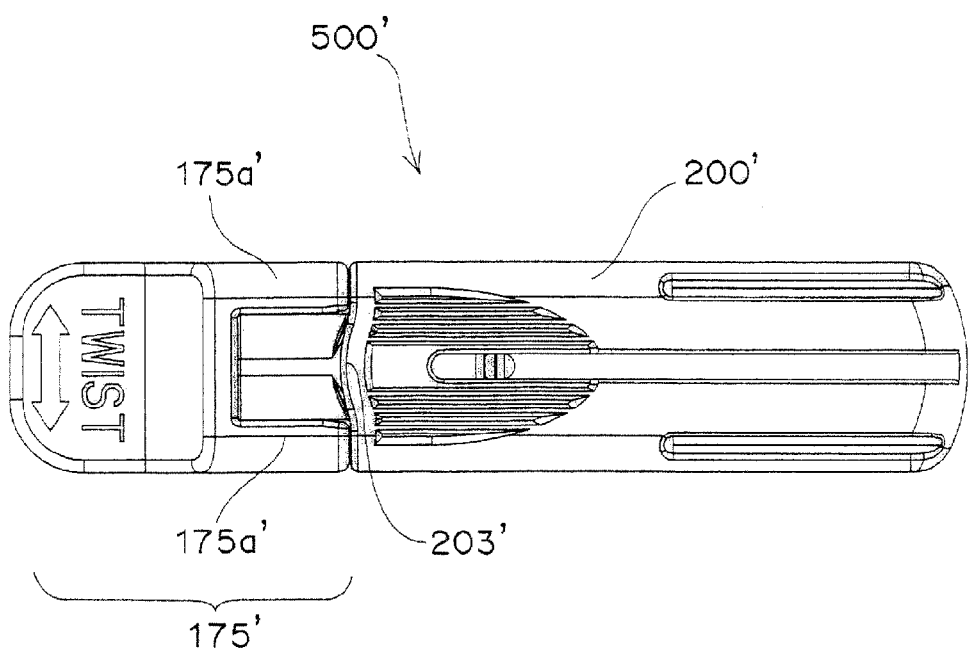

Fig. 36
(a)
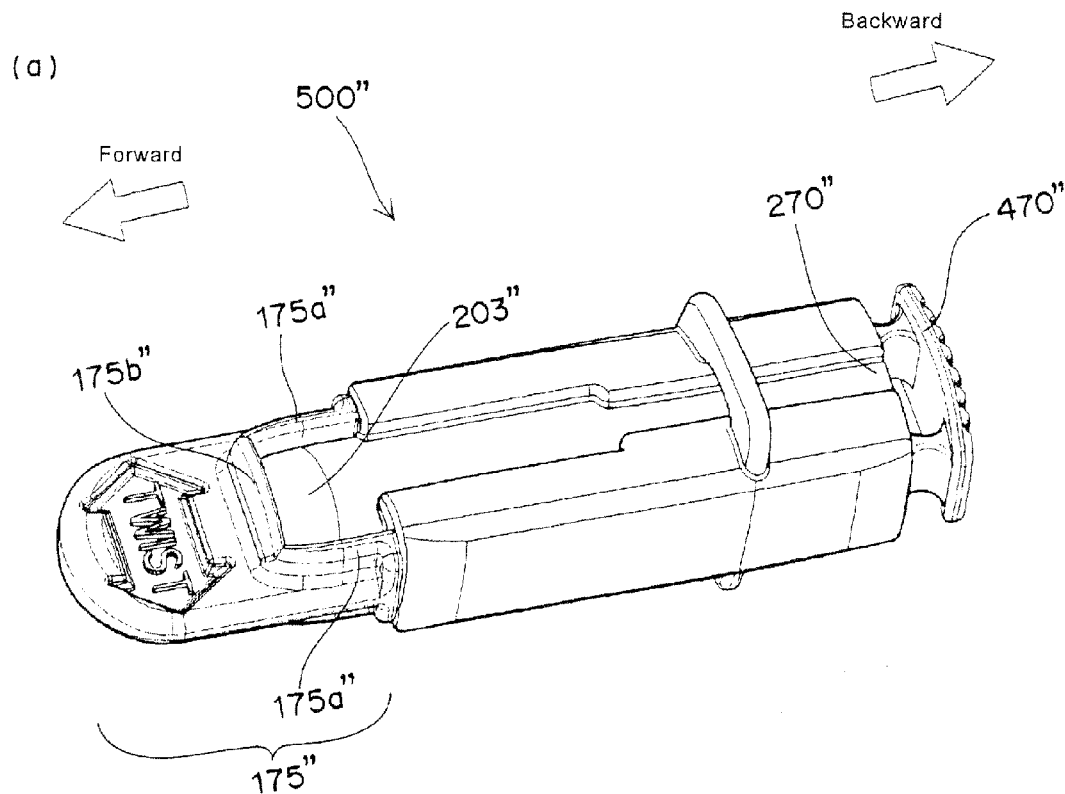
(b)
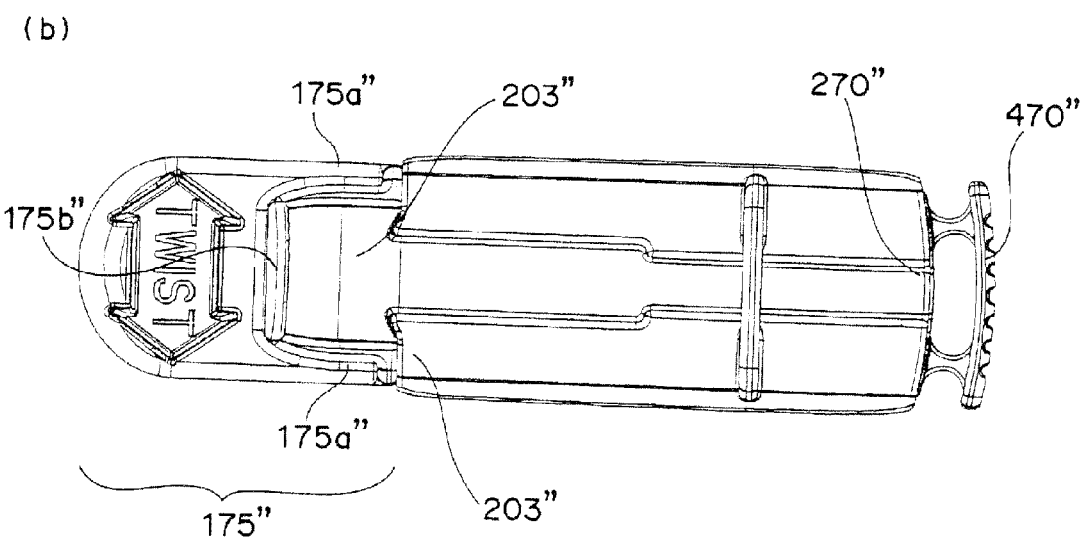

Fig. 37
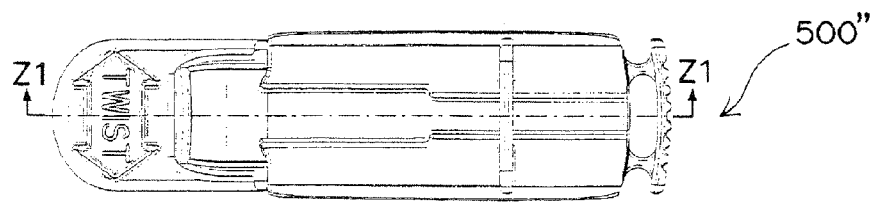
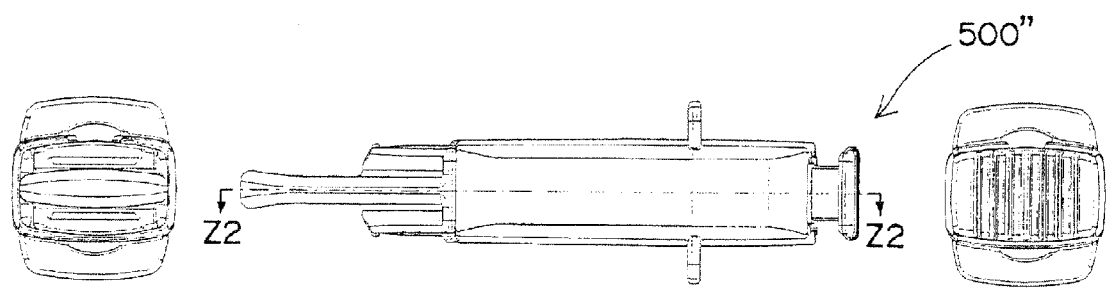
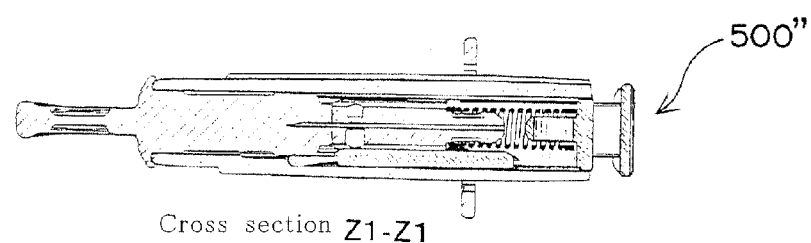
Cross section Z1-Z1
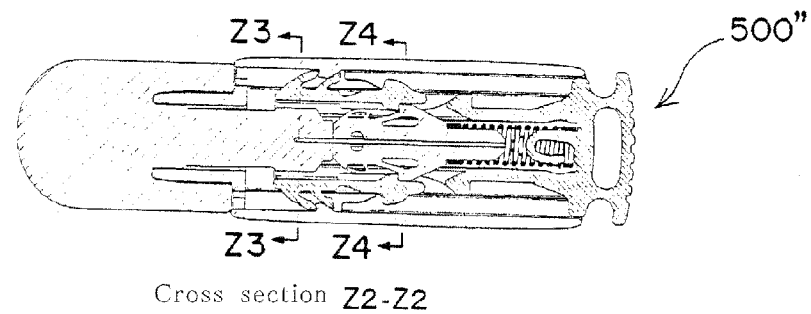
Cross section Z2-Z2
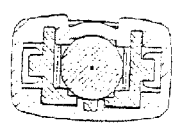
Cross section Z3-Z3
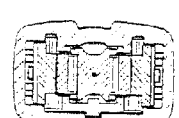
Cross section Z4-Z4

Fig. 39
(a)
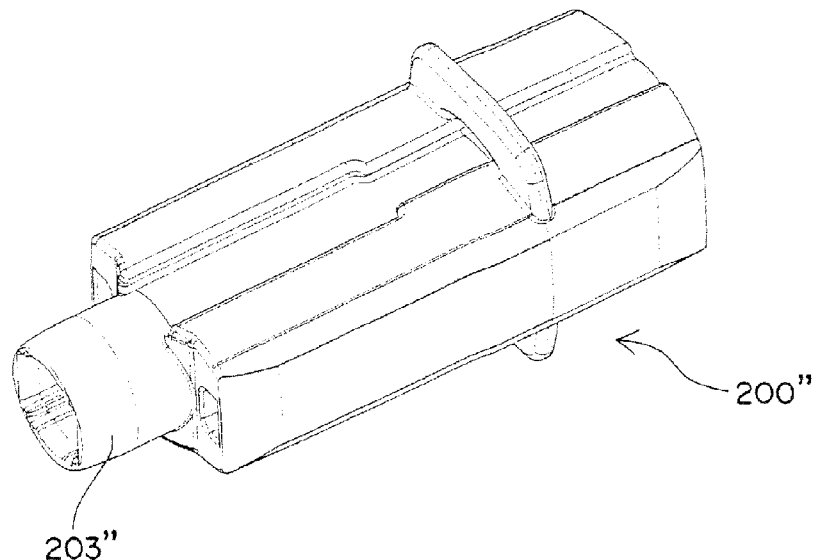
(b)
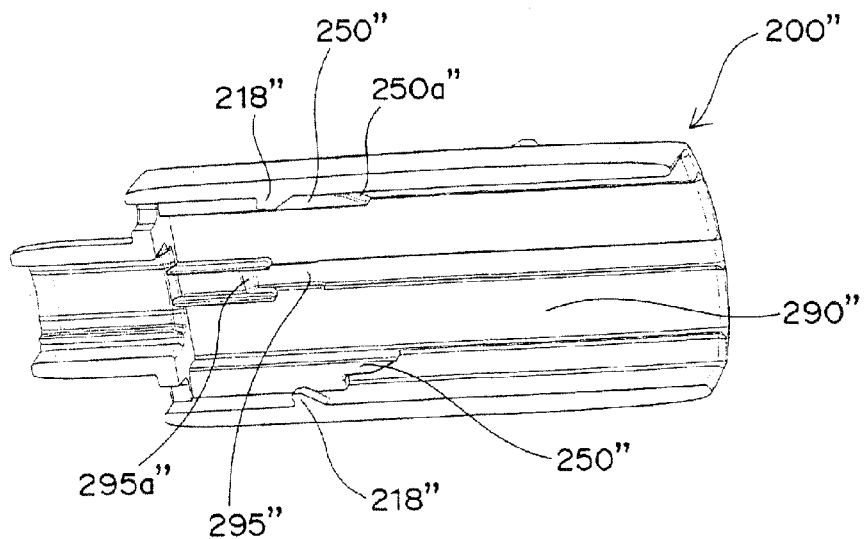
(c)
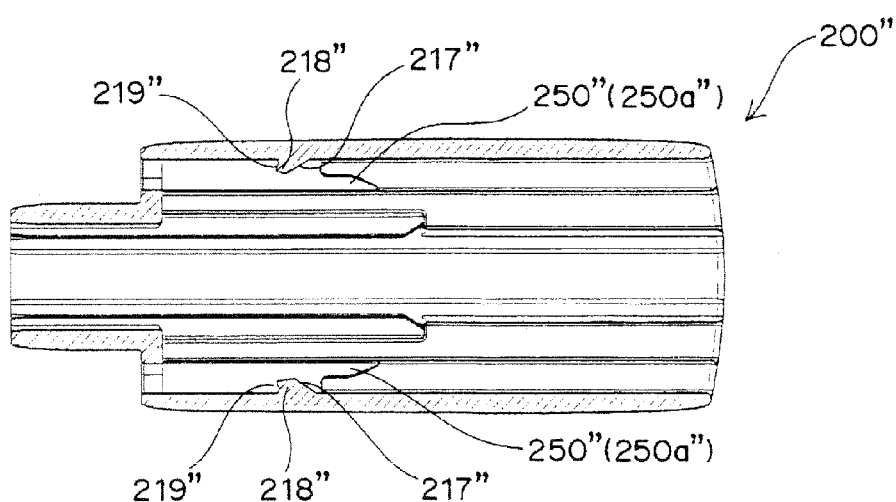

Fig. 40
(a)
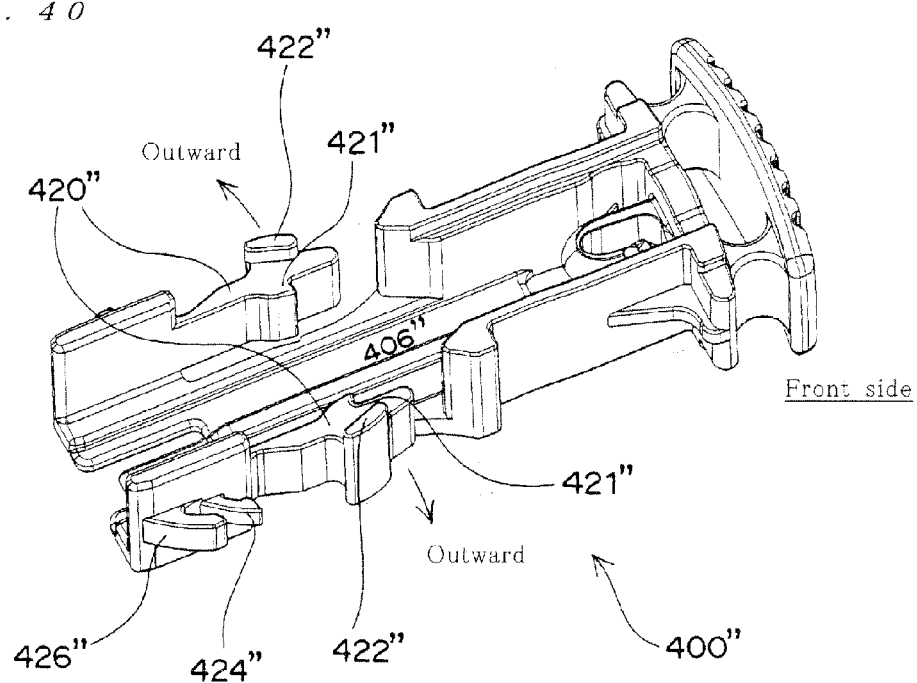
(b)
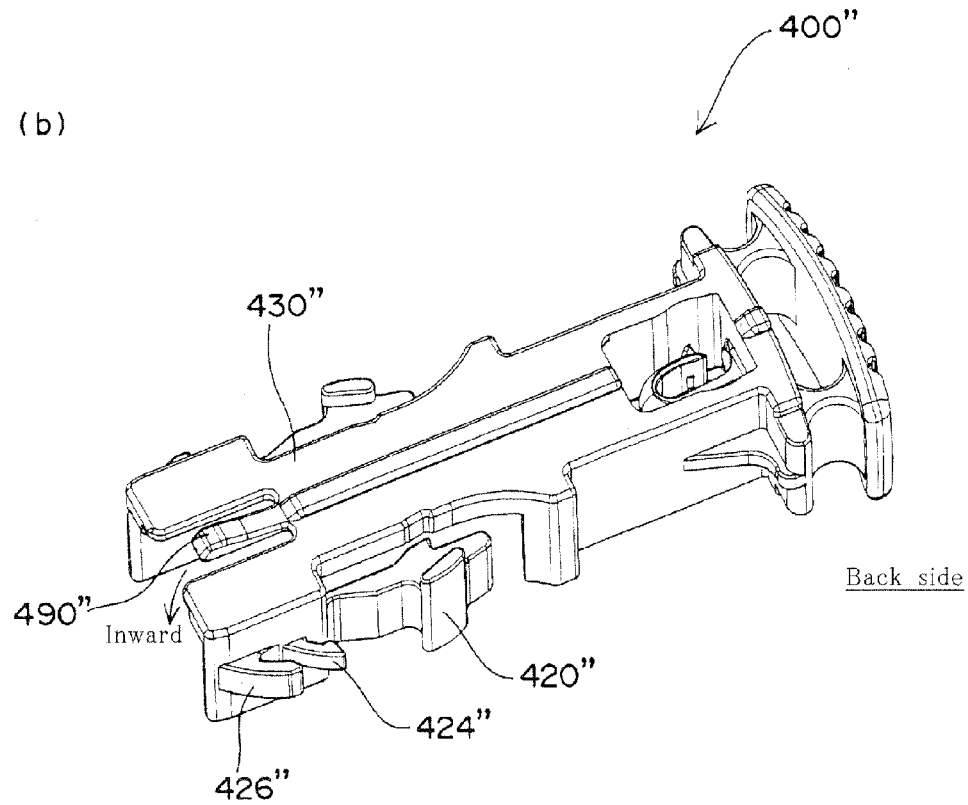

Fig. 41
(a) 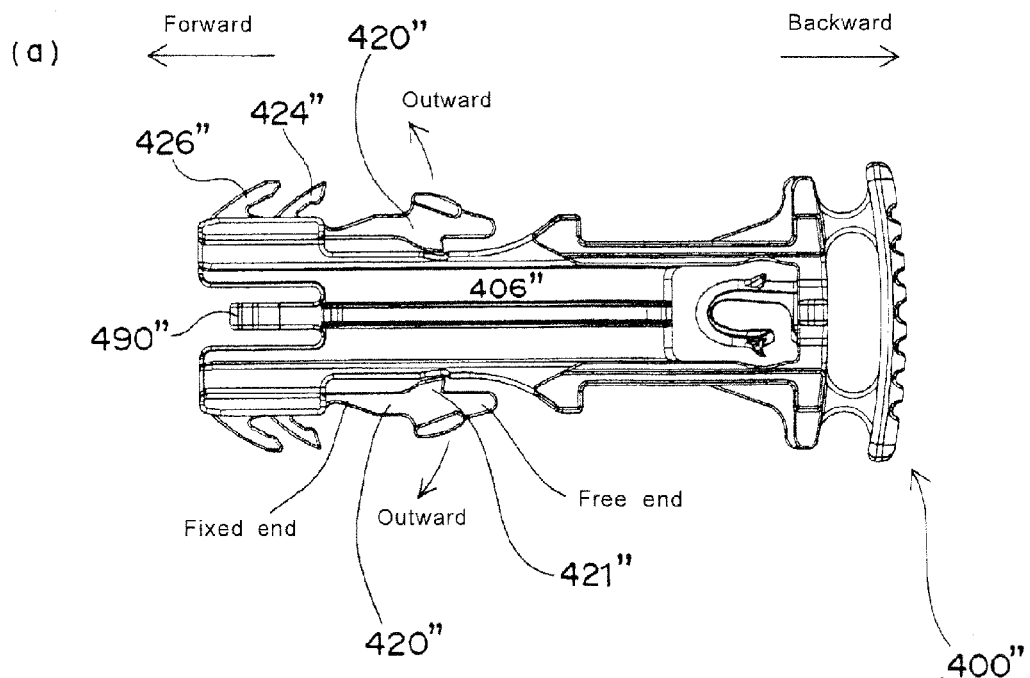
(b) 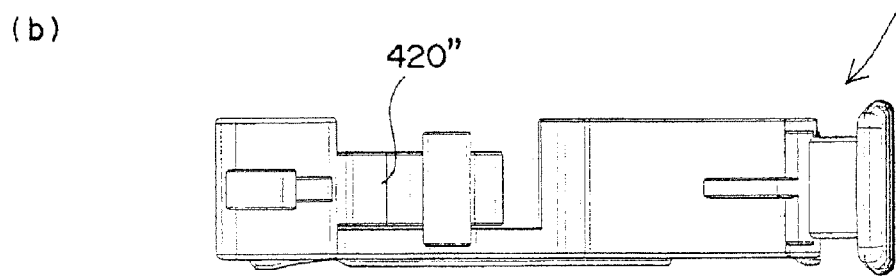
(c) 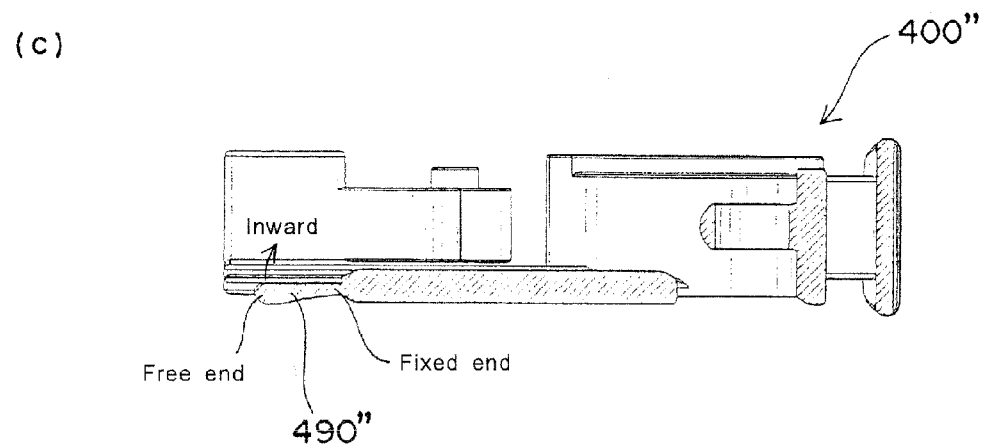

Fig. 44
(a)
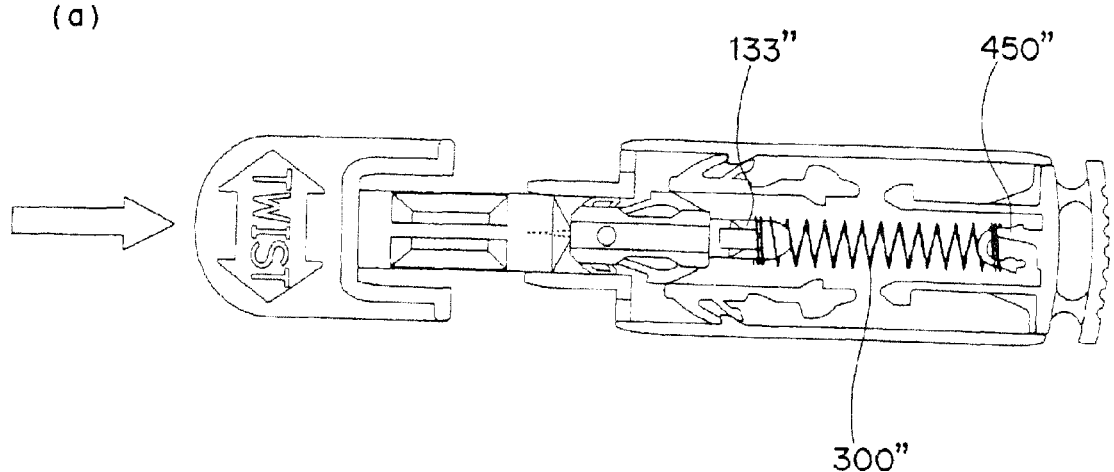
(b)
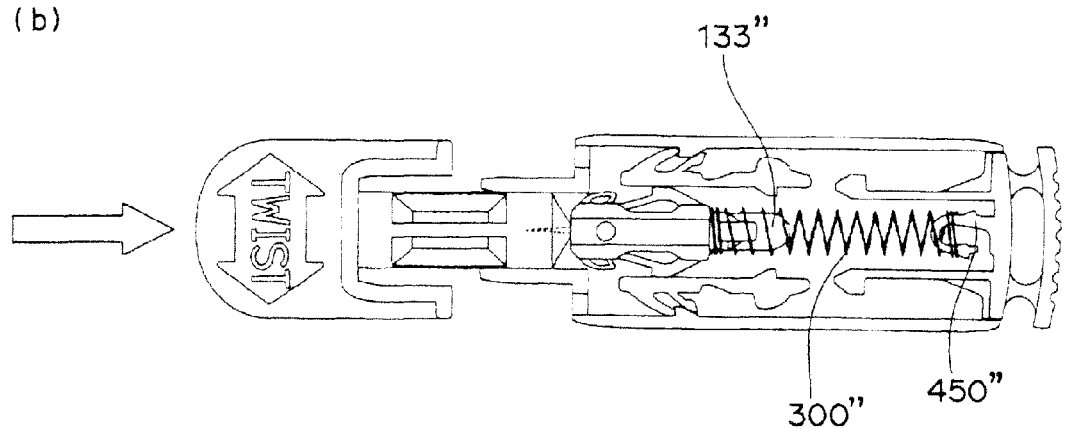
(c)
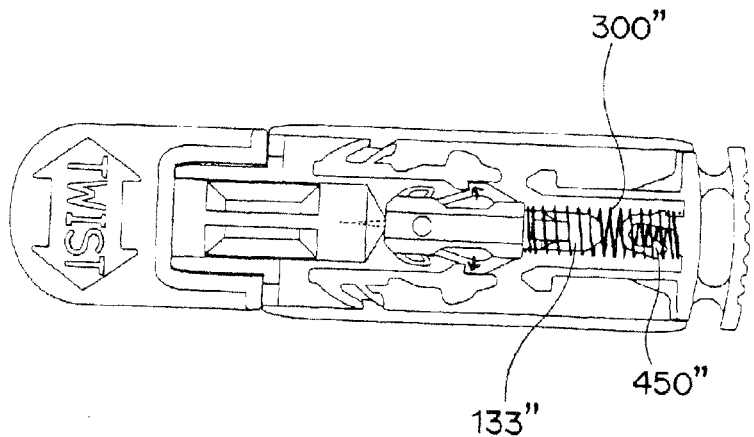

Fig. 45
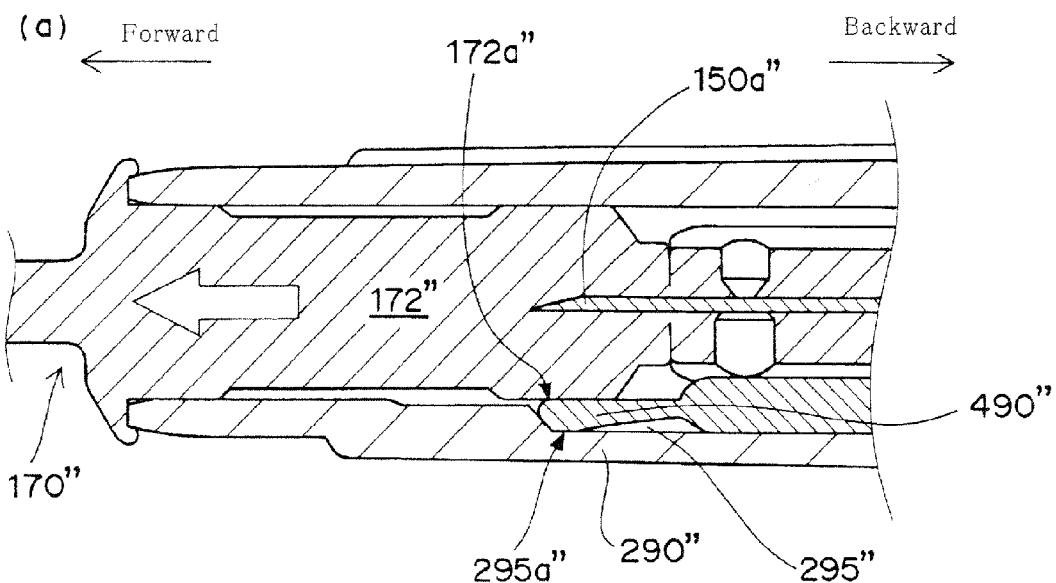
(a)
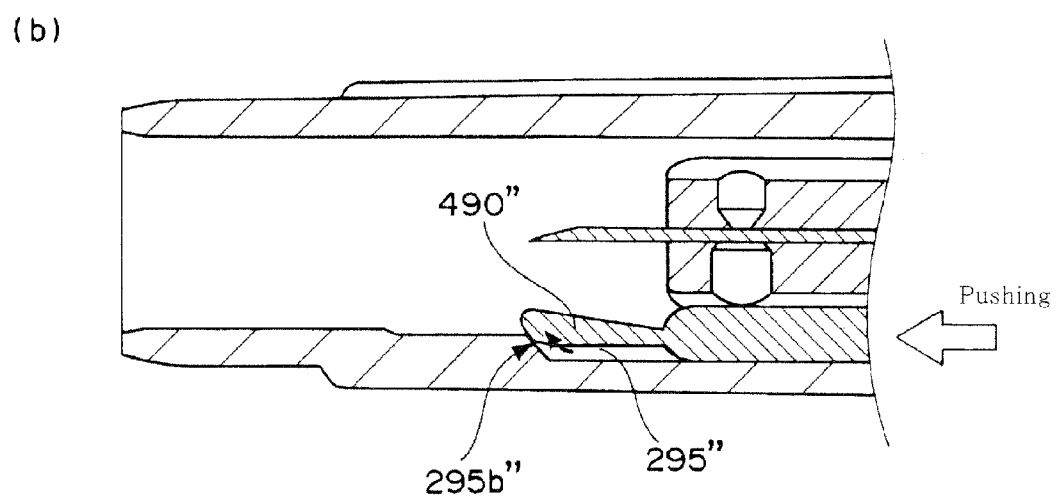
(b)
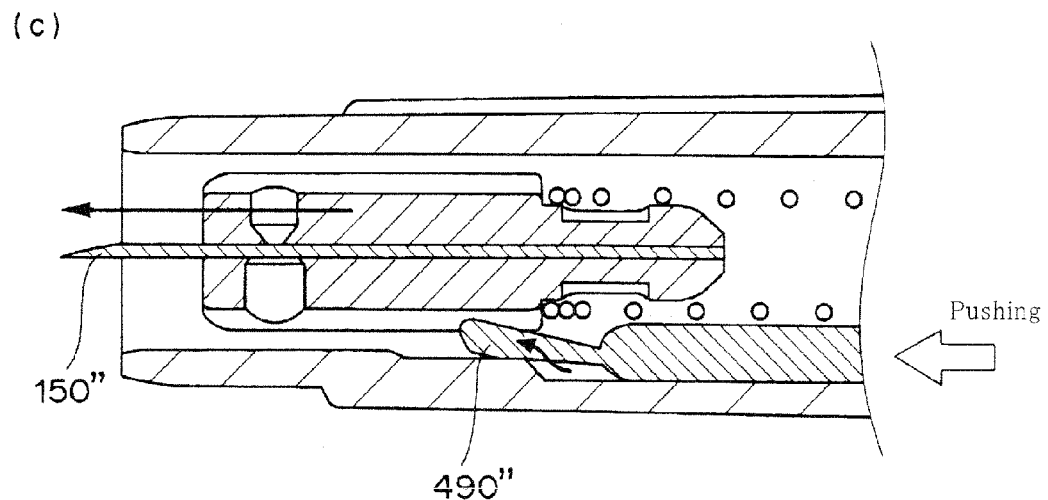
(c)

LANCET PRICKING DEVICE

TECHNICAL FIELD

The present invention relates to a pricking device. More specifically, the present invention relates to a lancet pricking device which is used for taking a sample of body fluid such as blood.

BACKGROUND ART

In order to measure a blood sugar level of a patient with diabetes, it is required to take a sample of the blood from the patient. The small amount of blood to be taken may be enough. Thus, a pricking device capable of taking a small amount of blood is used to measure the blood sugar level. The pricking device is generally composed of a lancet (see, for example, U.S. Pat. No. 5,385,571) and an injector. The lancet has a pricking needle capable of puncturing a predetermined region of the patient's body. The injector has a function of launching the lancet toward the predetermined region. The pricking device is set up for use by loading the lancet into the injector. Then, the lancet is launched toward the predetermined region by means of a plunger of the injector, whereby the predetermined region is pricked.

The pricking device used for taking blood from the patient with diabetes is required to be suitable in terms of operability and safety. For example, it is desired that the device is easy to operate for pricking and an appropriate safety measurement is provided for the handling of the used lancet. In this regard, as for the used lancet, there may be the patient's blood adhered to the pricking needle due to the pricking. If the body of a person other than the subject of the blood sampling (for example, a nurse or medical practitioner who collects the blood sample) accidentally should touch the tip of the pricking needle, the body of such person may be pricked by the pricking needle. This will result in a wound of the body through which the patient's blood may enter the body (i.e., the body of the nurse or medical practitioner), and thus posing a risk of the infection disease.

PRIOR ART DOCUMENTS

Patent Documents

Patent Document 1: U.S. Pat. No. 5,385,571

DISCLOSURE OF THE INVENTION

Problems to be Solved by the Invention

The present applicant has invented the following pricking device, and filed the application regarding such device (WO 2007/018215 A1, filed date: 8 Aug. 2006, title of the invention: "PRICKING DEVICE, AS WELL AS LANCET ASSEMBLY AND INJECTOR ASSEMBLY THAT CONSTITUTE THE PRICKING DEVICE"). Referring to the accompanying drawings, the lancet assembly and the injector assembly invented by the applicant will be briefly described below (note that the term "injector assembly" will be hereinafter referred to also as "injector"). FIG. 50 shows an external appearance of a lancet assembly 1000, and FIG. 51 shows an external appearance of an injector 2000. As shown in FIG. 50, the lancet assembly 1000 is composed of a lancet 1010 and a protective cover 1020. As shown in FIGS. 52 and 53, the lancet 1010 comprises a lancet body 1040, a lancet cap 1060 and a pricking needle 1050. The pricking needle 1050 made of metal is disposed in both the lancet body 1040 and the lancet cap 1060 both of which are made of resin. The tip of the pricking needle 1050 is covered with the lancet cap 1060, and the lancet cap 1060 and the lancet body 1040 are integrally connected together by a weakened part 1080. As shown in FIGS. 50 and 53, the protective cover 1020 is provided to enclose a part of the lancet body 1040. Such lancet assembly 1000 is loaded into the injector 2000, and then the lancet cap 1060 is removed. By the removal of the lancet cap, the tip of the pricking needle 1050 is exposed, and thereby the lancet can serve to prick.

The injector 2000 shown in FIG. 51 can be used in combination with the lancet assembly 1000 to launch the lancet body with the tip of the pricking needle 1050 exposed. The injector 2000 comprises a plunger 2040 that is capable of engaging with a rear end portion of the lancet body to launch the lancet body in the pricking direction (see FIG. 54). As shown in FIG. 54, the lancet assembly 1000 is loaded into the injector 2000 by inserting the lancet assembly 1000 into the injector 2000 through a front end opening 2140 of the injector 2000. As shown in FIG. 55, when the lancet assembly is inserted to some degree, a rear portion 1160 of the lancet assembly 1000 is held by tips 2640 and 2660 of the plunger 2040. Subsequently, when the insertion of the lancet assembly is continued, the plunger 2040 is thrust backward so that the launching energy is stored. That is, the retraction of the plunger 2040 can compress a spring (not shown) provided in the plunger 2040. This means that, when the compression of the spring is released, the plunger instantly moves forward to launch the lancet. FIG. 56 shows the injector 2000 in the state where the plunger has retracted, and the launching energy has been stored therein.

After the loading of the lancet assembly 1000 into the injector 2000 is completed, the lancet cap 1060 is removed to expose the tip of the pricking needle 1050. The removal of the lancet cap 1060 will be described as follows:

As shown in FIGS. 52 and 53, the lancet body 1040 and the lancet cap 1060 are integrally connected together by the weakened part 1080 disposed between the lancet body and the lancet cap. The weakened part 1080 is broken by rotating the lancet body 1040 and the lancet cap 1060 around the pricking needle in the reverse direction to each other (see FIG. 56 showing an embodiment of rotating the lancet cap in the direction "G"), whereby the removal of the lancet cap 1060 can be performed.

When the pricking operation is carried out, the front end opening 2140 of the injector 2000 is applied to a predetermined region to be pricked (for example, a finger tip). Subsequently, the press part 5420 of a trigger component 5140 is pushed. See FIG. 57. The pushing of the press part 5420 results in an instantaneous expansion of the compressed spring, and thereby forcing the plunger 2040 to move forwardly to prick the predetermined region with the pricking needle.

In this manner, the pricking devices needs a loading operation of charging the lancet assembly 1000 into the injector 2000 to perform the pricking, which places a large burden on the user. Moreover, such pricking device is composed of at least two components, i.e., "lancet assembly" and "injector", and thus is not compact in size as a whole (particularly because of the relatively large injector which occupies most of the device volume). Accordingly, it is desired that the pricking device has a compact size as a whole.

The present invention has been devised in view of the above-mentioned circumstances. That is, an object of the present invention is to provide a pricking device which has an improved operability and a compact size. Another object of the present invention is to provide a pricking device having its improved safety after the pricking.

Means for Solving the Problems

In order to achieve the above objects, the present invention provides a lancet pricking device, comprising:
a lancet;
a launching spring;
a trigger part; and
a holder (lancet holder) for housing therein the lancet, the launching spring and the trigger part,
wherein the lancet comprises a lancet body, a lancet cap and a pricking needle, and the pricking needle is disposed in both the lancet body and the lancet cap;
wherein the trigger part comprises a pair of arms positioned inside the holder;
wherein the launching spring is attached to the lancet body, and the lancet body is secured to the arms of the trigger part by an abutment of the lancet body on the arms such that the launching spring is kept compressed before a pricking operation;
wherein the trigger part cannot be pushed toward the inside of the holder at a point in time before the lancet cap is removed from the lancet, and whereas the trigger part can be pushed toward the inside of the holder at a point in time after the lancet cap is removed from the lancet; and
wherein the arms of the trigger part become capable of warping upon the pushing of the trigger part toward the inside of the holder to cause the secured lancet body to be released.

In such lancet pricking device, the releasing of the secured the lancet body causes the compressed launching spring to be released to perform an expansion of the spring, and thereby the "lancet body with the exposed pricking needle" is launched in the direction of pricking. It is preferred in the lancet pricking device of the invention that an inner wall of the holder (particularly, a front-sided or rear-sided inner wall surface of the holder) is provided with a sloped portion. Upon the pushing of the trigger part, the arms of the trigger part slide on the sloped portion so that the warping of the arms is caused.

The present invention is characterized at least in that the lancet pricking device is substantially composed of four components, i.e., "lancet", "trigger part", "lancet holder (lancet holder)" and "launching spring", and hence the device structure thereof is very simple. The lancet pricking device of the present invention does not have a so-called "injector", and thus is relatively small in size as a whole. In particular, the lancet body and the pricking needle of the lancet and the launching spring are positioned inside the trigger part or in the interior of the trigger part such that all of them do not protrude beyond the trigger part, which also contributes to an effective achievement of the compact size of the pricking device. The phrase "the lancet body and the pricking needle of the lancet and the launching spring are positioned inside the trigger part or in the interior of the trigger part such that all of them do not protrude beyond the trigger part" used herein means that all of the lancet body, the pricking needle and the launching spring are positioned within a space inside the trigger part. That is, such phrase substantially means an embodiment in which even a partial portion of each of the lancet body, the pricking needle and the launching spring does not protrude beyond the trigger part (for example, see the embodiments shown in FIGS. 12, 29, and 43 to be described later). In this regard, the lancet pricking device of the present invention suitably incorporates a launching means in a lancet itself to thereby achieve the compact size of the device.

The present invention is also characterized at least in that the lancet body is secured to the arms of the trigger part such that the compressed state of the launching spring is maintained until the pricking operation, and that such securing of the lancet body can be released through the removal of the lancet cap. Specifically, at a point in time before the pricking operation of the lancet pricking device of the present invention is performed (i.e., in the state where the tip of the pricking needle is covered with the lancet cap), a lancet cap's portion other than the holding portion of the lancet cap serves to prevent the pushing of the trigger part due to an interaction of the lancet cap's portion with the holder. This will be described by taking the following example. While the lancet cap is attached to the lancet, the tip of the each arm of the trigger part is positioned between "tip of each of cap arms provided in the lancet cap" and "sloped portion provided in the holder". As a result, the pushing of the trigger part toward the inside of the holder is prevented. That is, even when the trigger part is intended to be pushed toward the inside of the lancet holder by pressing it from the outside, the tip of the each arm of the trigger part abuts against both the tip of the each cap arm of the lancet cap and the sloped portion (that is, the each arm of the trigger part and the each cap arm of the lancet cap repel each other via the sloped portion), and thereby the pushing of the trigger part toward the inside of the lancet holder is prevented. This means that, when the needle is still covered with the lancet cap, the securing of the lancet body cannot be released, and thus the pricking needle is not launched. While on the other hand, after the lancet cap is removed, a space for the movement of the arms of the trigger part in the holder is generated. As a result, the pushing of the trigger part toward the inside of the holder by the pressing force from the outside can be performed. This means that, after the lancet cap is removed, the securing of the lancet body can be released, and thereby the pricking needle can be launched.

The term "warp" or "warping" as used herein regarding the arms of the trigger part substantially means various types of displacements of the arms in which the each arm is displaced in an interior space of the lancet holder. Thus, just by way of example, the term "warp" or "warping" means that the each arm is displaced outwardly within the lancet holder. Especially it means that the arms of the pair are expanded outwardly as a whole such that the tips of the arms, which serve as free ends of the arms, move away from each other.

In a preferred embodiment, a launching spring is attached to a spring-attachment portion provided at a rear-sided inner wall of the trigger part (i.e., inner wall surface of a rear end of the trigger part), and the spring-attachment portion has a bent form of an elongated part with a free end and a fixed end.

The lancet pricking device with the above features can be embodied in various forms.
(Lancet Pricking Device of Type A)

The lancet pricking device of Type A, has a feature that the each arm of the trigger part has its front side serving as a free end and its rear side serving as a fixed end, an application of the external force to the trigger part from the rear thereof causes the each arm of the trigger part to warp.

Specifically, the lancet pricking device of the type A is characterized in that the trigger part is disposed as a whole inside the holder such that a rear end of the trigger part protrudes outwardly from a rear opening end of the holder (i.e., opening provided at a rear end of the holder), and that a pair of trigger part's outer arms extending forwardly from the rear end of the trigger part is positioned at outer lateral walls of the holder;

a front portion of the lancet cap protrudes outwardly from a front opening end of the holder, and a pair of parts provided at lateral sides of the front portion of the lancet cap is adjacent to a front end of the holder, or another part of the front portion of the lancet cap (i.e., a front portion's part other than said pair) is adjacent to the front opening end of the holder such that a backward moving of the lancet with respect to the holder is prevented;

the lancet body and the pricking needle of the lancet and the launching spring are positioned inside the trigger part or in the interior of the trigger part such that all of them do not protrude beyond the pair of the arms of the trigger part, and each of the arms of the trigger part has its front side serving as a free end and its rear side serving as a fixed end in which each of lateral sides of the lancet body is secured by abutting on the each of the arms of the trigger part such that the launching spring is kept compressed before the pricking operation; and when the trigger part is forced to move forwardly with respect to the holder upon the pushing of the trigger part for the pricking, the arms of the trigger part are expanded outwardly to cause the securing of the each lateral side of the lancet body to the each arm to be released.

When the lancet cap is removed from the lancet in the lancet pricking device of the type A, the forward pushing of the trigger part can be performed. Specifically, when an external force is applied to the rear end of the trigger part or the pair of trigger part's outer arms, the trigger part can be pushed toward the inside of the holder so that the trigger part moves forwardly with respect to the holder.

In another preferred embodiment of the lancet pricking device of the type A, when the trigger part is forced to move forwardly with respect to the holder, the each arm of the trigger part (especially, the free end of the each arm) slides on a sloped portion provided at a front-sided inner wall of the holder, and thereby the outward expansion of the each arm is automatically performed.

In another embodiment of the lancet pricking device of the type A, the lancet cap comprises a pair of cap arms which extend backwardly from the pair of parts provided at the lateral sides of the front portion of the lancet cap. It is preferred in this embodiment that a tip of the each arm of the trigger part is positioned between a tip of the each cap arm of the lancet cap and the sloped portion of the holder at a point in time when the lancet still has the lancet cap (i.e., before the lancet cap is removed from the lancet). Due to such positional relationship among the each arm of the trigger part, the each cap arm of the lancet cap and the sloped portion of the holder, even when the trigger part is intended to be pushed toward the inside of the holder due to a pressing force from the outside at a point in time before the lancet cap is removed from the lancet, the tip of the each arm of the trigger part abuts against both the tip of the each cap arm of the lancet cap and the sloped portion of the holder, whereby the pushing of the trigger part toward the inside of the holder is prevented.

In another preferred embodiment of the lancet pricking device of the type A, a re-use preventing wing is provided at an outer face of the each arm of the trigger part such that it extends backwardly and obliquely, and whereas a re-use preventing protrusion is provided at an inner wall of the holder; and upon the pushing of the trigger part in the pricking operation, the re-use preventing wing of the each arm of the trigger part moves forwardly while contacting on the re-use preventing protrusion of the holder until the re-use preventing wing rides over the re-use preventing protrusion; and after the pricking operation, the re-use preventing wing is capable of abutting against the re-use preventing protrusion such that the backward movement of the trigger part is restricted, and thereby the trigger part after the pricking cannot be returned to its pre-pricking state.

(Lancet Pricking Device of Type B)

The lancet pricking device of Type B, has a feature that the each arm of the trigger part has its front side serving as a fixed end and its front side serving as a free end, an application of the external force to the trigger part from the front thereof causes the each arm of the trigger part to warp.

Specifically, the lancet pricking device of the type B is characterized in that the trigger part is disposed as a whole inside the holder such that only a pricking opening portion provided at a front end of the trigger part protrudes outwardly from a front opening end of the holder (i.e., opening provided at a front end of the holder);

a front portion of the lancet cap protrudes outwardly from the front opening end of the holder, and a pair of parts provided at lateral sides of the front portion of the lancet cap is adjacent to the front opening end of the holder such that a backward moving of the lancet with respect to the holder is prevented;

each of the arms of the trigger part has its front side serving as a fixed end and its rear side serving as a free end in which each of lateral sides of the lancet body is secured by abutting on the each of the arms of the trigger part such that the launching spring is kept compressed before the pricking operation; and when the trigger part is forced to move backwardly with respect to the holder upon the pushing of the trigger part for the pricking, the arms of the trigger part are expanded outwardly to cause the securing of the each lateral side of the lancet body to the each arm to be released.

When the lancet cap is removed from the lancet in the lancet pricking device of the type B, the backward pushing of the trigger part can be performed. Specifically, when an external force is applied to the pricking opening portion provided at the front end of the trigger part, the trigger part can be pushed toward the inside of the holder so that the trigger part moves backwardly with respect to the holder.

In a preferred embodiment of the lancet pricking device of the type B, when the trigger part is forced to move backwardly with respect to the holder, the each arm of the trigger part (especially, the free end of the trigger part) slides on a sloped portion provided at a rear-sided inner wall of the holder, and thereby the outward expansion of the each arm is automatically performed.

In another preferred embodiment of the lancet pricking device of the type B, the each arm of the trigger part is provided with a component for applying a force to the each arm in a lateral direction of the lancet body. It is preferred in this embodiment that "component for applying the force to the each arm of the trigger part in the lateral direction of the lancet body" is a push-back portion capable of pushing an inner wall of the holder, or capable of pushing the inner wall of the holder when the outward expansion of the each arm of the trigger part starts. For example, the push-back portion may be in an arm form that protrudes outwardly and obliquely from the each arm of the trigger part.

In still another embodiment of the lancet pricking device of the type B, a re-use preventing wing is provided at a rear-sided outer wall face of the trigger part such that it extends forwardly and obliquely, and whereas a re-use preventing protrusion is provided at an inner wall of the holder;

upon the pushing of the trigger part in a pricking operation, the re-use preventing wing of the trigger part moves backwardly while contacting on the re-use preventing protrusion of the holder until the re-use preventing wing rides over the re-use preventing protrusion; and after the pricking operation, the re-use preventing wing is capable of abutting against the re-use preventing protrusion such that a forward movement of the trigger part is restricted, and thereby the trigger part after the pricking cannot be returned to its pre-pricking state.

(Lancet Pricking Device of Type C)

The lancet pricking device of Type C, has a feature that the each arm of the trigger part has its front side serving as a fixed end and its rear side serving as a free end, an application of the external force to the trigger part from the rear thereof causes the each arm of the trigger part to warp.

Specifically, the lancet pricking device of the type C is characterized in that the trigger part is disposed as a whole inside the holder such that only a pressing portion provided at a rear end of the trigger part protrudes outwardly from a rear opening end of the holder (i.e., opening provided at a rear end of the holder);

a front portion of the lancet cap protrudes outwardly from a front opening end of the holder, and a pair of parts provided at lateral sides of the front portion of the lancet cap is adjacent to a front end of the holder, or another part of the front portion of the lancet cap is adjacent to the front opening end of the holder such that a backward moving of the lancet with respect to the holder is prevented;

each of the arms of the trigger part has its front side serving as a fixed end and its rear side serving as a free end in which each of lateral sides of the lancet body is secured by abutting on the each of the arms of the trigger part such that the launching spring is kept compressed before a pricking operation; and when the trigger part is forced to move forwardly with respect to the holder upon the pushing of the trigger part for the pricking, the arms of the trigger part are expanded outwardly to cause the securing of the each lateral side of the lancet body to the each arm to be released.

When the lancet cap is removed from the lancet in the lancet pricking device of the type C, the forward pushing of the trigger part can be performed. Specifically, when an external force is applied to the pressing portion provided at the rear end of the trigger part, the trigger part can be pushed toward the inside of the holder so that the trigger part moves forwardly with respect to the holder.

In a preferred embodiment of the lancet pricking device of the type C, when the trigger part is forced to move forwardly with respect to the holder, the each arm of the trigger part (especially, the free end of the trigger part) slides on the sloped portion provided at a front-sided inner wall of the holder, and thereby the outward expansion of the each arm is automatically performed.

In another preferred embodiment of the lancet pricking device of the type C, the trigger part comprises a flexible portion (or flexible component) at a lateral face of a main body thereof; and at a point in time when the lancet still has the lancet cap (i.e., before the lancet cap is removed from the lancet), the flexible portion of the trigger part is positioned between a main body of the lancet cap and a wall of the holder. It is preferred in this embodiment that the flexible portion of the trigger part is positioned such that it is housed in a concave portion provided in the wall of the holder. According to this embodiment, even when the trigger part is intended to be pushed toward the inside of the holder due to a pressing force from the outside, the flexible portion of the trigger part abuts against both the main body of the lancet cap and the wall of the holder, whereby the pushing of the trigger part toward the inside of the holder is prevented. While on the other hand, when the trigger part is pushed toward the inside of the holder by the pressing force from the outside at a point in time after the lancet cap is removed from the lancet, the flexible portion is caused to warp, and thereby the pushing of the trigger part toward the inside of the holder can be performed.

In still another preferred embodiment of the lancet pricking device of the type C, a re-use preventing wing is provided at a front-sided outer wall face of the trigger part such that it extends backwardly and obliquely, and whereas a re-use preventing protrusion is provided at an inner wall of the holder;

upon the pushing of the trigger part in the pricking operation, the re-use preventing wing of the trigger part moves forwardly while contacting on the re-use preventing protrusion of the holder until the re-use preventing wing rides over the re-use preventing protrusion; and after the pricking operation, the re-use preventing wing is capable of abutting against the re-use preventing protrusion such that a backward movement of the trigger part is restricted, and thereby the trigger part after the pricking cannot be returned to its pre-pricking state.

The present invention also provides a lancet pricking device equipped with a suitable launching spring attachment portion. Such lancet pricking device comprises a lancet;

a launching spring;

a trigger part; and a holder for housing therein the lancet, the launching spring and the trigger part, wherein a launching spring is attached to a spring-attachment portion provided at a rear-sided inner wall of the trigger part; and the spring-attachment portion has a bent form of an elongated part (particularly, a "generally tabular part having entirely a rectangular shape") with a free end and a fixed end. For example, the spring-attachment portion has a form of hook (e.g., fishing needle form or U-like form) composed of an elongated part with a free end and a fixed end. The spring-attachment portion can facilitate the assembly of the lancet pricking device. In particular, the spring-attachment portion can contribute to an easy attachment of the launching spring to the trigger part.

The present invention provides "holder", "lancet" and "trigger part" of the pricking device described above or later, respectively. The invention also provides "pricking device kit for assembling the pricking device of the present invention, the kit including the holder, the lancet, the trigger part and the launching spring.

Effect of the Invention

The lancet pricking device of the invention is substantially composed of four parts, i.e., "lancet", "trigger part", "lancet holder" and "launching spring", and thus the structure of the device is very simple. Specifically, the lancet pricking device of the invention has a relatively simple structure wherein the lancet, the trigger part and the launching spring connected thereto are accommodated in the holder. The lancet, the trigger part and the holder (i.e., device parts other than the spring) can be simply manufactured by injection molding of resin (note that the launching spring is normally made of metal, but may be made of a resin wherein it may be, for example, resin springs such as a helical spring and a wave-like spring).

The entire size of the lancet pricking device is mainly determined by the size of the holder. Thus, a downsizing of the device parts to be housed in the holder as much as possible contributes to a small size of the holder, and thereby a compact size of the pricking device as a whole is achieved. The lancet pricking device of the present invention is excellent from the viewpoint of a transport efficiency and a storage space thereof because of its compact size. Moreover, the lancet pricking device of the present invention has such a small size to enable a holding by the fingers, and thus actually provides an improved operability.

The lancet pricking device of the invention cannot release the securing of the lancet body to the trigger part at a point in time when the pricking needle is covered with the lancet cap, and thus cannot launch the lancet. Accordingly, the lancet pricking device of the present invention can prevent the lancet from being launched accidentally and unintentionally.

Further, the lancet pricking device of the present invention has such a structure that it cannot reuse the used pricking needle, and thus is very suitable from the viewpoint of hygiene and safety. That is, the user has no choice but to use the lancet pricking device of the present invention only as a "non-reusable/disposable type device". According to the present invention, the used device will never be incorrectly reused to take a sample of the other subject's blood.

BRIEF DESCRIPTION OF THE DRAWINGS

FIGS. 1(a) and 1(b) are views of an appearance of a lancet pricking device of Type A.

FIG. 2 is views of an appearance of a lancet pricking device of Type A.

FIGS. 4(a) and 4(b) are a perspective view and a top view showing an internal structure of a lancet pricking device of Type A.

FIG. 5(a) shows a lancet of a lancet pricking device of Type A (especially, an engagement portion for securing a lancet boy is shown), and FIG. 5(b) shows a trigger part of a lancet pricking device of Type A (especially, an engaged portion of each arm for securing a lancet boy is shown).

FIGS. 6(a) and 6(b) are views of an appearance of a lancet holder used in a lancet pricking device of Type A.

FIGS. 8(a) and 8(b) are views of an appearance of a lancet used in a lancet pricking device of Type A.

FIGS. 10(a) and 10(b) are views of an appearance of a trigger part used in a lancet pricking device of Type A.

FIG. 11 is a view of an appearance of a launching spring used in a lancet pricking device of Type A.

FIGS. 12(a) and 12(b) are a perspective view and a top view showing an internal structure of a lancet pricking device of Type A at a point in time before it is put into use.

FIGS. 13(a) and 13(b) are a perspective view and a top view showing an internal structure of a lancet pricking device of Type A at a point in time after the lancet cap is removed therefrom.

FIGS. 14(a) and 14(b) are a perspective view and a top view showing an embodiment wherein a securing of a lancet body to arms of a trigger part has just been released in a lancet pricking device of Type A.

FIGS. 16(a) and 16(b) are a perspective view and a top view showing an embodiment wherein "lancet body with an exposed pricking needle" has been launched in the direction of pricking in a lancet pricking device of Type A.

FIGS. 17(a) and 17(b) are a perspective view and a top view showing an embodiment of a lancet pricking device of Type A at the time of pricking.

FIGS. 18(a) to 18(c) are views for explaining a pricking depth adjustment mechanism in a lancet pricking device of Type A.

FIGS. 22(a) to 22(c) are schematic views showing the changes of a spring attachment portion over time upon an assembly of a lancet pricking device of the present invention.

FIGS. 23(a) and 23(b) are views of an appearance of a lancet pricking device of Type B.

FIG. 35(a) schematically shows a perspective view of embodiment corresponding to that of FIG. 34(a) wherein FIGS. 35(a) to 35(f) show the series of process for pricking the region of interest using the lancet pricking device of the type B.

FIG. 35(b) schematically shows a perspective view of embodiment corresponding to that of FIG. 34(b) wherein FIGS. 35(a) to 35(f) show the series of process for pricking the region of interest using the lancet pricking device of the type B.

FIG. 35(c) schematically shows a perspective view of embodiment corresponding to that of FIG. 34(c) wherein FIGS. 35(a) to 35(f) show the series of process for pricking the region of interest using the lancet pricking device of the type B.

FIG. 35(d) schematically shows a perspective view of embodiment corresponding to that of FIG. 34(d) wherein FIGS. 35(a) to 35(f) show the series of process for pricking the region of interest using the lancet pricking device of the type B.

FIG. 35(e) schematically shows a perspective view of embodiment corresponding to that of FIG. 34(e) wherein FIGS. 35(a) to 35(f) show the series of process for pricking the region of interest using the lancet pricking device of the type B.

FIG. 35(f) schematically shows a perspective view of embodiment corresponding to that of FIG. 34(f) wherein FIGS. 35(a) to 35(f) show the series of process for pricking the region of interest using the lancet pricking device of the type B.

FIGS. 36(a) and 36(b) are views of an appearance of a lancet pricking device of Type C.

FIG. 37 is views of an appearance of a lancet pricking device of Type C.

FIG. 39(a) is a perspective view showing a holder of the lancet pricking device of Type C. FIGS. 39(b) and (c) are a perspective view and a top view of the holder of FIG. 39(a), the upper half thereof being cut away.

FIG. 40(a) is a perspective view showing a trigger part of a lancet pricking device of Type C. FIG. 40(b) is a perspective view of the back side of the trigger part of FIG. 40(a).

FIGS. 41(a) to (c) are a top view, a side view and a side cross-sectional view of a trigger part of a lancet pricking device of Type C.

FIG. 44 is a schematic view showing an embodiment of a launching spring and a spring attachment portion upon an assembling of a lancet pricking device, together with an entire assembly embodiment of the device.

FIG. 45 is a schematic view for explaining a pushing-prevention mechanism of a trigger part.

Figure 3:
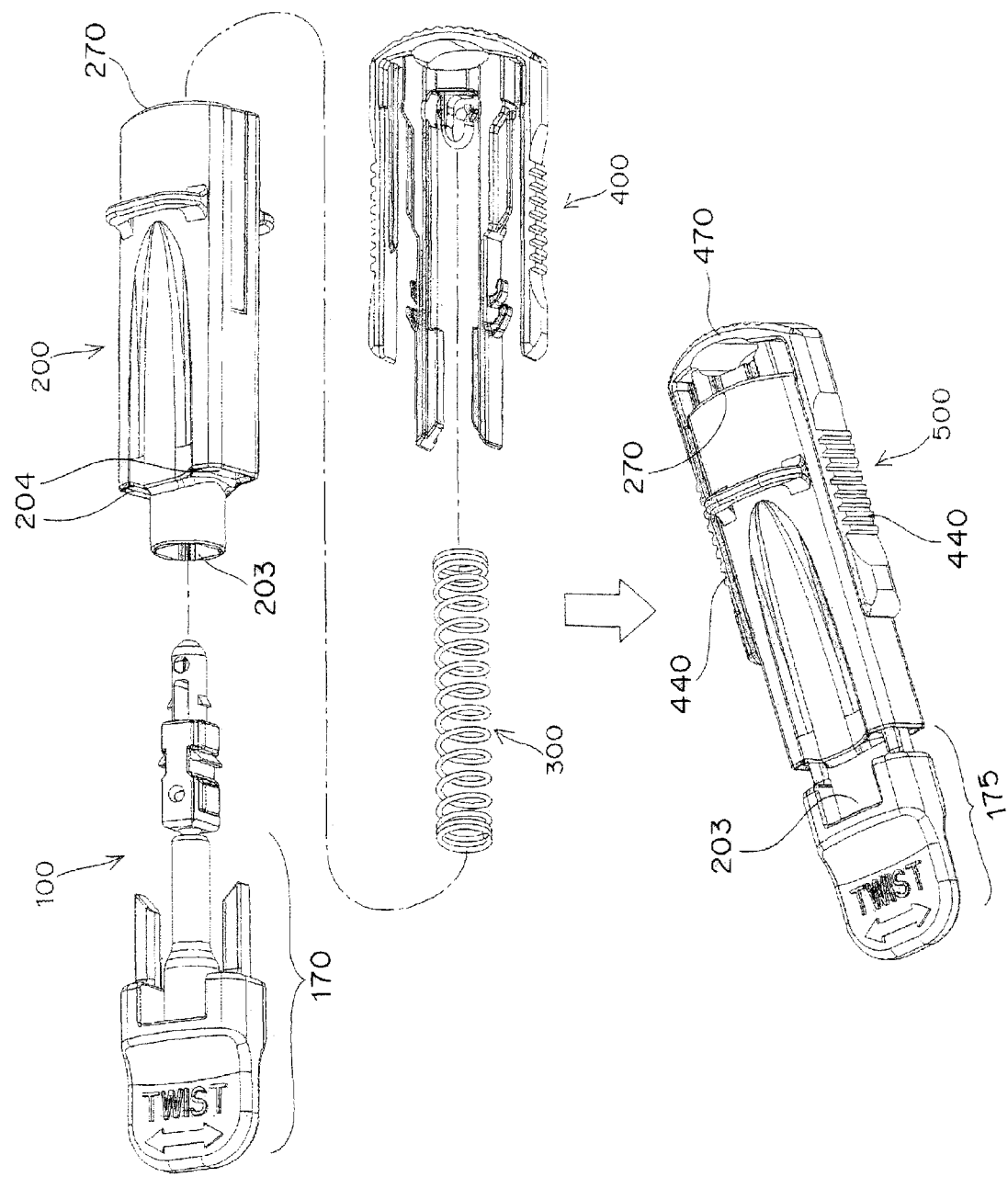
FIG. 3 shows an appearance view and an exploded perspective view of a lancet pricking device of Type A.

REFERENCE NUMERALS (Lancet Pricking Device of Type A)
100 Lancet
130 Lancet body
131 Engagement portion of lancet body (secured portion of lancet body)
133 Rear end of lancet
134 Pricking depth adjustment wing "a" provided in the lancet body
150 Pricking needle
150a Tip of pricking needle
170 Lancet cap
171 Cap arm of lancet cap
171a Tip of cap arm
175 Front portion of lancet cap
175a Pair of parts provided in front portion of lancet cap
175b Cap region (center region) between pair of parts provided in front portion of lancet cap
200 Holder (lancet holder)
203 Opening end of holder (pricking opening portion)
220 Inner wall surface of holder
222 Space generated around tip of arm of trigger part
230 Flange
250 Sloped portion provided at inner wall surface of holder
250a Sloped surface
260 Protrusion "d" provided at inner wall surface of holder
280 Protrusion
280a Front-sided face (sloped surface) of protrusion
280b Rear-sided face (pricking depth adjustment surface) of protrusion
300 Launching spring
400 Trigger part
420 Arm of trigger part (inner arm of trigger part)
420a Tip of arm
420a1 Tip surface of arm
421 Engaged portion provided in arm of trigger part (securing portion of trigger part)
423 Re-use preventing wing "c" provided in trigger part
440 Second arm of trigger part (outer arm of trigger part)
450 Fitting portion of trigger part (launching spring-attachment portion)
450a Protrusion provided in free end of spring-attachment portion
450a1 First protrusion provided in free end of spring-attachment portion
450a2 Second protrusion provided in fixed end of spring-attachment portion
455 Inner wall surface at rear end side of trigger part
460 Falling prevention wing provided in trigger part
500 Lancet pricking device of Type A
(Lancet Pricking Device of Type B)
100' Lancet
108' Weakened part
130' Lancet body
131' Engagement portion of lancet body (secured portion of lancet body)
133' Rear end of lancet
136' Front end surface of lancet body
138' Protrusion
150' Pricking needle
150a' Tip of pricking needle
170' Lancet cap
172' Rear portion of lancet cap
175' Front portion of lancet cap
175a' Pair of parts provided in front portion of lancet cap
175b' Cap region (center region) between pair of parts provided in front portion of lancet cap
200' Holder (lancet holder)
202' Front end of holder
203' Opening of holder
210' Rear end of holder
212' Space
214' Wall portion of holder
216' Opening
217' Front-sided surface (inclined surface)
218' Protrusion (convex portion)
219' Rear-sided end surface
250' Sloped portion
250a' Sloped surface of sloped portion
300' Launching spring
302' Front end portion of spring
304' Rear end portion of spring
400' Trigger part
402' Front end portion of trigger part
404' Rear portion of trigger part
406' Space of trigger part
408' Front end opening of trigger part
416' Push-back portion
420' Arm
421' Engaged portion provided in arm of trigger part (securing portion of trigger part)
422' Sliding portion
424' Re-use preventing wing
426' Falling prevention wing
432' Wall surface of trigger part
450' Hook-like spring engagement portion
450a' Protrusion
450a1' First protrusion provided in free end of spring-attachment portion
450a2' Second protrusion provided in fixed end of spring-attachment portion
480' Rear-most end portion
482' Stepped portion
500' Lancet pricking device of Type B
600' Region of interest to be pricked
(Lancet Pricking Device of Type C)
100" lancet
108" Weakened part
130" Lancet body
133" Rear end of lancet body
136" Front end surface of lancet body
138" Protrusion
150" Pricking needle
150a" Tip of pricking needle
170" Lancet cap
172" Rear portion of lancet cap (i.e., cap body)
172a" Lateral side of cap body
175" Front portion of lancet cap
175a" Pair of parts provided in front portion of lancet cap
175b" Cap region (center region) between pair of parts provided in front portion of lancet cap
131" Engagement portion of lancet body (secured portion of lancet body)
133" Rear end of lancet
200" Holder (lancet holder)
203" Front end opening of holder
217" Inclined surface
218" Protrusion (convex portion)
219" Rear-sided end surface of protrusion
250" Sloped portion of holder
250a" Sloped surface of sloped portion
270" Rear end opening of holder 290" Wall portion of holder
295" Concave portion provided in holder wall
295a" Wall surface forming the concave portion
295b" Front sloped surface of concave portion
300" Launching spring
400" Trigger part
406" Space of trigger part
420" Arm of trigger part
421" Engaged portion provided in arm of trigger part (securing portion of trigger part)
422" Sliding portion
424" Re-use preventing wing
426" Falling prevention wing
430" Lateral face of a main body
450" Fitting portion of trigger part (hook-like spring engagement portion)
450a" Protrusion
450a1" First protrusion provided in free end of spring-attachment portion
450a2" Second protrusion provided in fixed end of spring-attachment portion
451" Rear end of trigger part
470" Pressing portion at rear end of trigger part
490" Flexible portion or flexible component (tongue-like portion or component) of trigger part
500" Lancet pricking device of Type C
(Related Art)
1000 Lancet assembly
1010 Lancet
1020 Protective cover
1040 Lancet body
1050 Pricking needle
1060 Lancet cap
1080 Weakened part
1140 Front portion of Lancet assembly
1160 Rear portion of Lancet assembly
2000 Injector
2040 Plunger
2140 Front end opening of injector
2640, 2660 Tips of plunger
5140 Trigger component
5240 Projection of plunger
5260 Rear edge of trigger component
5420 Press part of trigger component

BEST MODES FOR CARRYING OUT THE INVENTION

A lancet pricking device of the invention will be described in detail below with reference to the accompanying drawings. In such description, a holder, a trigger part, a lancet and a launching spring of the lancet pricking device as well as a kit for the pricking device composed of these elements will be together described. The lancet pricking devices with the following features are categorized into and referred hereinafter to as "Type A", "Type B" and "Type C", respectively.

Type A: Each arm of the trigger part has its front side serving as a free end and its rear side serving as a fixed end, an application of the external force to the trigger part from the rear thereof causes the each arm of the trigger part to warp.

Type B: Each arm of the trigger part has its front side serving as a fixed end and its rear side serving as a free end, an application of the external force to the trigger part from the front thereof causes the each arm of the trigger part to warp.

Type C: Each arm of the trigger part has its front side serving as a fixed end and its rear side serving as a free end, an application of the external force to the trigger part from the rear thereof causes the each arm of the trigger part to warp.

First, the lancet pricking device of the "type A" will be described below. Then, the lancet pricking devices of the "type B" and "type C" will be described below in such order. It is noted that, unless otherwise specified, the contents not specific to the type can be applied to all types of the "type A", "type B" and "type C".

The term "direction" as used throughout the claims and description is defined as follows: The direction in which the pricking needle is launched for pricking is regarded as a "forward" direction. The reverse direction thereto is regarded as a "backward" direction.

The "outward" direction corresponds to a direction away from the lancet pricking device, and the reverse direction thereto (i.e., the direction toward the inside of the device) is regarded as a "inward" direction.

"Lancet Pricking Device of Type A"
<<Basic Structure of Lancet Pricking Mechanism>>
(Basic Structure)

FIGS. 1 to 3 illustrate a lancet pricking device 500 of the type A. FIGS. 1 and 2 show appearance diagrams of a lancet pricking device 500 of the type A. FIG. 3 shows an exploded diagram and a development diagram of the lancet pricking device 500 of the type A. As shown in FIG. 3, the lancet pricking device 500 of the type A according to the present invention is mainly composed of "lancet 100", "holder (particularly, lancet holder) 200", "launching spring 300" and "trigger part 400".

As shown in FIG. 4, the lancet pricking device 500 has such a structure that the lancet 100, the launching spring 300 and the trigger part 400 are housed in the lancet holder 200. Specifically, as shown in FIG. 4(a), the launching spring 300 is housed in the lancet holder 200 such that the launching spring 300 is held between the rear end of the lancet 100 and the rear end of the trigger part 400. More specifically, as shown in FIG. 4(b), one end of the launching spring 300 is attached to the rear end 133 of the lancet 100, and whereas the other end of the launching spring 300 is attached to a "fitting portion 450 provided between pair arms 420 of the trigger part 400" in the lancet holder 200. As can be seen from the comparison between FIGS. 3 and 4, the launching spring 300 inside the lancet holder 200 is in a compressed state between the "lancet 100" and the "fitting portion 450 provided between the arms 420". In other words, according to the lancet pricking device 500 of the present invention, a lancet body 130 is secured (locked) to the arms 420 of the trigger part 400 such that the launching spring 300 attached to the lancet body 130 is kept compressed (see, for example, FIG. 4(b)). See also FIGS. 5(a) and 5(b), for understanding "engagement portion 131 of the lancet body 130 (i.e., a portion of the body 130 to be in engagement with the arms)" and "engaged portion 421 provided in the arms 420 of the trigger part 400 (i.e., a portion of the each arm 420 to be in engagement with the lancet body)" associated with the securing (locking).

As can be seen from the embodiments shown in FIGS. 1, 3, and 4, particularly as for the lancet pricking device 500 of the type A, a rear end 470 of the trigger part protrudes outwardly from a rear opening end 270 of the holder 200 (i.e., an opening provided at a rear end of the holder). In the lancet pricking device 500 of the type A, a pair of outer arms 440 of the trigger part is positioned at the outer lateral surfaces of the holder 200 such that the arms 440 extend forwardly from the rear end 470 of the trigger part. Furthermore, as can be seen from the embodiments shown in FIGS. 1 and 3, a front portion 175 of a lancet cap 170 of the lancet protrudes outwardly from a front opening end 203 of the holder. In such embodiment of the lancet cap, a pair of opposed parts 175a provided at lateral sides of the front portion 175 of the lancet cap is adjacent to a front end 204 of the holder, and/or, the other parts of the front portion 175 of the lancet cap (especially, a cap center region 175b provided between the opposed parts 175a) is adjacent to the front opening end 203 of the holder (i.e., pricking opening portion of the holder). As a result, the lancet 100 is prevented from moving backwardly with respect to the holder 200.

In such lancet pricking device of the type A, when the external force is applied to the rear end 470 of the trigger part or the pair of outer arms 440 after the removal of the lancet cap from the lancet, the trigger part 400 can be pushed into the holder so that the trigger part 400 moves forwardly with respect to the holder 200.

In the following, components or parts regarding the lancet pricking device 500 of the type A will be described.

(Holder)

The holder (which can be called "lancet holder" particularly from the viewpoint of housing the lancet) 200 has, for example, a rectangular tube or box form as a whole as shown in FIG. 6. Such holder 200 has relatively small dimensions. The holder 200 can have the following dimensions (L, H, W, D) as shown in FIG. 6. For instance, a length L can be in the range of 31 to 34 mm (for example, about 32 mm), a length H can be in the range of 5 to 7 mm (for example, about 6 mm), a length W can be in the range of 8 to 11 mm (for example, about 9 mm), and a length D can be in the range of 4 to 6 mm (for example, about 5 mm). The shape of the holder 200 is not necessarily limited to the rectangular tube or box form, and thus may be, for example, a cylindrical form. The holder 200 may be formed of any kind of resin materials as long as such resin can be used for lancet in general. As shown in FIG. 6, the holder 200 has an opening 203 at its front end. The opening end 203 serves as not only a portion into which the lancet 100 can be inserted and thus set upon assembly of the pricking device, but also a portion applied to the region (e.g., finger) to be pricked at the time of pricking operation.

An inner wall surface of the holder 200 is provided with a "sloped portion" which serves to cooperate with the trigger part. The "sloped portion" is represented, for example, by reference numeral 250 in FIGS. 4(a) and 4(b). Such sloped portion 250 corresponds to a portion on which the tip of the each arm of the trigger part slides or moves while contacting. Accordingly, the sloped portion serves as causing the arm of the trigger part to warp in the pricking operation.

As shown in FIG. 6, flange portions 230 are provided at the outer surface of the holder 200 (specifically, on the outer surface at the rear side of the holder). Each flange portion 230 can be held with the fingers of the user upon the pricking operation. Thus, the flange portions 230 can facilitate a smooth pricking operation (see FIG. 7).

(Lancet)

Figure 9:
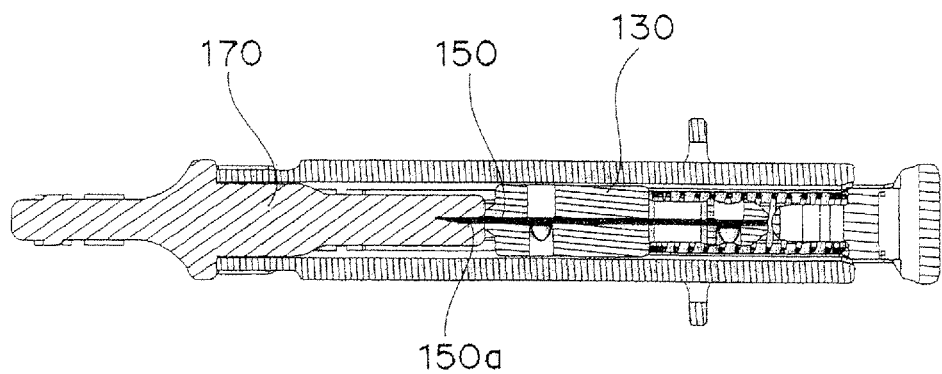
FIG. 9 is a cross-sectional view of a lancet pricking device of Type A.
Figure 15:
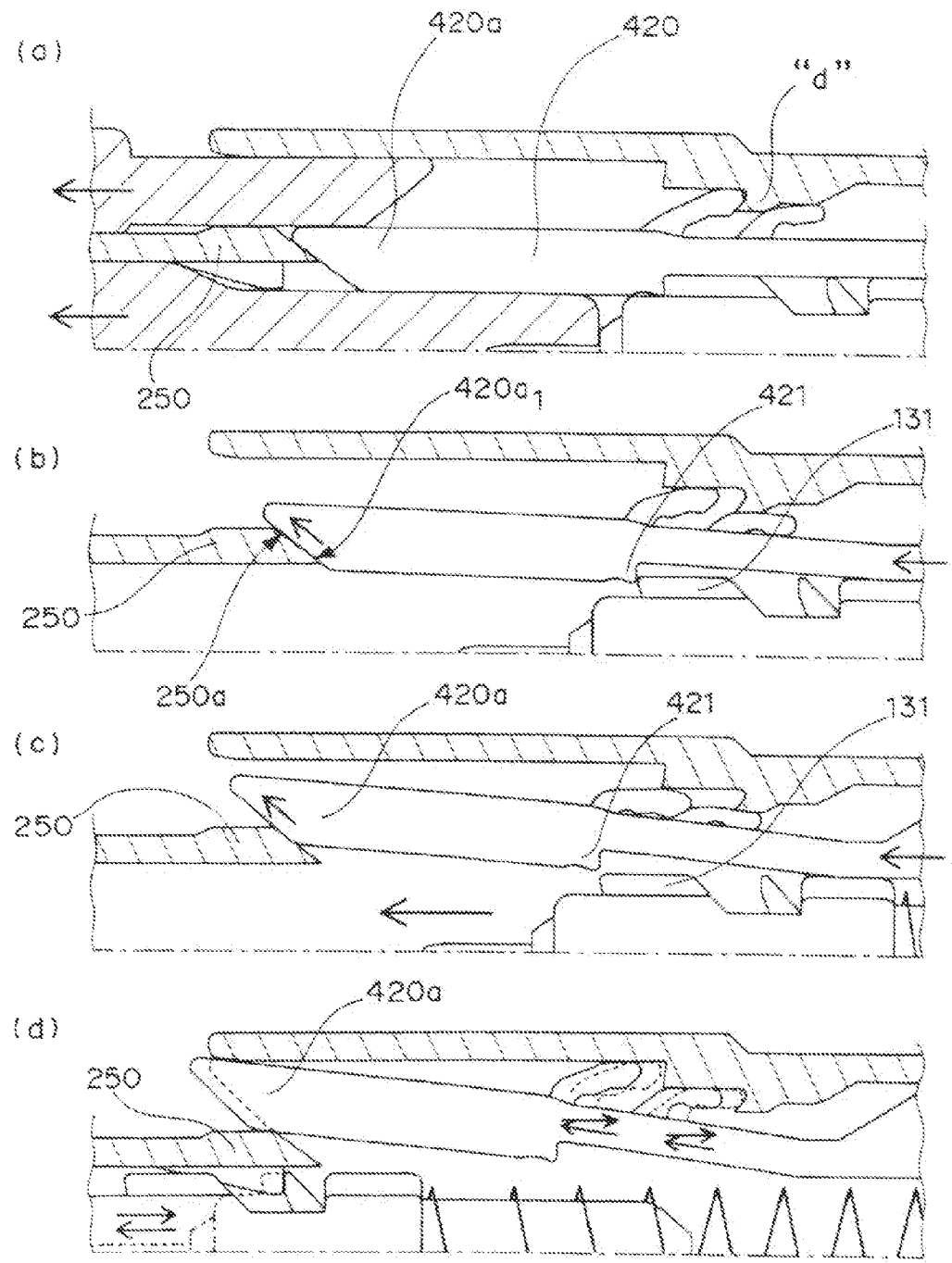
FIGS. 15(a) to 15(d) are schematic views showing the changes in a trigger arm over time upon pushing the trigger part in a lancet pricking device of Type A.

The lancet 100 used in the lancet pricking device 500 is illustrated in FIGS. 8(a) and 8(b). FIG. 8(b) illustrates the lancet 100 in different angles from each other. The lancet 100 is small, similarly to the holder 200, and is of such a size to be housed in the holder 200. The lancet 100 can have the following dimensions ($L_1$, $L_2$, $W_1$, $W_2$) as shown in FIG. 8(a). For instance, a length $L_1$ can be in the range of 36 to 38 mm (for example, about 37 mm), a length $L_2$ can be in the range of 13 to 16 mm (for example, about 14 mm), a length $W_1$ can be in the range of 8 to 11 mm (for example, about 9 mm), and a length $W_2$ can be in the range of 2 to 3 mm (for example, about 2.5 mm). As shown in FIGS. 8(a) and 8(b), the lancet 100 comprises the lancet body 130, the lancet cap 170 and the pricking needle 150 (especially, see FIG. 9 as to the pricking needle 150). The pricking needle 150 may be, for example, a metal needle. The pricking needle 150 is situated in both the resin lancet body 130 and the resin lancet cap 170 wherein the tip 150a of the pricking needle 150 is covered with the lancet cap 170, as shown in the cross-sectional view of FIG. 9. It is preferred that the lancet body 130 and the lancet cap 170 are integrally connected to each other via only a small contact portion. The lancet 100 can be formed of resin (e.g., polyethylene, polypropylene or the like) by inserting the pricking needle 150 into a die, in a so-called insert molding process. In this regard, the contact portion can be formed upon carrying out the insert molding process. Accordingly, the contact portion can be formed of the same resin as that of the lancet cap 170 and the lancet body 130. The contact portion is required to be broken upon removing the lancet cap. Thus, the contact portion can be referred to as a "weakened portion" or "easily broken portion". The contact portion may have a notch so that the contact portion can be easily broken. In some cases, the contact portion may be cut off in advance. No contact portion may also be provided in the lancet. As long as the lancet cap can be "twisted" to expose the tip 150a of the pricking needle 150 in the lancet body 130, the form of the contact portion is not limited to the specific one. The end of the front portion 175 of the lancet cap 170 is in a flat form, which can be gripped with the user's fingers and thus can then be twisted around the pricking needle (specifically, wrenched or rotated around the pricking needle). The part gripped with the fingers corresponds to a "holding portion" for user.

The lancet cap 170 comprises cap arms 171 extending backwardly. As shown in FIGS. 8(a) and 8(b), the cap arms 171 are preferably a pair of arms extending backwardly from the opposed parts 175a of the front portion 175 of the lancet cap. The cap arms 171 are preferably composed of a pair of longitudinal parts opposed to each other as shown in FIGS. 8(a) and 8(b). The respective cap arms 171 preferably extend backwardly such that they are symmetric with respect to the center axis of the lancet 100 (i.e., the axis along the longitudinal direction of the lancet 100 or pricking needle 150) as shown in these figures. It is required that the each cap arm 171 extends backwardly to reach the inside of the holder 200 when being incorporated in the holder 200 (see FIG. 4(a)). That is, in the lancet pricking device 500 of the type A, the tip of the each cap arm 171 of the lancet cap 170 is positioned within the holder 200. This arrangement can prevent the pushing of the trigger part into the holder (which will be later described in detail).

The body of the pricking needle 150 is fixed in the lancet body 130. At the time of the pricking operation, the forward launching of the lancet body 130 together with the pricking needle 150 is performed. The lateral sides of the lancet body 130 are respectively provided with an engagement portion 131 for securing the lancet to the trigger part, and also with a wing "a" (134) for adjusting a pricking depth upon pricking (see FIG. 8(a)).

(Trigger Part)

The trigger part 400 used in the lancet pricking device 500 is illustrated in FIGS. 10(a) and 10(b).

Especially, FIG. 10(b) shows the trigger part 400 in different angles from each other. The trigger part 400 is small, similarly to the holder 200 and the lancet 100, and has such a size as to be housed in the holder 200. The trigger part as shown in FIG. 10(a) can have the following dimensions ($L_3$, $L_4$, $W_3$, $W_4$, $H_1$). For instance, a length $L_3$ can be in the range of 29 to 31 mm (for example, about 30 mm), a length $L_4$ can be in the range of 22 to 24 mm (for example, about 23 mm), a length $W_3$ can be in the range of 11 to 14 mm (for example, about 12 mm), a length $W_4$ can be in the range of 6 to 9 mm (for example, about 7 mm), and a length $H_1$ can be in the range of 3 to 5 mm (for example, about 4 mm). The trigger part 400 at least comprises a pair of arms 420 which are positioned inside the holder. As shown in FIG. 10, each of the arms 420 has a free end at its front side, and a fixed end on its rear side. The trigger part 400 further has another pair of arms in addition to the arms 420. That is, the trigger part 400 preferably comprises two types of arms (420, 440), each type being composed of a pair of longitudinal arms as shown in FIGS. 10(*a*) and 10(*b*). More specifically, the trigger part 400 comprises not only a pair of arms 420 provided inside the holder, but also a pair of outer arms 440 provided at the outer surface of the lancet holder. This means that the trigger part 400 is equipped with a pair of arms 420 at its inner side, and also a pair of the second arms 440 at its outer side. Such trigger part 400 may be molded of the same resin as that of the lancet 100 (for example, polyethylene, polypropylene, or the like).

The arms 420, which are positioned inside the holder, preferably have flexibility as a whole. Particularly, it is preferred that the respective tips 420*a* of the arms 420, i.e., the free ends of the arms (see FIG. 10(*b*)) are capable of warping outwardly so as to be spaced apart from each other. Thus, the each arm 420 suitably serves to release the securing of the lancet body upon pushing the trigger part. In contrast, the second outer arms 440, which are positioned at the outer surface of the holder (in particular, the outer lateral wall surfaces of the holder), are arms to be gripped upon the pricking operation or the like, and thus do not need to have the flexibility.

The tip 420*a* of the each arms 420 positioned inside the holder preferably has a tapered shape as shown in FIG. 10(*a*). A surface 420$a_1$ of the tip 420*a* preferably has a complementary shape with respect to the surface of the sloped portion 250 of the holder 200 (see, for example, FIG. 4(*a*)). Thus, during the pushing of the trigger part, the tip 420*a* of the each arm 420 can suitably slide on the sloped portion 250 or move while being in contact with such sloped portion 250.

The each arm 420, which is positioned inside the holder, is provided with an engaged portion to which the lancet body 130 is secured at a point in time before the pricking. Specifically, as shown in FIG. 10(*a*), the engaged portion 421 in a form of protrusion is provided at an inner face of the each arm 420.

As shown in FIGS. 10(*a*) and 10(*b*), a spring attachment portion 450 for attaching the launching spring is provided between the arms 420 at the rear side of the trigger part 400. As can be seen from the position of the spring attachment portion 450, the launching spring attached to the trigger part is located inside the pair of arms 420, while being sandwiched between the arms 420.

(Launching Spring)

The launching spring 300 is shown in the perspective view in FIG. 11. The launching spring 300 serves to shoot, fire or launch the needle as suggested by its name. In other words, the launching spring 300 is one that generates an impellent force for launching the pricking needle (i.e., "lancet body with the pricking needle exposed") or a drive force for pricking. As described above, the compressed spring 300 is positioned between the "attachment portion 450 provided between the arms 420" and "lancet 100" (see FIG. 4). The launching spring 300 is preferably made of metal. For example, the spring 300 is a metallic coil spring. The size of the launching spring 300 is not limited to a specific one as long as it can be housed in the holder. The launching spring 300 may have the following dimensions ($L_5$, $D_1$) when not being compressed as shown in FIG. 11. For example, a length $L_5$ may be in the range of 15 to 20 mm (for example, about 17 mm), and a length $D_1$ may be in the range of 2.7 to 3.5 mm (for example, about 3 mm).

<<Entire Structure and Function of Lancet Pricking Device>>

(Securing of Lancet Body)

In the lancet pricking device 500 of the type A as shown in FIGS. 12(*a*) and 12(*b*), the lancet body 130 is secured to the arms 420 of the trigger part 400 such that the launching spring 300 is kept compressed. As can be seen from the embodiments shown in FIGS. 12(*a*) and 12(*b*), substantially all of the lancet body 130 and the pricking needle 150 of the lancet and the launching spring 300 are positioned inside the trigger part so as not to extend beyond the trigger part 400. In other words, the lancet pricking device 500 of the type A has such a feature that all of the lancet body 130, the pricking needle 150 and the launching spring 300 are positioned inside the pair of arms 420 of the trigger part 400 such that they do not protrude beyond the arms 420, as shown in FIGS. 12(*a*) and 12(*b*).

In the assembling of the lancet pricking device 500, the lancet 100 (or launching spring 300 attached thereto) is inserted into the front opening end 203 of the holder, and also the trigger part 400 (and launching spring 300 attached thereto) is inserted into the rear opening of the holder, and thereafter the lancet 100 is coupled to the trigger part 400 with the launching spring 300 kept compressed (see FIG. 3). The compressed launching spring gives a backward force with respect to the trigger part 400. However, falling prevention wings 460 of the trigger part 400 abut against protrusions "d" (or convex portions "d") (260) provided at the inner wall surface of the lancet holder (see FIG. 12(*b*)), and thereby the trigger part is prevented from coming off or falling from the holder.

That is, it can be regarded that the lancet body 130 is secured to the arms 420 of the trigger part due to an abutment between "wings 460 of the trigger part 400" and "protrusions "d" (260) provided at the inner wall surface of the lancet holder" and an abutment between "engagement portions 131 of the lancet body 130" and "engaged portions 421 of the arms 420 of the trigger part 400", as shown in the embodiment of FIG. 12(*b*). In the lancet holder 200, the forward force attributed to the compressed launching spring 300 acts on the lancet 100, and thereby the lancet 100 is forced to forwardly move. However, the forward movement of the lancet body 130 is locked by the abutting of the engagement part 131 of the lancet body 130 against the engaged part 421 of the each arm 420 of the trigger part 400. It should be noted that the lancet body 130 is locked or secured to the trigger part 400, whereas the lancet cap 170 is not locked or secured to the trigger part 400, and thereby the lancet cap 170 can be removed prior to the pricking operation.

Upon the assembling of the lancet pricking device, the launching spring 300 is attached to the trigger part 400. In this regard, the spring attachment portion 450 of the trigger part can suitably work. Specifically, in a case where the spring attachment portion 450 is comprised of a bent elongated part having a free end and a fixed end as shown in FIGS. 10 and 22, the assembling of the lancet pricking device (in particular, attaching of the launching spring 300) is effectively facilitated. That is, as shown in FIGS. 10 and 22, in a case where the spring attachment portion 450 is provided in the form of a hook (e.g., fishing-needle form or U-like form), the inward warping of the spring attachment portion 450 can be easily performed (see FIGS. 22(*a*) and 22(*b*)), so that the engagement of the launching spring coil with the attachment portion of the trigger part can be effectively facilitated. It is preferred that the spring attachment portion 450 has a protrusion 450*a* that protrudes outwardly. In particular, a first protrusion $450a_1$ is preferably provided at the free end of the bent elongated part, whereas a second protrusion $450a_2$ is preferably provided at the fixed end of the bent elongated part as shown in FIG. 22(a). In this case, once the spring 300 increases its coil diameter to ride over the protrusions 450a, then the spring 300 is returned to have its original coil diameter. As a result, a joint between the spring 300 and the spring attachment portion 450 cannot be easily released any longer (see FIGS. 22(a) to 22(c)).

At a point in time after the assembling of the lancet pricking device is completed, the cap arms of the lancet are positioned within the holder 200. Specifically, as shown in FIG. 12, when the tip of the pricking needle is covered with the lancet cap 170, a tip 171a of the each cap arm 171 of the lancet cap is positioned within the holder 200. Specifically, as shown in FIG. 12(b), the tip 171a of each of the cap arms 171 is positioned along and near the inner wall of the lancet holder. More specifically, the tip 171a of the each cap arm 171 reaches and extends through a space formed between "inner wall surface 220 of the holder" and "sloped portion 250 of the holder". This makes it possible that the tip 420a of the each arm 420 of the trigger part 400 is positioned between the "tip 171a of the cap arm 171 of the lancet cap 170" and the "sloped portion 250 of the holder" as shown in FIG. 12, which prevents the pushing of the trigger part into the holder. That is, even when the trigger part 400 is intended to be pushed into the lancet holder by the pressing force from the outside, the tip 420a of the each arm 420 of the trigger part 400 abuts against both the tip 171a of the each cap arm 171 of the lancet cap 170 (more specifically, lateral face of the tip of the each cap arm) and the sloped portion 250 (more specifically, a sloped surface of the sloped portion), and thereby the trigger part 400 is prevented from being pushed into the lancet holder. On the other hand, after the lancet cap is removed as shown in FIG. 13, the cap arms are also eliminated to thereby generate a space around the tip 420a of the each arm 420 of the trigger part 400 (see the "space" represented by reference numeral 222 in FIG. 13(b)). Thus, when the trigger part 400 is pushed forwardly toward the inside of the holder, the tip 420a of the each arm 420 of the trigger part can move into the space while warping. As a result, the securing of the "engagement portion 131 of the lancet body 130" to the "engaged portion 421 of the each arm 420 of the trigger part 400" is released (see FIGS. 14(a) and 14(b)). A sloped angle α of the sloped portion 250 (see FIG. 13(a)) is preferably in the range of 10° to 50°, more preferably in the range of about 20° to 40°.

The warping of the each arm 420 of the trigger part 400 is performed as shown in FIGS. 15(a) to 15(d) which illustrate the changes of the each arm over time. Specifically, the tip surface $420a_1$ of the each arm 420 of the trigger part slides on the sloped surface 250a of the sloped portion 250 of the holder or move while contacting the sloped surface 250a. Preferably, the arms 420 of the pair are automatically expanded outwardly such that the respective tips 420a of the arms 420 are spaced apart outwardly from each other. Such warping ensures the releasing of the securing of the "engagement portion 131 of the lancet body 130" to the "engaged portion 421 of the each arm 420 of the trigger part 400" (see FIG. 14). Such releasing causes the compressed spring 300 to expand, and thereby forcing "lancet body with the pricking needle exposed" to be launched in the pricking direction (see FIGS. 16 and 17).

(Pricking Depth Adjustment Mechanism)

The lancet pricking device 500 of the present invention preferably has a pricking depth adjustment mechanism. Specifically, as shown in FIG. 18, the wing "a" (134) for adjustment of the pricking depth is provided in the lancet body 130, whereas the projection "b" (260) for adjustment of the pricking depth is provided in the holder 200. As shown in FIGS. 18(a) to 18(c), the wing "a" (134) of the lancet body makes contact with or hits the projection "b" (260) of the holder upon the pricking operation, whereby the length of the pricking needle exposed from the open end of the lancet holder is defined or limited (see the reference numeral "$L_6$" of FIG. 18(b) for understanding of the "length of the pricking needle exposed from the open end"). That is, the collision between the wing "a" (134) and the projection "b" (260) restricts the forward movement of the pricking needle, making it possible to define the pricking depth (specifically, the length of the pricking needle protruding from the opening end 203 of the holder). Thus, the "pricking depth" can be adjusted by appropriately changing the "set position of the wing "a" (134) of the lancet body 130" and/or the "set position of the projection "b" (260) of the holder 200". It is preferred that the protrusion "b" (260) of the holder 200 is formed integrally with the sloped portion 250.

(Re-use Preventing Mechanism)

Figure 19:
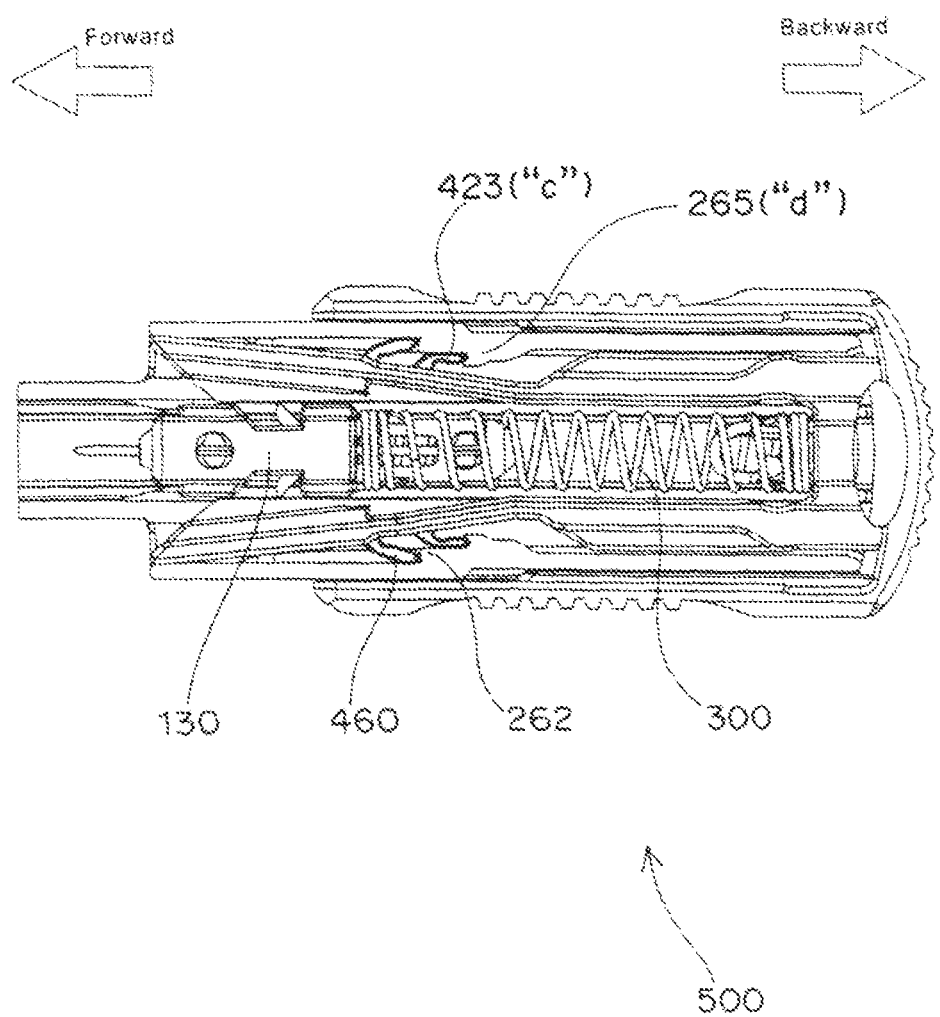
FIG. 19 is a top view for explaining a re-use preventing mechanism in a lancet pricking device of Type A.

The lancet pricking device 500 of the present invention preferably has a re-use preventing mechanism. FIG. 19 shows an embodiment of the lancet pricking device 500 at a point in time after the pricking operation. Main components or parts contributing to the re-use preventing mechanism are "reuse preventing wings "c" (423) provided on the outer face of the arms (420) of the trigger part 400" and "re-use preventing protrusions "d" (or convex portions "d") (260) provided at the inner wall of the holder". As can been seen from the embodiment in FIG. 19, even if the lancet body 130 is forced to be moved backward in order to obtain the compressed state of the launching spring 300 again after the pricking operation, the wings "c" (423) of the trigger part 400 coupled to the lancet body 130 make contact with the protrusions "d" (260) of the holder. As a result, the trigger part 400 cannot be moved backward any more due to the contacting of the wings "c" with the protrusions "d", which restricts the backward movement of the trigger part 400. That is, the used pricking device cannot be returned to its original state of pre-pricking. This prevents a re-use of the pricking needle, which is very desirable from the viewpoint of hygiene and safety. The lancet pricking device of the present invention having this kind of re-use preventing mechanism can be referred to as a "single use device". As can be seen from the embodiment shown in FIG. 19, "wings 460 of the trigger part 400" serving to prevent the falling of the trigger part before the pricking also make contact with "stepped portions 262 provided at the inner wall of the holder" to prevent the backward movement of the lancet body, which assists the re-use preventing function.

<<Embodiment of Use of Pricking Device>>

Figure 20:
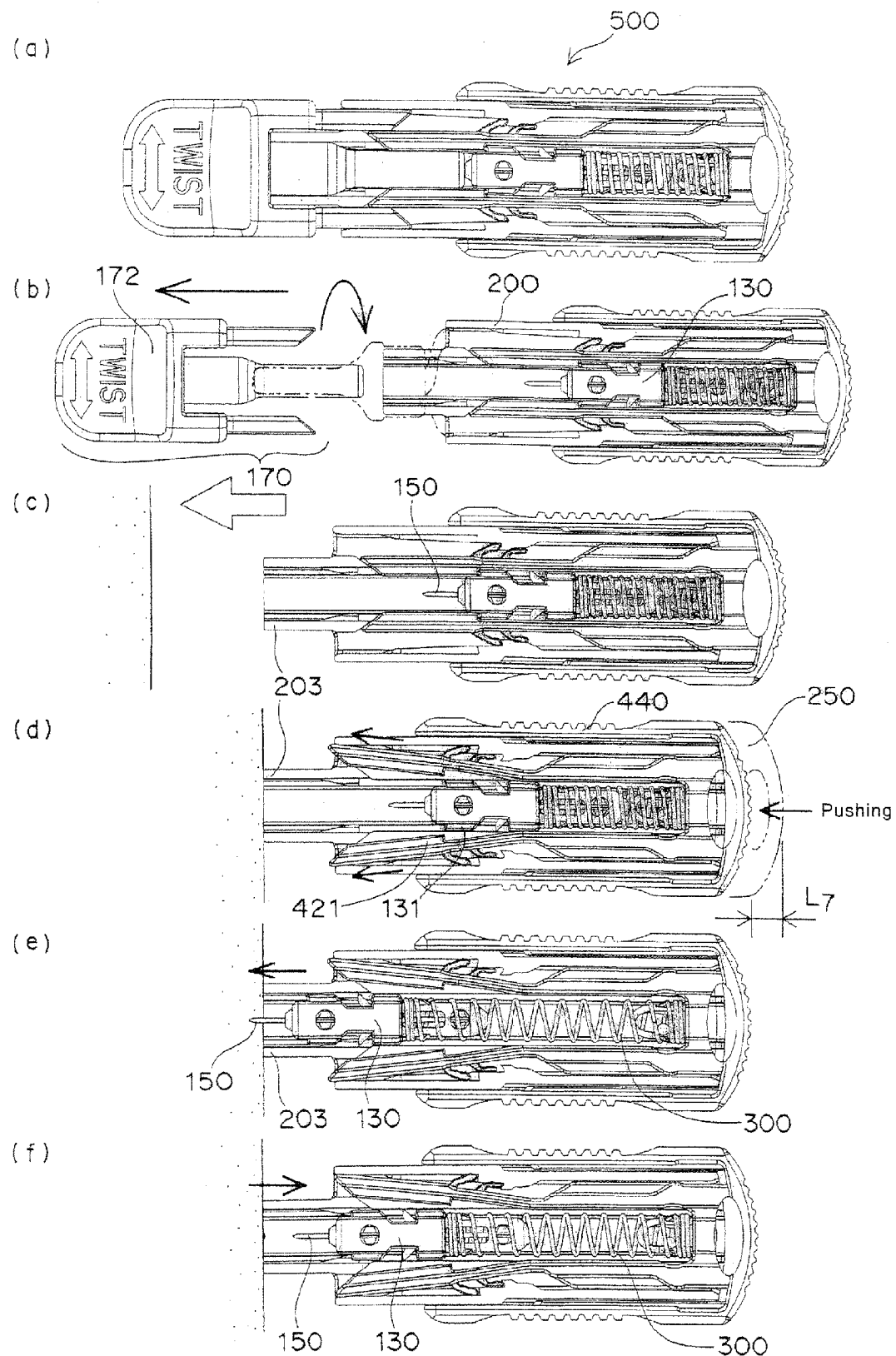
FIGS. 20(a) to 20(f) are top views schematically showing the changes in a lancet pricking device of Type A over time in its use.
Figure 21:
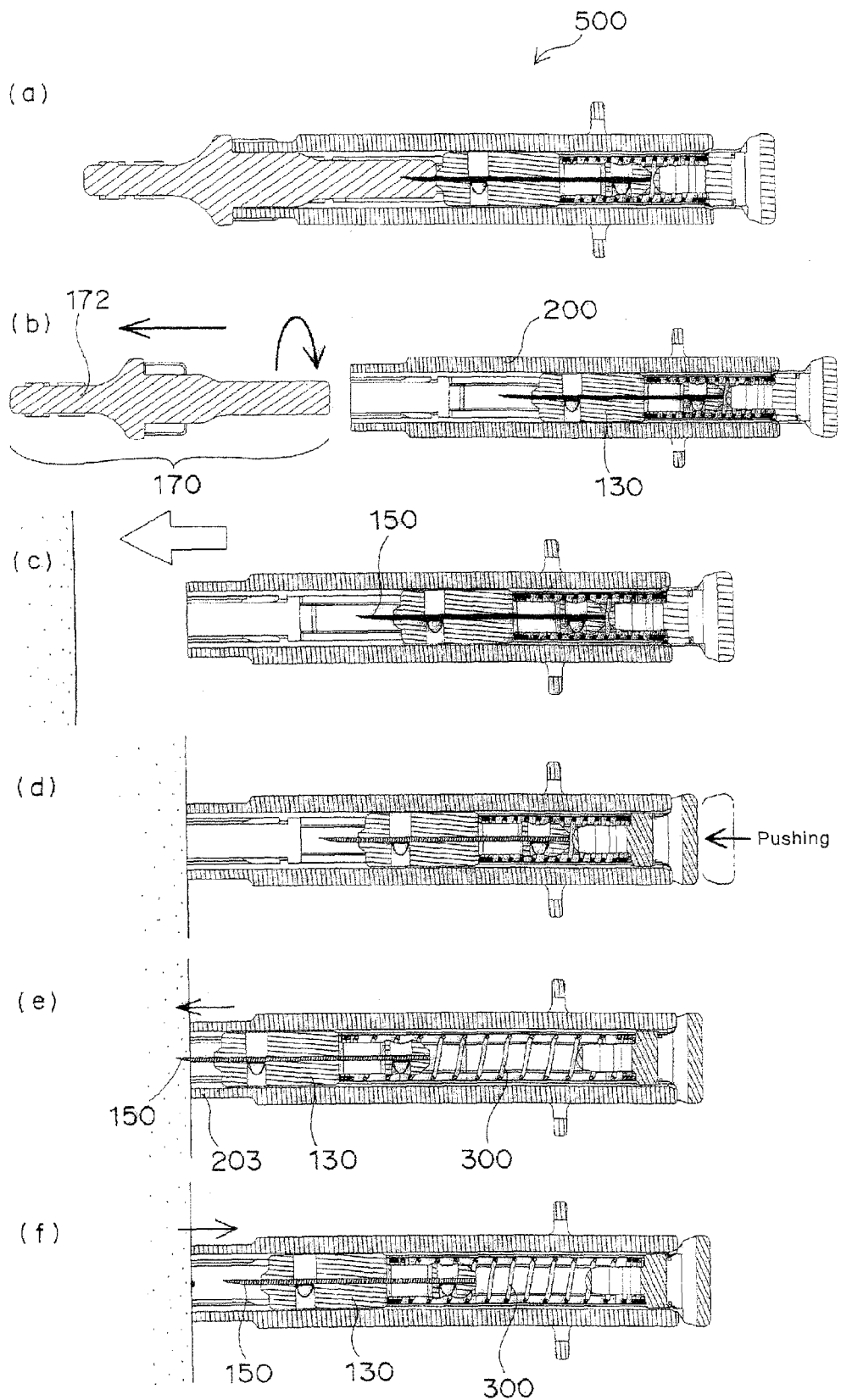
FIGS. 21(a) to 21(f) are cross-sectional side views schematically showing the changes in a lancet pricking device of Type A over time in its use.

In the following, the embodiments of use of the lancet pricking device according to the invention will be described. FIGS. 20 (a) to (f) or FIGS. 21 (a) to (f) show the changes of the lancet pricking device 500 over time in numerical order. It is noted that the figures indicated by the same alphabet among FIGS. 20(a) to 20(f) and FIGS. 21(a) to 21(f) respectively show the same state.

The lancet pricking device 500 of the present invention at a point in time before the pricking operation is shown in FIGS. 20(a) and 21(a). First, the lancet cap 170 is removed from the lancet 100 as shown in FIGS. 20(b) and 21(b). The removal of the lancet cap 170 is performed preferably by twisting the lancet cap 170. Specifically, as shown in FIGS. 20(b) and 21(b), the lancet cap 170 (in particular, the holding portion 172) is rotated to break the "contact provided between the lancet body 130 and the lancet cap 170", and thereafter the lancet cap 170 is pulled out forwardly. In other words, one hand holds the lancet holder 200 from the outside, and the fingers of the other hand pull the holding portion 172 of the lancet cap 170 while twisting it. As a result, the pricking needle 150 is exposed in the lancet body 130 within the lancet holder 200 (see FIGS. 20(c) and 21(c)). Then, after the opening end 203 of the lancet holder 200 is applied to the predetermined region to be pricked (e.g., a fingertip), the trigger part 400 is pushed toward the inside of the holder (see FIGS. 20(d) and 21(d)). The pushing of the trigger part may be performed by pressing the rear end of the trigger part forwardly with the holder 200 held. Alternatively, while the second outer arms 440 of the trigger part provided at the outer faces of the holder are gripped with the fingers, the pricking device is pressed against the "predetermined region to be pricked" (This operation may be similar to a "stamping" operation). The pushing of the trigger part 400 causes the tip of the each inner arm 420 of the trigger part to slide on the sloped portion, and thereby the outward warping of the inner arms 420 is performed. As a result, the securing of the engagement portion 131 of the lancet body to the engaged portion 421 of the each arm 420 is released (note that FIGS. 20(d) and 21(d)) illustrate the embodiment at the time of such releasing). That is, the securing of the lancet body to the arms 420 of the trigger part 400 is released by the pushing of the trigger part. When the securing of the lancet body is released, the compressed spring 300 is expanded to launch the lancet body 130 with the exposed pricking needle 150 in the pricking direction. After the launching, the pricking needle 150 of the lancet body 130 moving in the pricking direction protrudes from the opening end 203 of the lancet holder, whereby the predetermined region which is in contact with the opening end 203 is pricked (see FIGS. 20(e) and 21(e)). Upon the pricking, the expanded spring 300 is returned to its original shape, and thereby the pricking needle 150 is quickly retracted. Specifically, since the "lancet body 130 with the pricking needle 150 exposed" has the spring 300 thereto, the lancet body 130 goes back such that it is pulled by the spring, and finally the pricking needle 150 is retracted into the holder 200. The state of the pricking needle at a point in time after the pricking operation is shown in FIGS. 20(f) and 21(f).

Finally, the pushing of the trigger part will be additionally described below. As mentioned above, the pricking device of the present invention can perform the pricking operation by pressing the rear end of the trigger part forwardly while holding the holder with fingers. Alternatively, the pricking device of the present invention can perform the pricking operation by pressing the pricking device against the "predetermined region to be pricked" with the second outer arms of the trigger part gripped with the fingers. More specifically, the following three "pressing embodiments" can be provided upon the pricking device of the present invention is put into use, and thus the invention has a superior operability.

Figure 7:
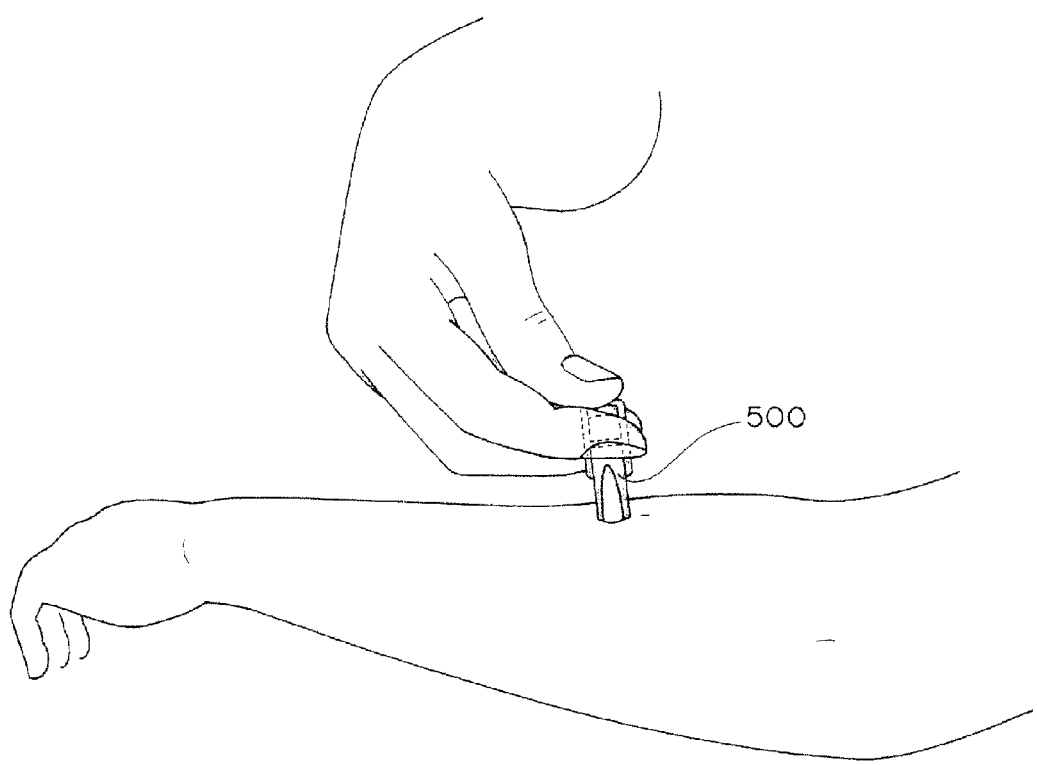
FIG. 7 is a schematic view showing an embodiment wherein a pricking operation is performed by the user.

(1) The rear end 470 of the trigger part is pressed with the thumb while holding the flange portions 230 with the index finger and the middle finger (see FIGS. 1 and 7).
(2) The rear end 470 of the trigger part is pressed with the index finger while holding the flange portions with the thumb and the middle finger.
(3) The pricking device is pressed against the "predetermined region to be pricked" while gripping the second outer arms 440 of the trigger part with the thumb and the index finger (that is, the stamping operation is performed).

In this way, there is provided many forms of "pushing operation". This is partially due to a relatively short pushing stroke of the trigger part. In this regard, as shown in FIG. 20(d), a stroke length $L_7$ is in the range of about 3 to 7 mm, for example.

"Lancet Pricking Device of Type B"
<<Basic Structure of Lancet Pricking Mechanism>>
(Basic Structure)

Figure 24:
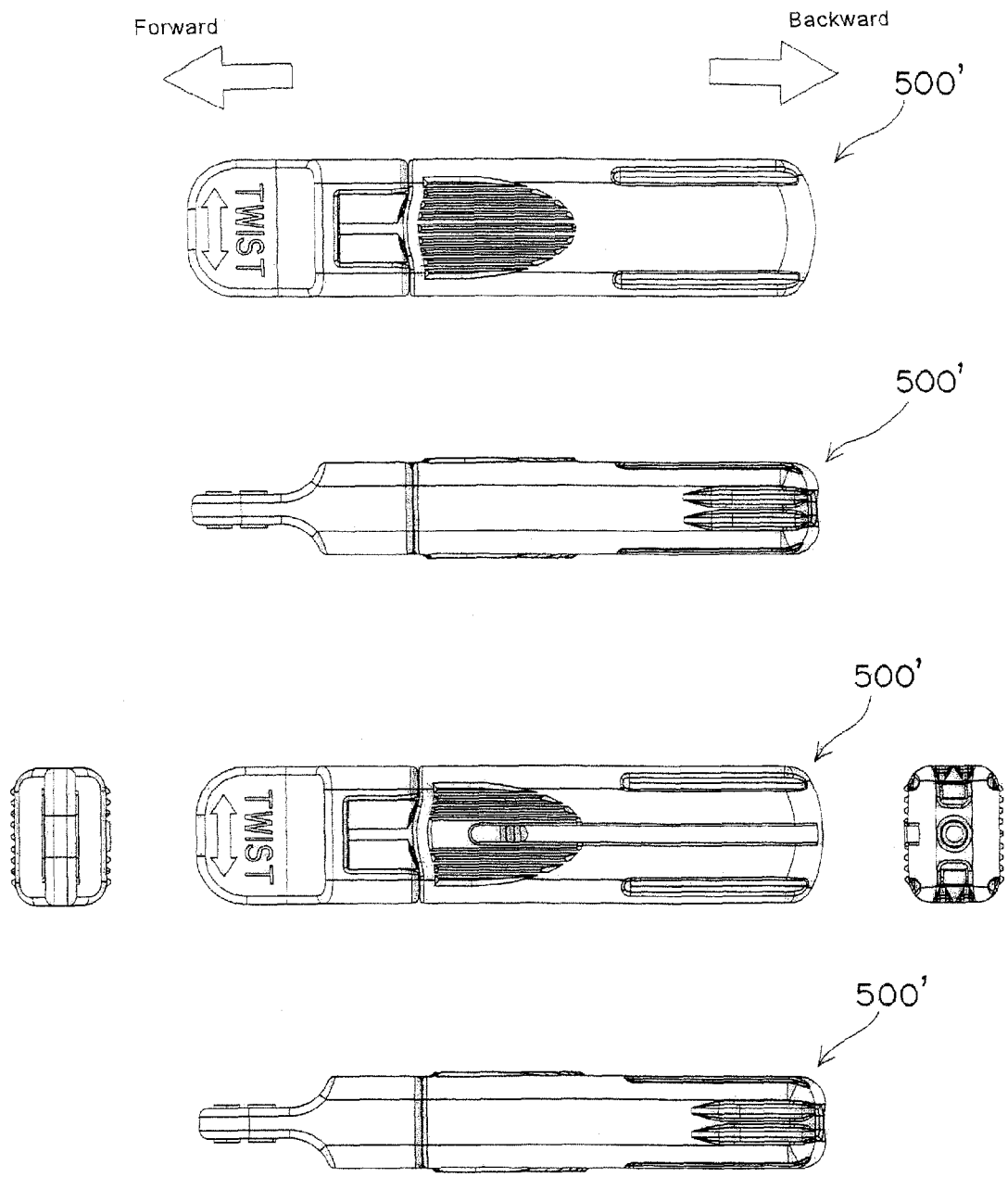
FIG. 24 is views of an appearance of a lancet pricking device of Type B.
Figure 25:
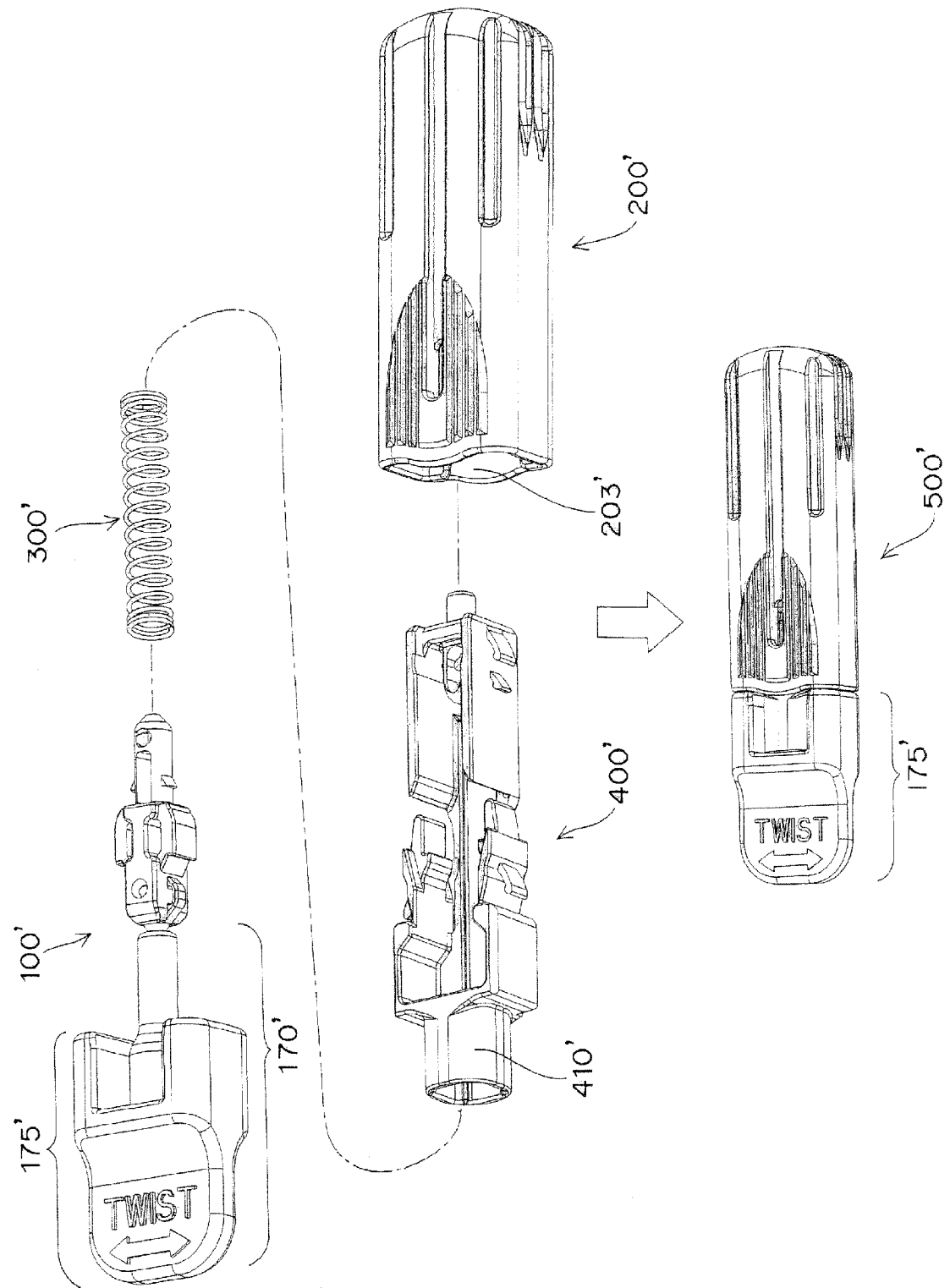
FIG. 25 shows an appearance view and an exploded perspective view of a lancet pricking device of Type B.
Figure 26:
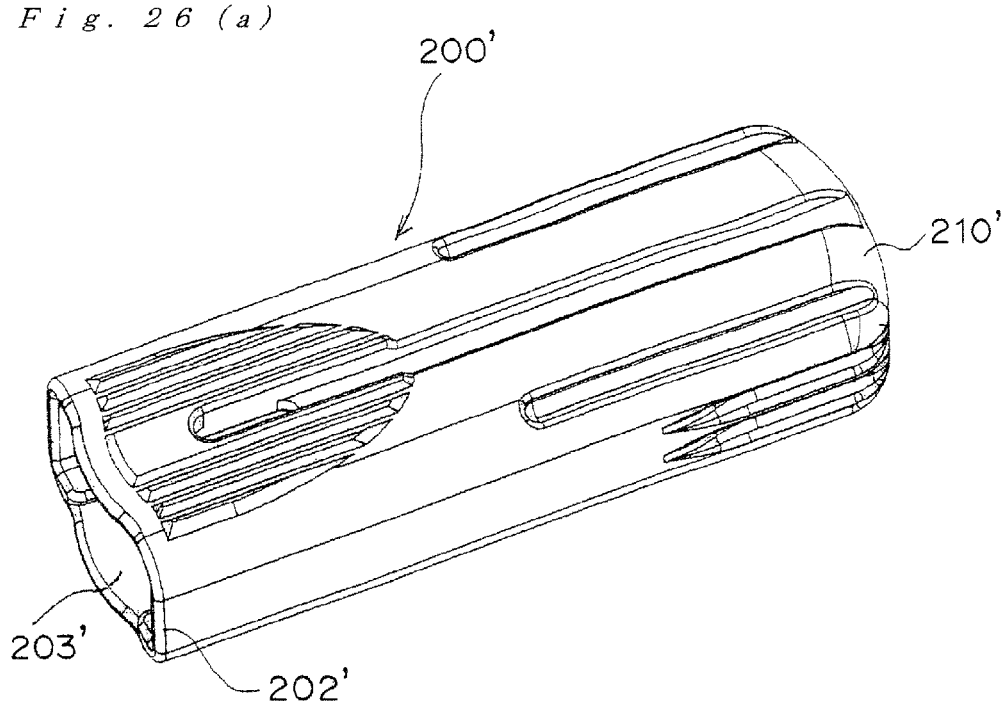
FIG. 26(a) is a perspective view showing a holder of a lancet pricking device of Type B.
FIG. 26(b) is a perspective view showing the holder of the lancet pricking device of Type B, the upper half thereof shown in FIG. 26(a) being cut away.
FIG. 26(c) is a top view showing the holder of the lancet pricking device of Type B, the upper half thereof shown in FIG. 26(a) being cut away.
Figure 26:
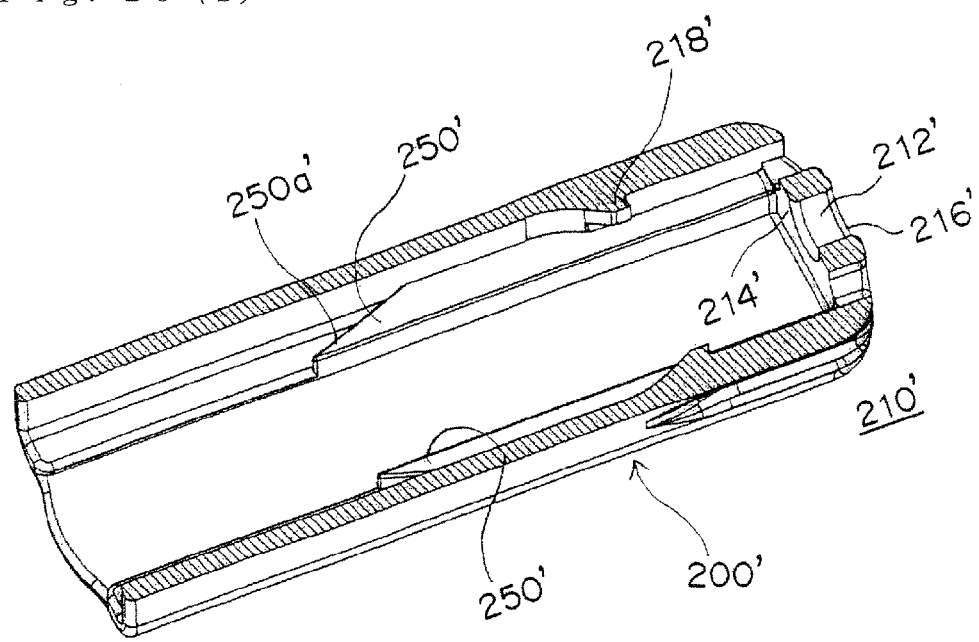
Figure 26:
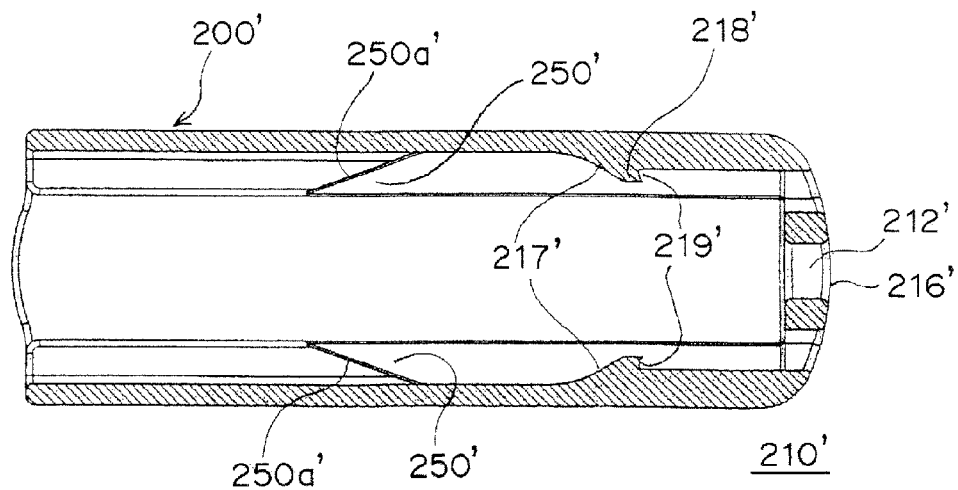
Figure 27:
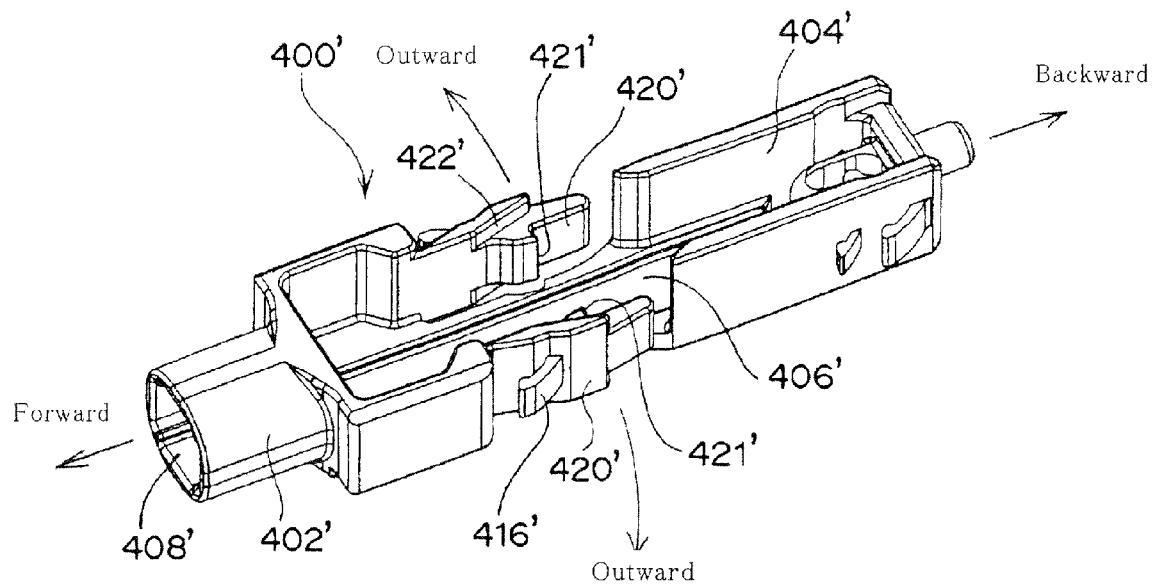
FIG. 27(a) is a perspective view showing a trigger part of a lancet pricking device of Type B.
FIG. 27(b) is a top view showing a trigger part of a lancet pricking device of Type B.
Figure 27:
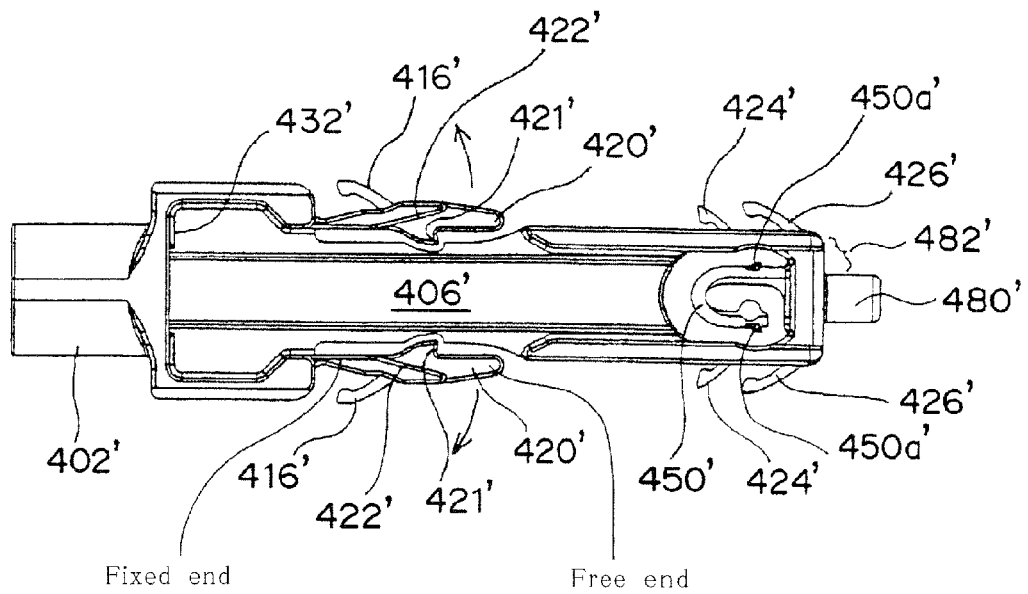
Figure 28:
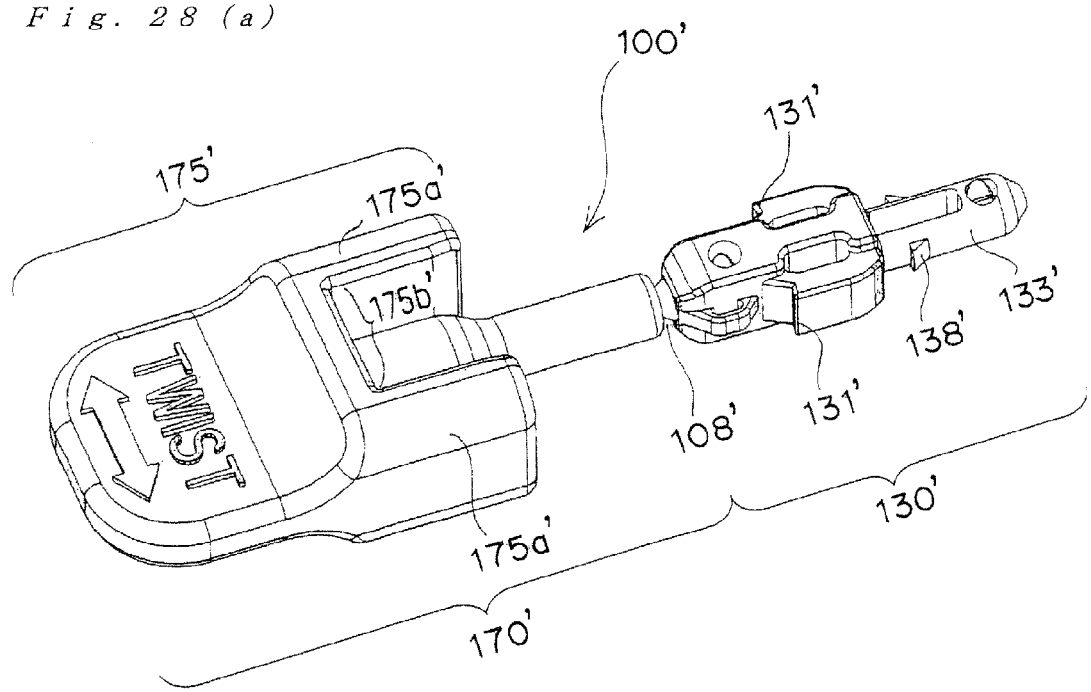
FIG. 28(a) is a perspective view showing a lancet of a lancet pricking device of Type B.
FIG. 28(b) is a top view showing a lancet of a lancet pricking device of Type B.
Figure 28:
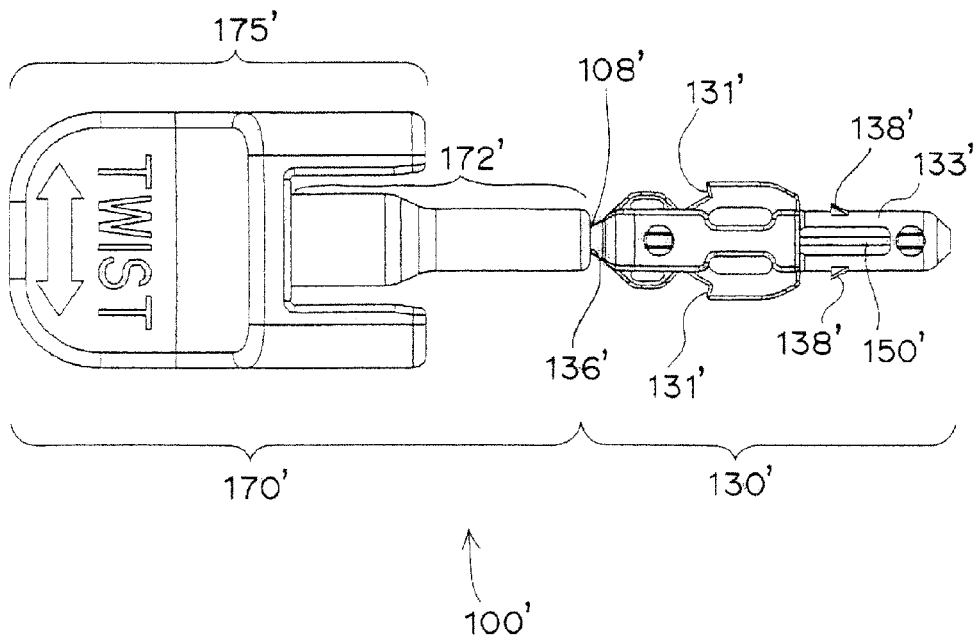

FIGS. 23 to 25 show a lancet pricking device 500' of the type B. FIGS. 23 and 24 show appearance diagrams of the lancet pricking device 500' of the type B. FIG. 25 shows an exploded view and a development view of the lancet pricking device 500' of the type B. As shown in FIG. 25, the lancet pricking device 500' of the present invention is mainly composed of "lancet 100'", "launching spring 300'", "trigger part 400'" and "holder (particularly, lancet holder) 200'". Furthermore, FIG. 26 shows the holder 200' of the lancet pricking device of the type B. FIG. 27 shows the trigger part 400' of the lancet pricking device of the type B. FIG. 28 shows the lancet 100' of the lancet pricking device of the type B.

Figure 29:
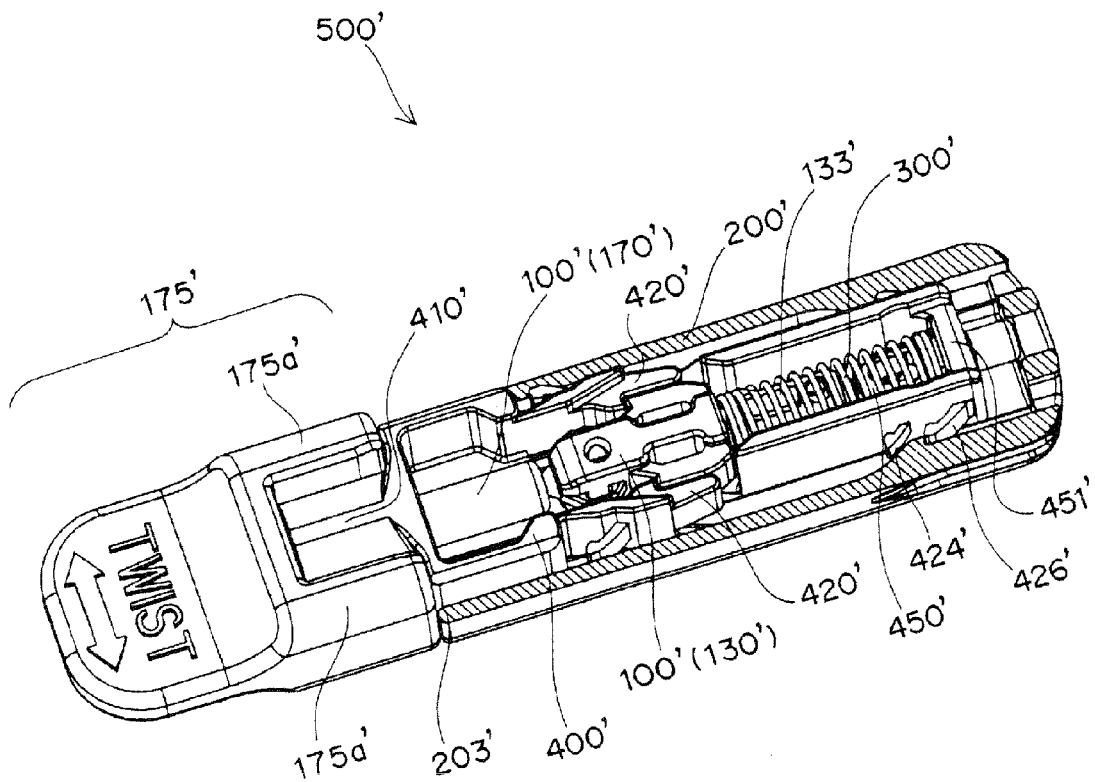
FIG. 29 is a perspective view showing an internal structure of a lancet pricking device of Type B at a point in time before it is put into use.

FIG. 29 shows the lancet pricking device 500' with the upper half of the holder 200' cut away therefrom. As shown in FIG. 29, the lancet pricking device 500' has such a structure that the lancet 100', the launching spring 300' and the trigger part 400' are housed in the lancet holder 200'. Specifically, as shown in FIG. 29, the launching spring 300' is housed in the lancet holder 200' such that the launching spring 300' is held between the rear end of the lancet 100' and a rear end 451' of the trigger part 400'. More specifically, as shown in FIG. 29, one end of the launching spring 300' is attached to the rear end 133' of the lancet 100', and whereas the other end of the launching spring 300' is attached to a "fitting portion 450' of the trigger part 400'" in the lancet holder 200'. As can be seen from the comparison between FIGS. 25 and 29, the launching spring 300' inside the lancet holder 200' is in a compressed state between the "lancet 100'" and the "fitting portion 450' provided at the rear end of the trigger part 400'". In other words, in the lancet pricking device 500' of the present invention, a lancet body 130' is secured (locked) to arms 420' of the trigger part 400' such that the launching spring 300' attached to the lancet body 130' is kept compressed (see, for example, FIG. 29). See also FIGS. 27(a) and 27(b) for understanding "engagement portion 131' of the lancet body 130'", and "engaged portion 421' provided in the arm 420' of the trigger part 400'" associated with the securing (locking).

As can be seen from the embodiments shown in FIGS. 23, 25, and 29, the lancet pricking device 500' of the type B has such a feature that the trigger part 400' is disposed as a whole within the holder 200' such that only the pricking opening portion 410' provided at the front end of the trigger part 400' protrudes outwardly from the front opening end 203' of the holder 200' (an opening provided at a front end of the holder). Further, as can be seen from the embodiments shown in FIGS. 23 and 29, a front portion 175' of a lancet cap 170' protrudes outwardly from the front opening end 203' of the holder. In such embodiment of the lancet cap, a pair of parts 175a' provided at lateral sides of the front portion 175' of the lancet cap is adjacent to the front opening end 203' of the holder, so that the lancet 100' is prevented from moving backward with respect to the holder 200'.

After the lancet cap is removed from the lancet in the lancet pricking device of the type B, the trigger part can be pushed backwardly. Specifically, when the external force is applied to the pricking opening portion 410' provided at the front end of the trigger part 400' after the removal of the cap, the trigger part can be pushed into the holder so that the trigger part 400' moves forwardly with respect to the holder 200'.

Figure 30:
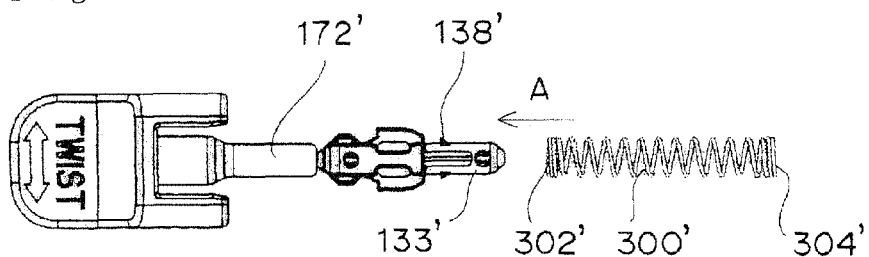
FIG. 30 schematically shows an embodiment wherein a launching spring is attached to a lancet in a lancet pricking device of Type B, in which the top view thereof is shown.
Figure 31:
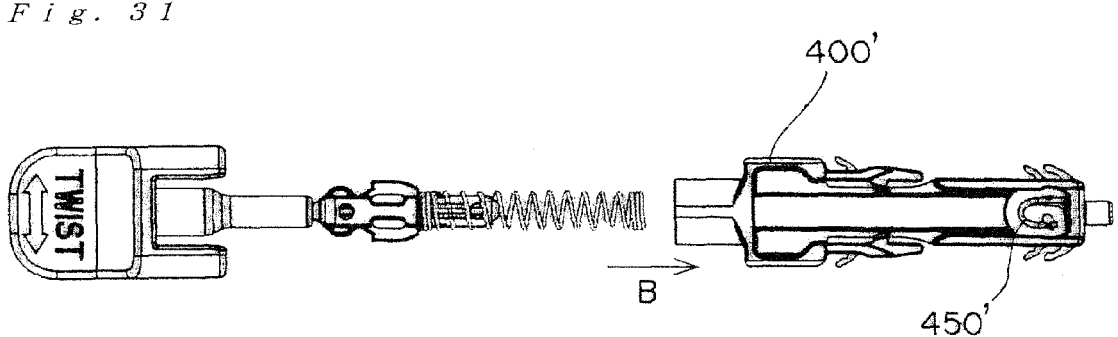
FIG. 31 schematically shows an embodiment wherein a launching spring attached to a lancet is then attached to a trigger part in a lancet pricking device of Type B, in which the top view thereof is shown.

Upon assembling of the lancet pricking device of the type B, first, as indicated by the arrow "A" in FIG. 30, a front end 302' of the launching spring 300' is coupled to a rear part of the lancet 100' to form the state shown in FIG. 31. Then, a rear end 304' of the launching spring 300' in this state is coupled to a rear end portion of the trigger part 400' as indicated by the arrow "B" of FIG. 31 to form the state shown in FIG. 32. That is, the launching spring is compressed, so that the arms of the trigger part are brought into a preliminary assembly state in which the arms of the trigger part are in engagement with the lateral sides of the lancet body. Thereafter, the preliminary assembly of the trigger part, the lancet and the launching spring coupled thereto is inserted into the inside space of the holder 200' while exposing the front portion of the lancet, as indicated by the arrow "C" of FIG. 32. In this way, the assembling (that is, assembling) of the pricking device of the present invention is completed. The pricking device of the present invention thus assembled is schematically shown in the perspective view in FIG. 33.

In the following, components or parts regarding the lancet pricking device 500' of the type B will be described.
(Holder)
FIG. 26 schematically shows a preferred embodiment of the holder 200' of the pricking device of the type B. As shown in FIG. 26, the holder 200' has a cylindrical shape as a whole, and has a substantially rectangular cross-section perpendicular to the pricking direction. A front end 202' of the holder has an opening 203', into which the preliminary assembly of the trigger part, the lancet and the launching spring can be inserted.

As shown in FIGS. 26(b) and 26(c), the inner walls of the lateral sides of the holder 200' are respectively provided with sloped portions 250'. The sloped portion 250' has a sloped surface 250a' which is inclined toward the center of the holder (i.e., toward the inward) in the forward direction. In the embodiment shown in FIGS. 26(b) and 26(c), the sloped portions are provided at upper lateral side and lower lateral side of the holder (note that only the sloped surface provided at the lower lateral side is shown). As mentioned later, a part of the each arm of the trigger part slides on the sloped surface 250a' or move while contacting the surface 250a'. Specifically, when the trigger part 400' is forced to move backwardly with respect to the holder 200', the free end of the each arm 420' slides on the sloped surface 250a or moves on the sloped surface 250a under friction against the surface 250a in the direction from the front toward the rear. As a result, the outward expansion of the arms is automatically performed.

The holder 200' has a space 212' opened at its rear end 210'. After using the pricking device, the rear-most end of the trigger part is fitted into the space 212', and a trigger part's stepped portion for defining the rear-most end of the trigger part makes contact with a wall portion 214' for defining the space 212'. In such state, the end surface of the rear-most end of the trigger part can be preferably seen from an opening 216' for defining the space. Preferably, the opening 216' can be substantially or almost flush with the end surface of the trigger part. That is, by the end surface of the trigger part viewed from the opening 216', it is easy to determine whether the pricking device is already used or not.

The holder 200' has protrusions (convex portions) 218' at the rear of the sloped portions 250'. As described later, the protrusions 218' cooperate with falling prevention wings 426' or re-use preventing wings 424' of the trigger part 400', and thereby the trigger part 400' is prevented from falling from the holder 200' before use of the device. While on the other hand, after the use, the protrusions 218' of the holder prevent the trigger part 400' from moving forwardly with respect to the holder 200', and thereby the returning of the device to its prickable state is prevented.

The form of the holder 200' is not limited to one shown in the drawings. As long as the holder can house therein the preliminary assembly as mentioned above, and has the above sloped portion and protrusion, the holder 200' may be in any other appropriate forms, for example, a cylindrical form. The holder 200' may be formed of any kind of resin materials as long as it is used for the lancet in general. For example, it is preferred that the holder 200' may be made of polyethylene, polypropylene or the like.
(Lancet)
FIG. 28 schematically shows a preferred embodiment of the lancet of the lancet pricking device of the type B. The lancet 100' shown in FIG. 28 comprises the lancet cap 170' and the lancet body 130'. The lancet cap 170' and the lancet body 130' are integrally coupled together by a weakened part 108' positioned therebetween, and the pricking needle 150' extends across these components (see FIG. 28(b) in which a part of the pricking needle is shown). A tip 150a' of the pricking needle is covered with the lancet cap 170'. Upon pricking, the weakened part 108' is broken to remove the lancet cap, so that the tip 150a' of the pricking needle is exposed and it extends forwardly from a front end 136' of the lancet body 130'.

The lancet body 130' has an engagement portion for securing the body 130' to the arms of the trigger part. That is, the lancet body has, on its both lateral sides, the engagement portions 131' (e.g., stepped portions or cornuted portions) which can engage with the respective engaged portions of the trigger part. Furthermore, the lancet body 130' has protrusions 138' for attaching the front end of the launching spring 300' thereto, at its rear portion 133'.

The lancet cap 170' includes a rear portion 172' covering the tip 150a' of the pricking needle, and also a front portion 175' positioned at its front side. A rear end of the rear portion 172' encloses the tip of the pricking needle, and is opposed to the front end of the lancet body 130' via the weakened part 108'. The front portion 175' of the lancet cap has a pair of parts 175a' at its lateral sides. More specifically, the front portion 175' of the lancet cap has a pair of opposed parts 175a' protruding backward at both lateral sides thereof, and also has a center part 175b' as the remaining part positioned between the opposed parts 175a'. In the lancet pricking device of the type B in which the holder 200', the trigger part 400', the lancet 100' and the launching spring 300' are in an assembled state, the opposed parts 175a' and/or center part 175b' are adjacent to a front opening end 203' of the holder 200', or opposed to the front opening end 203' via a slight gap. Therefore, even when the lancet 100' is intended to be moved backwardly with respect to the holder 200', the opposed parts 175a' and/or center part 175b' make(s) contact with the wall edge defining the front opening end 203' of the holder 200', and as a result, the lancet 100' cannot be moved backward any more.

In the embodiment shown in FIG. 28, the front portion 175' of the lancet cap 170' has a flat front end, which can be twisted or rotated around the pricking needle by being gripped with the fingers, so that the weakened part 108' is broken (that is, the front end portion to be gripped with the fingers corresponds to the "holding portion"). Preferably, in order to easily break the weakened part, the lancet body 130' can be positioned within the holder and the trigger part, but is formed as a whole in a prismatic shape to avoid rotating around the pricking needle. While on the other hand, the rear portion 172' of the lancet cap 170' is preferably formed in a cylindrical shape so as to be capable of rotating within a cylindrical front end portion 402' of the trigger part. Thus, when the lancet cap is gripped and twisted while holding the holder, the lancet body is prevented from being rotated, but the lancet cap can be rotated so that the weakened part 108' is broken. The weakened part 108' can be more suitably broken by the twist or rotation of the weakened part by appropriately selecting the thickness of the lancet resin portion covering the pricking needle, or by appropriately selecting the kind of the resin in itself.

(Trigger Part)

FIG. 27 schematically shows a preferred embodiment of the trigger part of the lancet pricking device of the type B. The trigger part 400' shown in FIG. 27 has, at its center, a space 406' for accommodating therein the lancet 100' and the launching spring 300' at a point in time of the pre-pricking state of the pricking device. The space is preferably formed as a whole in a box-like shape with a bottom portion. The space 406' has its cylindrical front end portion 402' which protrudes forwardly from the front end thereof. The opening 408' of the front end portion 402' is applied to the predetermined subject to be pricked.

The trigger part 400' has a pair of arms 420' extending backwardly at both lateral sides. As shown in FIG. 27, each of the opposed arms 420' has a fixed end at its front side, and a free end at its rear side. The each arm 420' is preferably flexible as a whole. The each arm 420' has, at its inner lateral side, the engaged portion 421' (for example, a stepped or cornuted portion on which the engagement portion 131' of the lancet body can abut). In the embodiment shown in FIG. 27, the each arm 420' has sliding portions 422' at the upper and lower sides of the engagement portion 421'. When the trigger 400' moves backwardly with respect to the holder 200' in the lancet pricking device of the type B, each of the sliding portions 422' slides on the sloped portion 250' (more specifically "sloped surface 250a'''") provided at the inner wall of the holder, or moves on the sloped portion 250' (more specifically "sloped surface 250a'''") under friction against the portion 250'. As a result of such sliding or moving, as shown by the arrows in FIGS. 27(*a*) and 27(*b*), the arms 420' are caused to be expanded outwardly with their front roots (i.e., fixed ends) serving as their fulcrums.

The each arm 420' of the trigger part 400' shown in the drawings has push-back portions 416' at its outer sides. The each of the push-back portions 416' preferably protrudes outwardly from the arm 420'. It is more preferred that the each push-back portion 416' protrudes obliquely and forwardly as shown in FIG. 27. In the lancet pricking device of the type B, the tip of the each push-back portion 416' is in contact with the inner wall of the holder, or is slightly spaced from such inner wall. As a result, when the outward expansion of the arms 420' is performed, the push-back portions 416' are pressed toward the inner wall of the holder, and thereby the force attributed to the counteraction acts to push back or thrust the arm inwardly. It is preferred that the each push-back portion 416' has the form of an auxiliary arm protruding outwardly (preferably outwardly and obliquely) from the arm 420' as shown in FIG. 27.

The provision of the push-back portions 416' in the arms 420' serves to push back the arms 420' in some cases other than a case where a relatively large force is applied to the pricking device (especially, some cases other than the case where the trigger part is forced to move backwardly with respect to the holder upon the pricking operation). Specifically, the push-back portions 416' serve to push back the arms 420' when some unintentional force is applied to the arms 420' by any reason to expand the arms 420' outwardly. This can ensure the securing of the engagement portion 131' of the lancet body to the engaged portion 421' of the trigger part, even when such unintentional force is applied.

Figure 34:
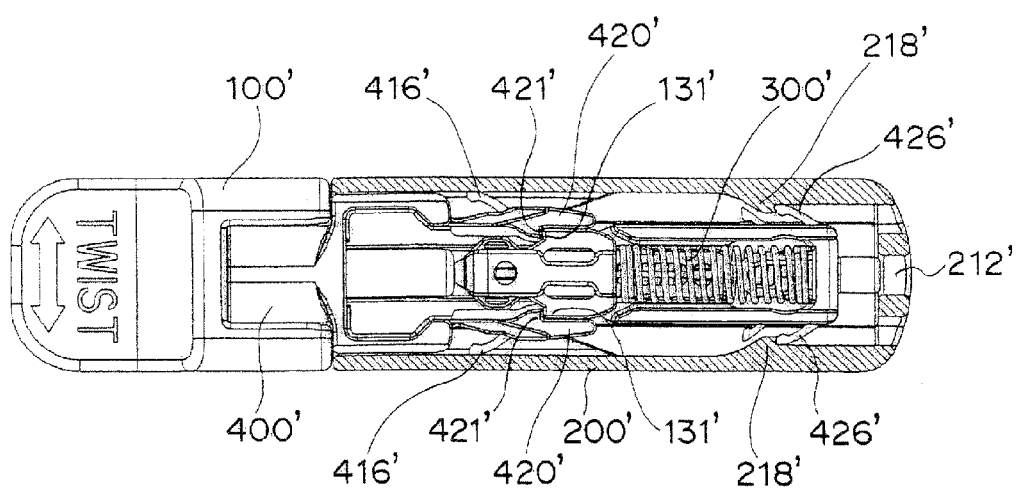
FIG. 34(a) is a part of series of the processes for pricking a region of interest using the lancet pricking device of the type B as shown in FIGS. 34 (a) to (f). Specifically, FIG. 34(a) schematically shows a top view of the state of the inside of the pricking device already assembled as shown in FIG. 33, the upper half of the holder and trigger part being cut away.
FIG. 34(b) is another part of series of the processes for pricking the region of interest using the lancet pricking device of the type B as shown in FIGS. 34(a) to (f). Specifically, FIG. 34(b) schematically shows the state after that of FIG. 34(a), in which the lancet cap has been removed from the lancet (note that the upper half of the front end of the trigger part is cut away for understanding).
FIG. 34(c) is another part of series of the processes for pricking the region of interest using the lancet pricking device of the type B as shown in FIGS. 34(a) to (f). Specifically, FIG. 34(c) schematically shows the state after that of FIG. 34(b), in which the front end opening of the trigger part is applied to the region of interest to be pricked (note that the state of the device itself is the same as that of FIG. 34(b)).
FIG. 34(d) is another part of series of the processes for pricking the region of interest using the lancet pricking device of the type B as shown in FIGS. 34(a) to (f). Specifically, FIG. 34(d) schematically shows the state after that of FIG. 34(c), in which the front end opening of the trigger part is pushed against the region of interest to be pricked to force the trigger part to move backwardly with respect to the holder, and thereby causing the arms of the trigger part to be expanded to release the securing of the lancet body to the arms.
FIG. 34(e) is another part of series of the processes for pricking the region of interest using the lancet pricking device of the type B as shown in FIGS. 34(a) to (f). Specifically, FIG. 34(e) schematically shows the state after that of FIG. 34(d), in which the launching spring has just been instantly expanded. As a result, the lancet body with the tip of a pricking needle exposed is forced to move forwardly to collide with a stopper of the trigger part, whereby a part of the tip of the pricking needle (i.e., tip containing the most tip end of the pricking needle) is protruded from the front opening of the trigger part to prick the region of interest.
FIG. 34(f) is another part of series of the processes for pricking the region of interest using the lancet pricking device of the type B as shown in FIGS. 34(a) to (f). Specifically, FIG. 34(f) schematically shows the state after that of FIG. 34(e), in which the expanded launching spring has just been returned to its original length, and thereby the tip of the pricking needle has just been pulled into the front end of the trigger part.
Figure 34:
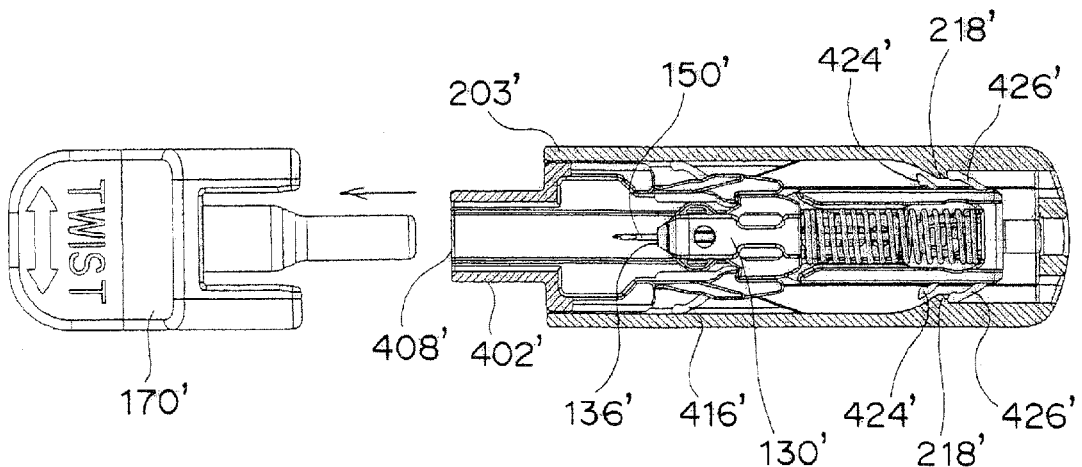
Figure 34:
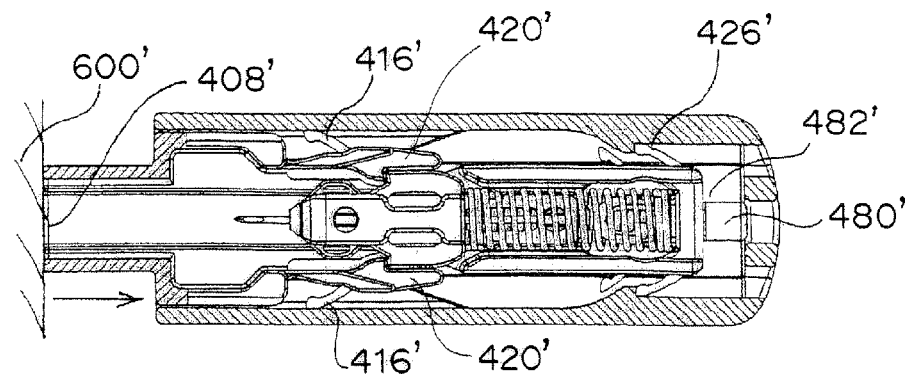
Figure 34:
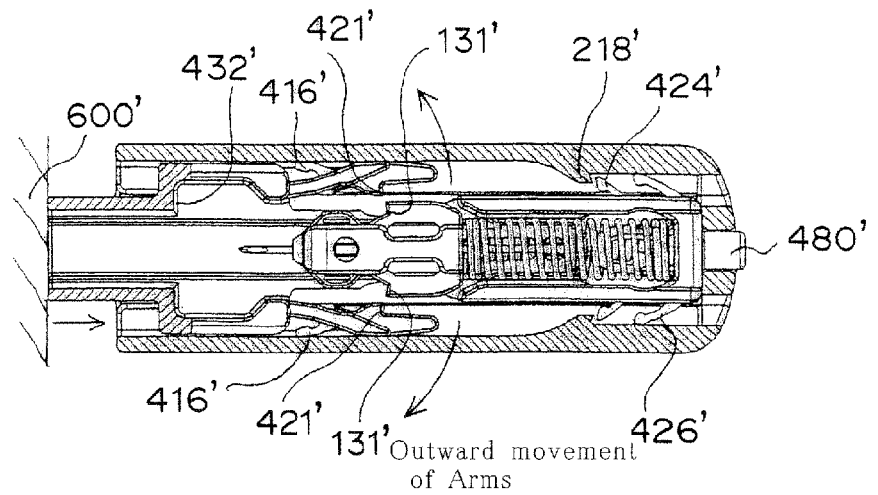
Figure 34:
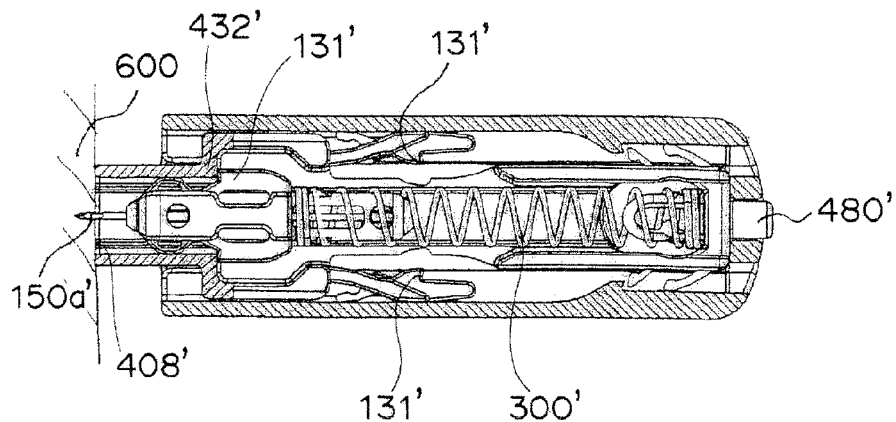
Figure 34:
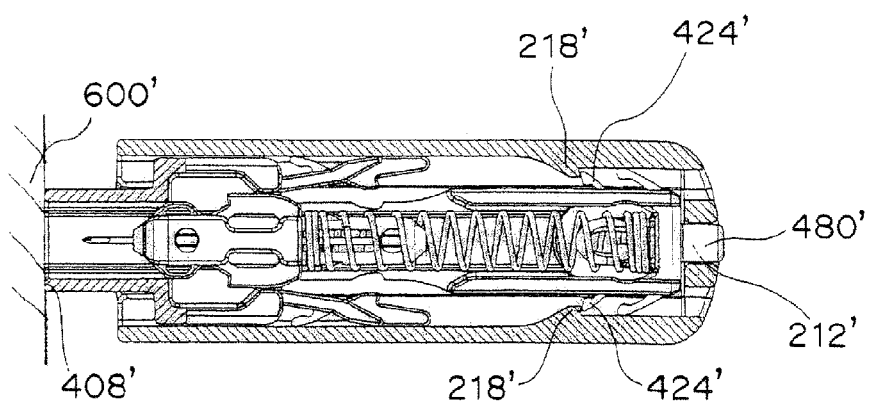

The trigger part 400' of the type B has, behind its space portion, a rear-most end portion 480' which protrudes backwardly. After the pricking operation, the rear-most end portion 480' is fitted into the space 212' of the holder 200', and a stepped portion 482' defining the rear-most end makes contact with the wall portion 214' defining the space 212'. As shown in FIG. 34(*e*), when the rear-most end portion 480' slightly protrudes from the space 212' (especially in a case where the end surface of the rear-most end 480' is clearly colored), the user can recognize that the pricking device is used one.

As shown in the drawings (especially, as shown in FIG. 29), the trigger part 400' has re-use preventing wings 424' in a protruding or arm-like shape, at its outer lateral faces (especially, outer lateral faces at the rear side of the trigger part), and also falling prevention wings 426' in a protruding or arm-like shape behind the wings 424'. These wings (424', 426') cooperate with the protrusions 218' provided at the inner walls of the lateral sides of the holder 200' to fulfill their functions. As shown in FIG. 26(*c*), the each protrusion 218' provided at the inner wall of the holder preferably has an inclined surface (i.e., tapered surface) wherein its front-sided surface portion 217' extends outwardly in the forward direction.

When the preliminarily assembled parts are inserted into the holder upon assembling the pricking device of the present invention, each of the falling prevention wings 426' is brought into contact with each of the protrusions 218' provided at the inner side walls of the holder, and are caused to be deformed inwardly, while sliding on the inclined surfaces 217' to ride over the protrusion 218. After the wing 426' rides over the protrusion 218, the wing 426' is returned to its original shape, which leads to a completion of the assembling of the pricking device.

As shown in FIG. 26(*c*), it is preferred that the each protrusion 218' has its rear end surface 219' extending perpendicular or approximately perpendicular to the pricking direction. As a result, once the each wing 426' moves backwardly to ride over the each protrusion 218', the wing 426' cannot forwardly ride over the protrusion 218' any more. That is, the falling prevention wing 426' of the trigger part 400' before use of the device is positioned behind the protrusion 218' of the holder 200', and thereby the trigger 400' cannot move forwardly with respect to the holder 200', which serves to effectively prevent the trigger part 400' from falling from or coming off the holder 200'.

After the lancet pricking device of the type B is used, the re-use preventing wings 424' provided in front of the falling prevention wings 426' have returned to their original shape after their deformation in the same manner as the above riding of the wings 426'. That is, the each wing 424' is located behind the protrusion 218' of the inner side wall of the holder 200', after riding over the protrusion 218' upon the pricking operation. As a result, the trigger 400' cannot be moved forward with respect to the holder 200' after the device is used. This means that the positional relationship between the holder 200' and the trigger part 400' after the pricking cannot be returned to its original state of pre-pricking. In this regard, the opened arms of the trigger part cannot be closed again, and thus the engaged portion 421' of the trigger part cannot be again in engagement with the engagement portion 131' of the lancet body. Accordingly, the used lancet body cannot be any more ready for pricking, and thus cannot be used for another pricking operation. The deformation of the wings 424' and 426' and the restoring thereof to their original shapes can be easily achieved by forming the trigger part 400' with resin (for example, resin such as polyethylene and polystyrene), and then making use of the elastic property of such resin. For this reason, these wings preferably have flexibility as a whole.

The trigger part 400' has a spring attachment portion 450'. The spring attachment portion can suitably work for the assembling of the lancet pricking device. Specifically, in a case where the spring attachment portion 450' of the trigger part is comprised of a bent elongated part having a free end and a fixed end as shown in FIGS. 27(b) and 22, the assembling of the lancet pricking device (in particular, attaching of the launching spring 300') is effectively facilitated. That is, as shown in FIGS. 27(b) and 22, when the spring attachment portion 450' is provided in the form of a hook (e.g., fishing-needle form or U-like form), the inward warping of the spring attachment portion 450' can be easily performed (see FIGS. 22(a) and 22(b)), so that the engagement of the launching spring coil with the attachment portion of the trigger part can be effectively facilitated. It is preferred that the spring attachment portion 450' has a protrusion 450a' that protrudes outwardly. In particular, a first protrusion $450a_1'$ is preferably provided at the free end of the bent elongated part, whereas a second protrusion $450a_2'$ is preferably provided at the fixed end of the bent elongated part as shown in FIG. 22(a). In this case, once the spring 300' increases its coil diameter to ride over the protrusions 450a', then the spring 300' is returned to have its original coil diameter. As a result, a joint between the spring 300' and the spring attachment portion 450' cannot be easily released any longer (see FIGS. 22(a) to 22(c)).
(Launching Spring)

The launching spring 300' is used for shooting, firing or launching the lancet (more specifically, the lancet body with the tip of the pricking needle exposed therefrom). In other words, the launching spring 300' is a spring (for example, a metallic coil spring) that gives an impellent force for launching the pricking needle 150', i.e., the "lancet body including the exposed pricking needle", or a driving force for pricking.

Figure 32:
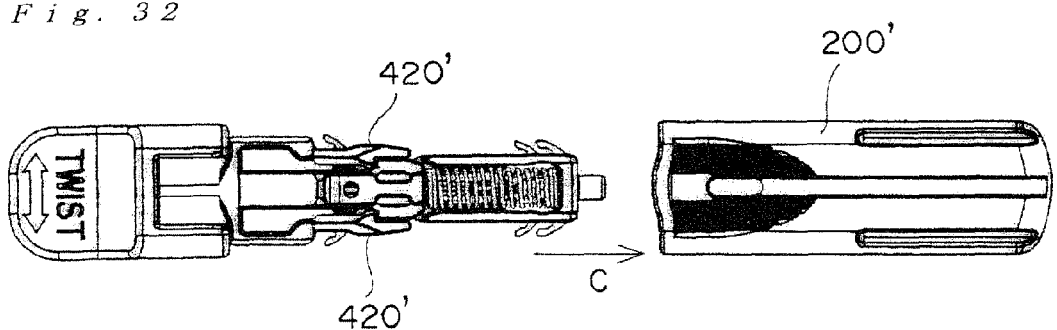
FIG. 32 schematically shows an embodiment wherein a pricking device is assembled by loading a lancet and a trigger part with a launching spring attached thereto into a holder in a lancet pricking device of Type B, in which the top view thereof is shown.
Figure 33:
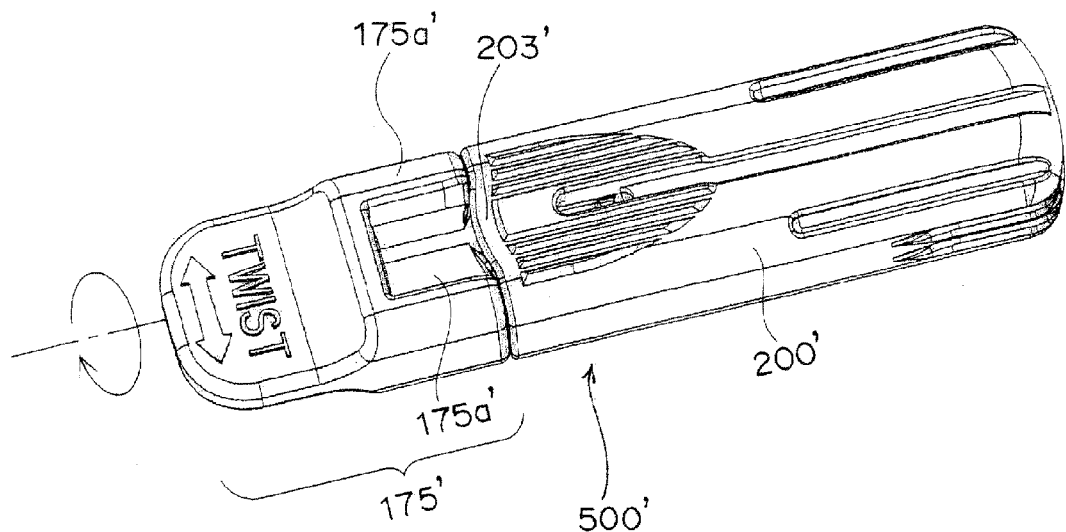
FIG. 33 is a perspective view schematically showing a lancet pricking device of the present invention assembled according to the embodiment shown in FIG. 32.

FIG. 33 is a perspective view showing the pricking device 500' of the type B assembled as described with reference to FIGS. 30 to 32. As shown in FIG. 33, a front portion 175' of the lancet cap is in contact with or adjacent to (via a slight gap) the front opening end 203' of the holder 200'. As a result, when the lancet is intended to be moved backwardly with respect to the holder 200', the pair of parts 175a' of the front portion abuts against the holder wall edge defining the front opening end 203'. This means that the backward movement of the lancet is prevented.

In this state, the holder 200' is held with the fingers of one hand, and the front end of the lancet is gripped with the fingers of the other hand. Then, the holder and the lancet are rotated or twisted in the reverse direction to each other around the extending direction of the pricking needle (i.e., rotated or twisted in the direction indicated by the dashed-dotted line) as indicated by the arrow in FIG. 33, so that the "weakened part" is broken. Subsequently, the lancet cap is pulled so as to be spaced apart from the holder along the extending direction of the pricking needle, and consequently the tip of the pricking needle is exposed inside the holder.

FIG. 34(a) schematically shows the state of the inside of the pricking device 500' shown in FIG. 33. As can been seen from FIG. 34(a), the trigger part 400' is positioned inside the holder 200', and the falling prevention wings 426' are in rear abutment with protrusions 218' provided at the inner side walls of the holder 200'. Thus, the trigger part 400' cannot be pulled out of the holder 200', that is, the trigger part is surely held within the holder. The engaged portions 421' of the trigger part 400' in this state are in engagement with the engagement portions 131' of the lancet. Thus, the launching spring 300' attached to the lancet is kept compressed within the holder 200', due to the engagement between the engagement portions 131' of the lancet and the engaged portions 421' of the trigger part 400'.

As shown in the drawings, the push-back portions 416' are additional or auxiliary arms protruding obliquely and forwardly from the arms 420'. The tip of the each push-back portion 416' is in contact with the inner side wall of the holder 200'.

Now, the pricking procedure for pricking the region of interest using the pricking device 500' of the type B will be described with reference to the top views of FIGS. 34(a) to 34(f) and the perspective views of FIGS. 35(a) to 35(f).

Figure 35:
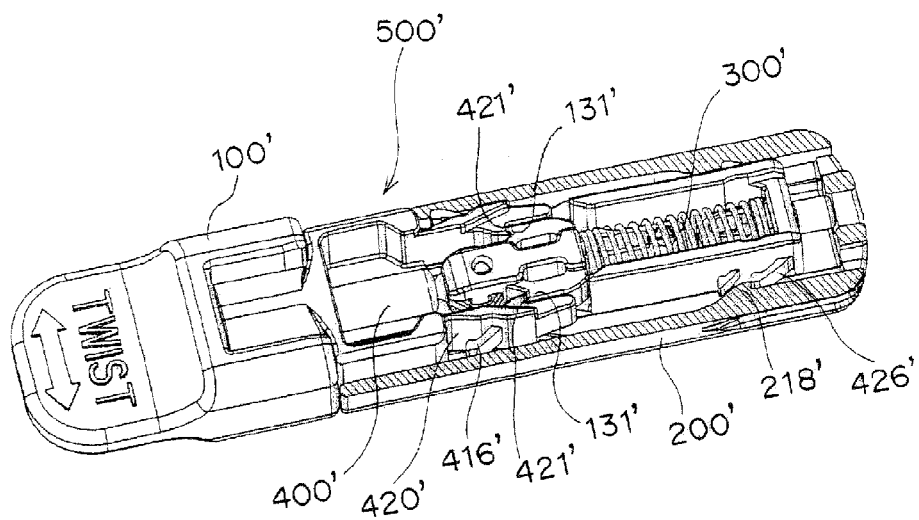
Figure 35:
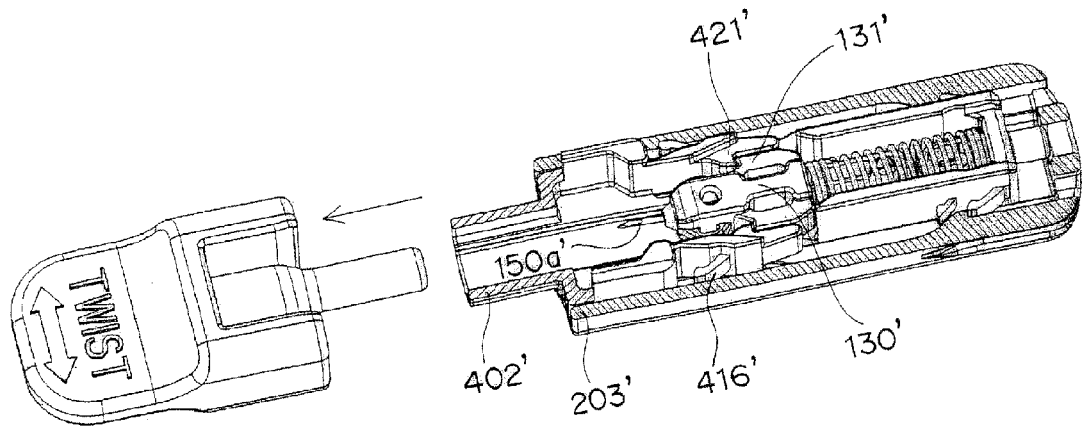
Figure 35:
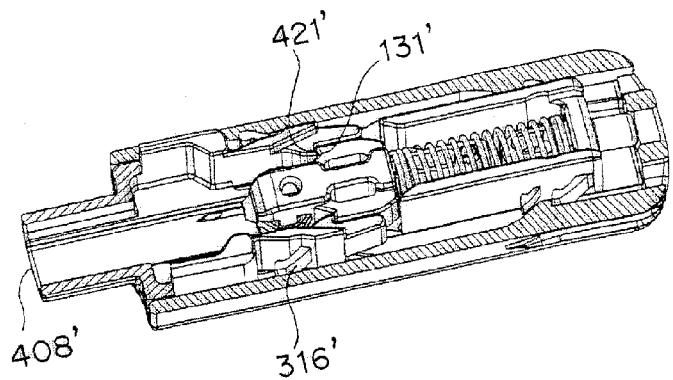
Figure 35:
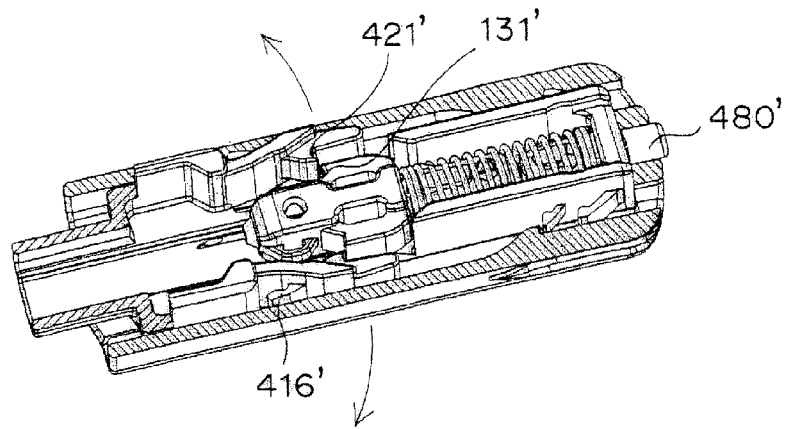
Figure 35:
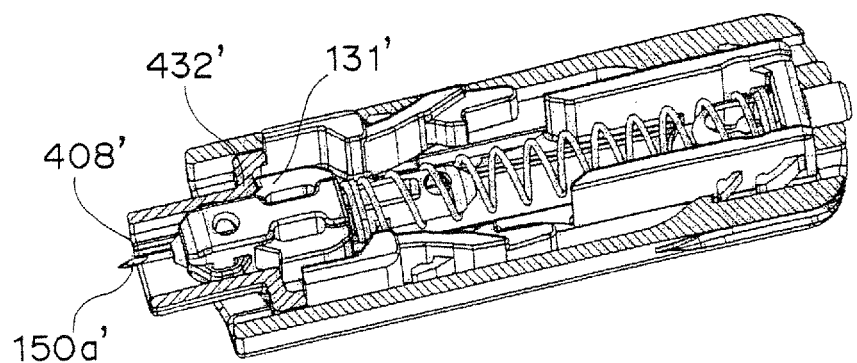
Figure 35:
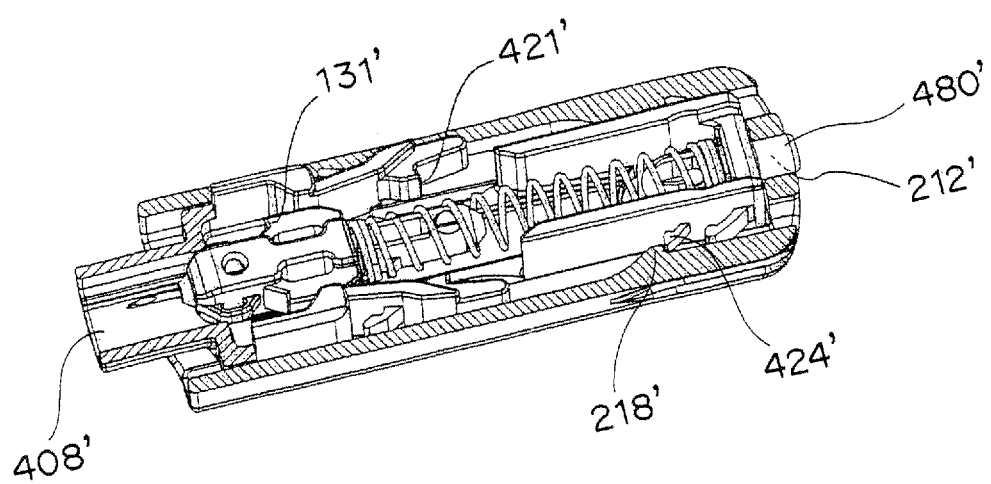

First, within the holder 200' of the lancet pricking device 500' of the type B shown in FIG. 34(a) and FIG. 35(a), the weakened part 108' of the lancet is broken by the twisting operation as described above. Then, as indicated by the arrows shown in FIG. 34(b) and FIG. 35(b), the lancet cap 170' is forced to be spaced apart from the lancet body 130' so that the tip 150a' of the pricking needle is exposed and it extends forward from the lancet body. After the removal of the lancet cap 170', the front portion 402' of the trigger part 400' is all exposed such that it extends forwardly beyond the front opening end 203' of the holder 200'. In the state shown in FIGS. 34(b) and 35(b), the lancet body 130' with the tip 150a' of the pricking needle protruding therefrom is surely held within the space 406' of the trigger part 400' by the abutment relationship between the engagement portion 131' and the engaged portion 421'.

Then, in the lancet pricking device 500' shown in FIGS. 34(b) and 35(b), the front opening portion 408' of the protruding trigger part is applied to a region 600' of interest to be pricked. The state in which the front opening portion 408' has been applied to the region of interest is shown in FIG. 34(c) and FIG. 35(c).

Thereafter, in the lancet pricking device 500' shown in FIG. 34(c) and FIG. 35(c), the holder 200' is pressed against the region of interest 600' so that the pricking device approaches the region 600'. That is, the stamping operation is performed. Such operation can generate a force for causing the trigger part 400' to move backwardly with respect to the holder 200'. In the lancet pricking device of the type B, the arms 420' of the trigger part 400' have push-back portions 416', which can serve to suppress the expansion of the arms 420'. Especially, push-back portions 416' can serve to push the arms 420' toward the lateral sides of the lancet body. Thus, the force for the stamping operation is required to be larger than the force generated attributed to the push-back portion 416' to suitably perform the backward moving of the trigger part.

During the backward moving of the trigger part 400', the sliding portion 422' of the each arm 420' moves backwardly on the sloped portion 250' provided in the each lateral inner wall of the holder 200'. The sloped portion 250' has the sloped surface 250a' which is inclined closer to the inner lateral wall of the holder in the direction of the rear thereof. Accordingly, upon the backward moving of the trigger part 400', the sliding portion 422' moves not only backwardly but also outwardly (specifically, the sliding portion 422' moves backwardly and obliquely toward the outside). In this regard, the sliding portion 422' corresponds to a part of the each arm 420' of the trigger part, and thus the each arm 420' also moves outwardly as a whole, together with the sliding portion 422'. That is, the outward expansion of the arms 420' of the trigger part is performed as indicated by the arrows of FIG. 34(d). By comparison the shapes of the push-back portion 416' between FIGS. 34(c) and 34(d), it is easy to understand that the push-back portion 416' has been deformed slightly inward from its original shape.

When the arms 420' are expanded outwardly, the engaged portions 421' of the trigger part also move outwardly. As a result, the abutment relationship between the engaged portions 421' of the trigger part and the engagement portion 131' of the lancet body cannot be maintained any longer. That is, the engagement between the engaged portions 421' and the engagement portion 131' ceases. The state in which the engagement has ceased is shown in FIG. 34(d) and FIG. 35(d). When the engagement ceases, there is no means for preventing "forward movement of the lancet body 130' due to the compressed launching spring 300'". Thus, the forward moving of the lancet body 130' with the tip of the needle exposed is instantly performed.

The launching spring 300' is instantly expanded from the compressed state thereof. Thus, the launching spring 300' becomes longer than its original state (i.e., longer than the state where it does not substantially receive the force). The expansion of the spring 300' causes at least one part of the tip 150a' of the pricking needle to protrude beyond the front end opening portion 408' of the trigger part 400'. The front opening portion 408' is in contact with the region of interest to be pricked, and thus the region of interest is prickled by the protruding tip of the needle. A part of the lancet body (e.g., engagement portion 131' in the embodiment shown in the drawings) collides with the wall surface 432' positioned behind the front end of the trigger part 400' to thereby restrict the forward movement of the lancet body 130'. The state in which the region of interest is pricked is shown in FIG. 34(e) and FIG. 35(e).

In the state shown in FIG. 34(e) and FIG. 35(e), the launching spring 300' has been expanded longer than its original length as described above. Directly after the forward movement of the lancet body is achieved, the lancet body starts to move backwardly by the counteracting force attributed to the wall surface 432'. The launching spring 300' is finally returned to its original shape. FIG. 34(f) and FIG. 35(f) show the state in which the launching spring has been returned to its original shape. The launching spring 300' is preferably selected such that, in the state of the launching spring returned to its original shape, the tip of the pricking needle protruding from the lancet body is positioned sufficiently far away from the front end opening 408' of the trigger part 400'.

During the retracting of the trigger part 400' with respect to the holder 200', the re-use preventing wings 424' of the trigger part move backwardly so that they ride over the corresponding protrusions 218' provided at the lateral inner walls of the holder 200'. During the retracting of the trigger part, the rear-most end portion 480' of the trigger part 400' is fitted into the space 212' positioned at the rear end of the holder 200', and also the stepped portion 482' of the trigger part makes contact with the wall 214' defining the rear end of the holder 200' (also see FIGS. 26(b) and 27(b)).

In the state shown in FIG. 34(f) and FIG. 35(f), even when the trigger part 400' is intended to move forwardly with respect to the holder 200', the re-use preventing wings 424' of the trigger part abut against the protrusions 218' of the holder, so that the trigger part cannot be forwardly moved any more. Moreover, even when the trigger part 400' is intended to move backwardly with respect to the holder 200' in the state shown in FIGS. 34(f) and 35(f), the stepped portions of the trigger part abut against the wall of the holder, so that the trigger part 400' cannot be backwardly moved any more.

Accordingly, once the state shown in FIGS. 34(f) and 35(f) is obtained, the positional relationship of the trigger part 400' with respect to the holder 200' cannot be substantially changed. This means that, even when the lancet body 130' is intended to be backwardly moved, the arms of the trigger part remain expanded, so that the abutment relationship between the engaged portion 421' of the trigger part and the engagement portion 131' of the lancet body cannot be provided again. As a result, the lancet body with the tip of the used pricking needle exposed therefrom cannot be reused for pricking. The used pricking needle cannot be reused, which is very desirable from the viewpoint of hygiene and safety. In light of the device embodiment with such re-use preventing mechanism, the lancet pricking device of the type B can be referred to as the "single use device", similarly to the lancet pricking device of the type A.

[Lancet Pricking Device of Type C]
<<Basic Structure of Lancet Pricking Mechanism>>
(Basic Structure)

Figure 38:
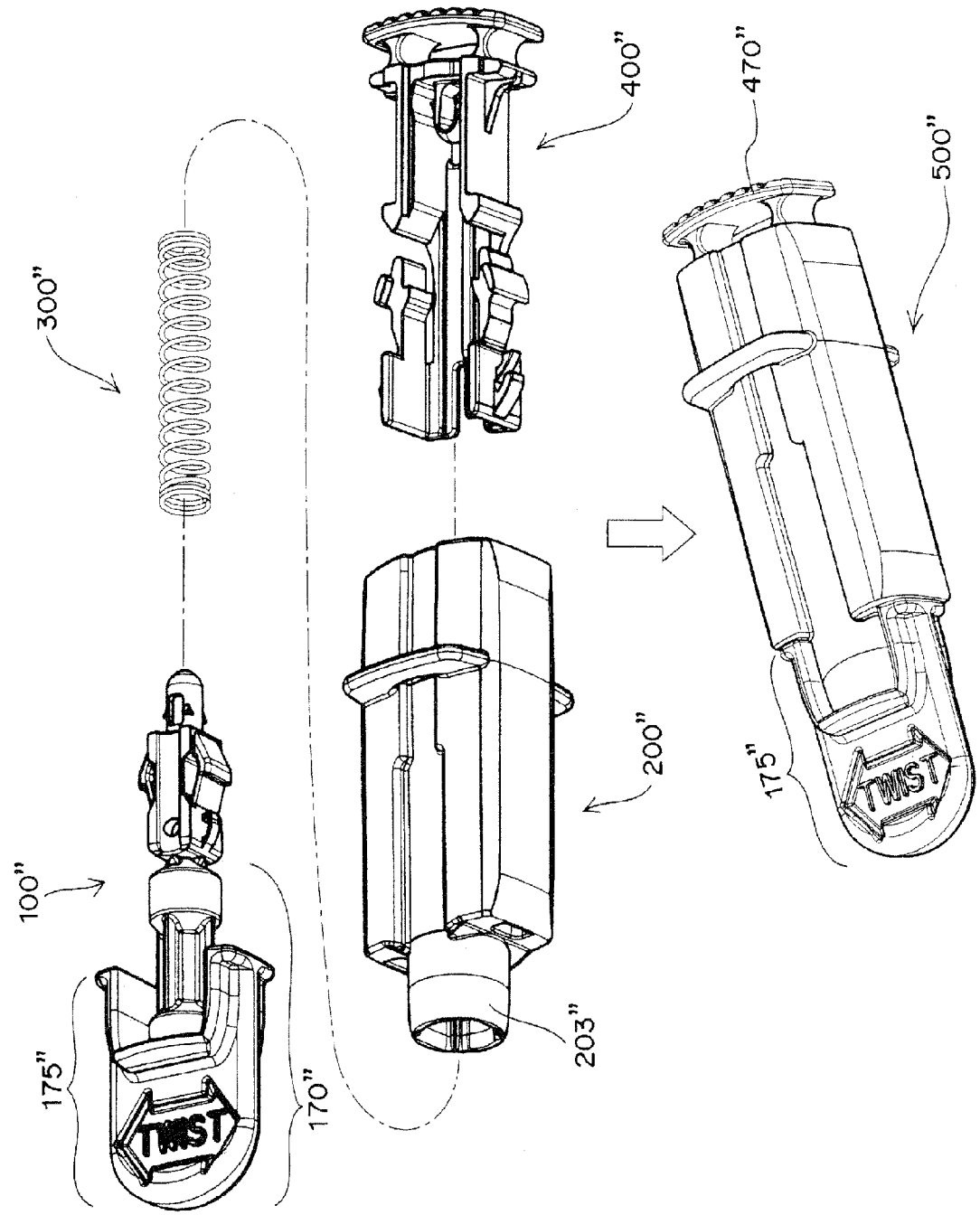
FIG. 38 shows an appearance view and an exploded perspective view of a lancet pricking device of Type C.
Figure 42:
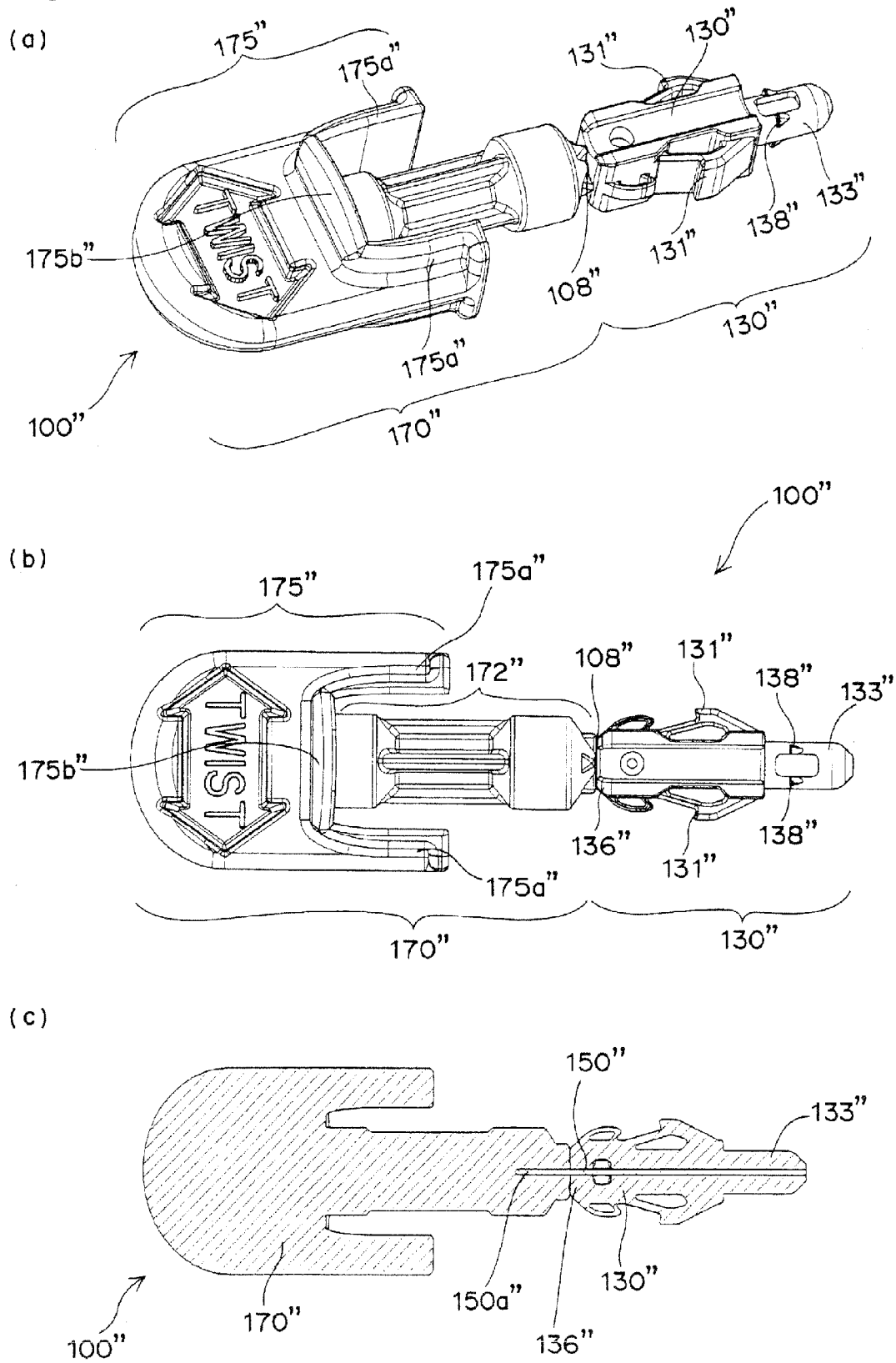
FIGS. 42(a) to 42(c) are a perspective view, a top view and a cross-sectional view of a lancet of a lancet pricking device of Type C.

FIGS. 36 to 38 show a lancet pricking device 500" of the type C. FIGS. 36 and 37 show appearance diagrams of the lancet pricking device 500" of the type C. FIG. 38 shows an exploded diagram and a development diagram of the lancet pricking device 500" of the type C. As shown in FIG. 38, the lancet pricking device 500" of the present invention is mainly composed of a lancet 100", a launching spring 300", a holder (especially, lancet holder) 200" and a trigger part 400". FIG. 39 shows the holder 200" of the lancet pricking device of the type C. FIGS. 40 and 41 show the trigger part 400" of the lancet pricking device of the type C. FIG. 42 shows the lancet 100" of the lancet pricking device of the type C.

Figure 43:
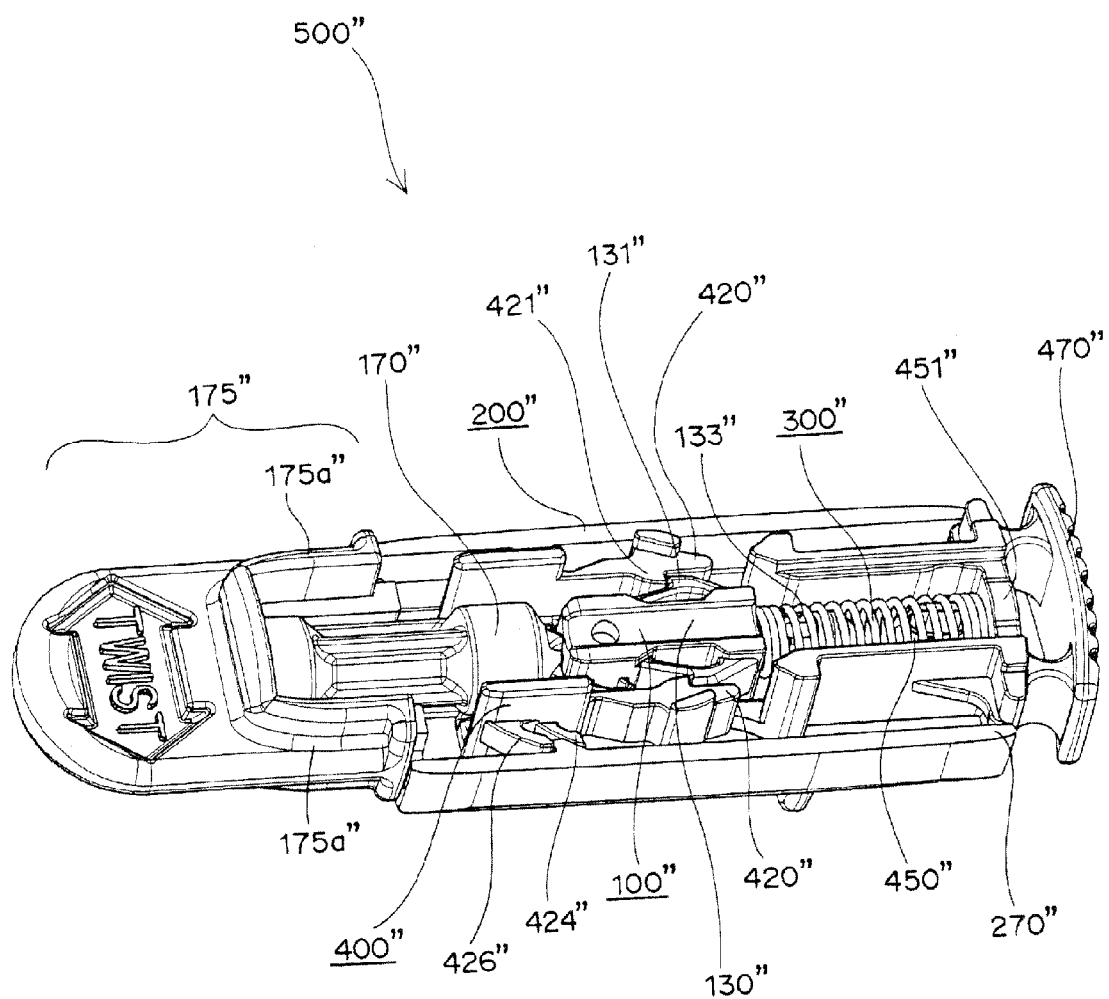
FIG. 43 is a perspective view showing an internal structure of a lancet pricking device of Type C at a point in time before it is put into use.

FIG. 43 shows the lancet pricking device 500" of the type C with the upper half of the holder 200" cut away therefrom. As shown in FIG. 43, the lancet pricking device 500" has such a structure that the lancet 100" the launching spring 300" and the trigger part 400" are housed in the lancet holder 200". Specifically, as shown in FIG. 43, the launching spring 300" is housed in the lancet holder 200" such that the launching spring 300" is held between a rear end 133" of the lancet 100" and a rear end 451" of the trigger part 400". More specifically, as shown in FIG. 43, within the holder 200", one end of the launching spring 300" is attached to the rear end 133" of the lancet 100", and whereas the other end of the launching spring 300" is attached to a fitting portion 450" of the trigger part 400". Similarly to the pricking devices of the type A and the type B, the launching spring 300" inside the lancet holder 200" is in a compressed state between the lancet 100" and the fitting portion 450" provided at the rear end of the trigger part 400". In other words, in the lancet pricking device 500" of the present invention, a lancet body 130" is secured (locked) to arms 420" of the trigger part 400" such that the launching spring 300" attached to the lancet body 130" is kept compressed. See also FIGS. 40(a) and 42(a) for understanding an engagement portion 131" of the lancet body 130", and also an engaged portion 421" of the arm 420 of the trigger part 400" which are associated with the securing.

As can be seen from the embodiments shown in FIGS. 36, 38, and 43, the lancet pricking device 500" of the type C has such a feature that the trigger part 400" is disposed as a whole in the holder 200" such that only a pressing portion 470" provided at the rear end of the trigger part 400" protrudes outward from a rear end opening 270" of the holder 200" (i.e., an opening provided at a rear end of the holder as shown in these Figures). Further, as can be seen from the embodiments shown in FIGS. 36 and 43, a front portion 175" of a lancet cap 170" protrudes outwardly from the front opening end 203" of the holder. In such embodiment of the lancet cap, a pair of opposed parts 175a" provided at lateral sides of the front portion 175" of the lancet cap is adjacent to the front end opening 203" of the holder, and/or, the other parts of the front portion 175" of the lancet cap (especially, a cap center region 175b" provided between the pair of the parts 175a") is adjacent to the front end opening 203" of the holder (i.e., pricking opening portion of the holder). As a result, the lancet 100" is prevented from moving backwardly with respect to the holder 200".

After the lancet cap is removed from the lancet in the lancet pricking device of the type C, the trigger part can be pushed forwardly. Specifically, when the external force is applied to the pressing portion 470" provided at the rear end of the trigger part 400", the trigger part can be pushed into the holder so that the trigger part 400" moves forwardly with respect to the holder 200".

The assembling of the lancet pricking device of the type C is substantially the same as that of the lancet pricking devices of the type A and the type B. That is, the pricking device of the type C can be obtained by assembling the lancet 100", the launching spring 300", the holder 200" and the trigger part 400" while keeping the compressed state of the launching spring 300" therein (see FIG. 38 or FIG. 44).

In the following, components or parts regarding the lancet pricking device 500" of the type C will be described.
(Holder)

FIG. 39 schematically shows a preferred embodiment of the holder 200" of the pricking device of the type C. As shown in FIG. 39, the holder 200" has a cylindrical shape as a whole, and has a substantially rectangular cross-section perpendicular to the pricking direction.

As shown in FIGS. 39(*b*) and 39(*c*), the inner walls of the lateral sides of the holder 200" are respectively provided with the sloped portions 250". The sloped portion 250" has a sloped surface 250*a*" which is inclined toward the outside of the holder (i.e., toward the outward) in the forward direction. In the embodiment shown in FIGS. 39(*b*) and 39(*c*), the sloped portions are provided at upper lateral side and lower lateral side of the holder (note that only the sloped surface at the lower lateral side is shown). As mentioned later, a part of the each arm 420" of the trigger part slides on the sloped surface 250*a*" or moving while contacting the surface 250*a*". Specifically, when the trigger part 400" is forced to move forwardly with respect to the holder 200", the free end of each arm 420" slides on the sloped surface 250*a*" or moves on the sloped surface 250*a*" under friction against the surface 250*a*" in the direction from the rear toward the front. As a result, the outward expansion of the arms of the trigger part is automatically performed.

The holder 200" has protrusions (convex portions) 218" in front of the sloped portions 250". As described later, the protrusions 218" cooperate with falling prevention wings 426" or re-use preventing wings 424" of the trigger part 400", and thereby the trigger part 400" is prevented from falling from the holder 200" before use of the device. While on the other hand, after the use of the device, the protrusions 218" of the holder serve to prevent the trigger part 400" from moving backwardly with respect to the holder 200" to return to the prickable state thereof.

Similarly to the pricking devices of the type A and the type B, the form of the holder 200" is not limited to one shown in the drawings. As long as the holder can house therein the trigger part, the launching spring and the lancet, and also has the above sloped portion and protrusion, the holder 200" may be in any other appropriate forms, for example, a cylindrical form. The lancet holder 200" may be formed of any kind of resin materials as long as the resin can be used for the lancet in general. For example, it is preferred that the holder 200" may be made of polyethylene, polypropylene or the like.
(Lancet)

FIG. 42 schematically shows a preferred embodiment of the lancet of the lancet pricking device of the type C. The lancet 100" shown in FIG. 42 comprises the lancet cap 170" and the lancet body 130". The lancet cap 170" and the lancet body 130" are integrally coupled together by a weakened part 108" positioned therebetween, and the pricking needle 150" extends therein (see FIG. 42(*c*)). A tip 150*a*" of the pricking needle is covered with the lancet cap 170". Upon pricking, the weakened part 108" is broken to remove the lancet cap, so that the tip 150*a*" of the pricking needle is exposed and it extends forwardly from a front end 136" of the lancet body 130".

The lancet body 130" has an engagement portion for securing the body 130" to the arms of the trigger part. That is, the lancet body has, at its both lateral sides, the engagement portions 131" (e.g., stepped portions or cornuted portions) which can engage with the respective engaged portions of the trigger part. Furthermore, the lancet body 130" has protrusions 138" for attaching the front end of the launching spring 300" thereto, at its rear end portion 133".

The lancet cap 170" includes a rear portion 172" covering the tip 150*a*" of the pricking needle, and also a front portion 175" positioned at its front side. A rear end of the rear portion 172" encloses the tip of the pricking needle, and is opposed to the front end of the lancet body 130" via the weakened part 108". The front portion 175" of the lancet cap has a pair of parts 175*a*" at its lateral sides. More specifically, the front portion 175" of the lancet cap has a pair of opposed parts 175*a*" protruding backward at both lateral sides thereof, and a center part 175*b*" as the remaining part positioned between the opposed parts 175*a*". In the lancet pricking device of the type C in which the holder 200", the trigger part 400", the lancet 100" and the launching spring 300" are in an assembled state, the opposed parts 175*a*" and/or center part 175*b*" are adjacent to a front opening end 203" of the holder 200", or opposed to the front opening end 203" via a slight gap. As a result, even when the lancet 100" is intended to be moved backward with respect to the holder 200", the opposed parts 175*a*" and/or center part 175*b*" make(s) contact with the wall edge defining the front opening end 203" of the holder 200", and thus the backward moving of the lancet 100" is prevented.

In the embodiment shown in FIG. 42, the front portion 175" of the lancet cap 170" has a flat front end which can be twisted or rotated around the pricking needle by being gripped with the fingers, so that the weakened part 108" is broken (that is, the front end portion of the cap to be gripped with the fingers corresponds to the "holding portion"). Preferably, in order to easily break the weakened part, the lancet body 130" can be positioned within the holder and the trigger part, but is formed as a whole in a prismatic shape to avoid rotating around the pricking needle. While on the other hand, the rear portion 172" of the lancet cap 170" is preferably formed in a cylindrical shape so as to be capable of rotating within a cylindrical front end portion 203" of the holder. Thus, when the lancet cap is gripped and twisted while holding the holder, the lancet body is prevented from being rotated, but the lancet cap can be rotated to break the weakened part 108"
(Trigger Part)

FIGS. 40 and 41 schematically show a preferred embodiment of the trigger part of the lancet pricking device of the type C. The trigger part 400" shown in FIGS. 40 and 41 has, at its center, a space 406" for accommodating therein the lancet 100" and the launching spring 300" in the pre-pricking state of the pricking device. Such space is preferably formed as a whole in a box-like shape with a bottom portion.

The trigger part 400" has a pair of arms 420" extending backwardly at both lateral sides thereof. As shown in FIGS. 40 and 41, each of the opposed arms 420" has a fixed end at its front side, and a free end at its rear side. The each arm 420" is preferably flexible as a whole. The each arm 420" has, at its inner lateral side, the engaged portion 421" (for example, a stepped or cornuted portion on which the engagement portion 131" of the lancet body can abut). In the embodiment shown in FIGS. 40 and 41, the each arm 420" has sliding portions 422" at the upper and lower sides of the engagement portion 421". When the trigger 400" moves forwardly with respect to the holder 200" in the lancet pricking device of the type C, each of the sliding portions 422" slides on the sloped portion 250" (more specifically the sloped surface 250a") provided at the inner wall of the holder, or moves on the sloped portion 250" (more specifically sloped surface 250a") under friction against the portion 250". As a result of such sliding or moving, as shown by the arrows in FIGS. 40(*a*) and 41(*a*), the arms 420" are caused to be expanded outwardly with their front roots (i.e., fixed ends) serving as their fulcrums.

As shown in the drawings (especially, as shown in FIGS. 40(*a*) and 41(*a*)), the trigger part 400" has re-use preventing wings 424" in a protruding or arm-like shape, at its outer lateral faces (especially, outer lateral faces at the front side of the trigger part), and also falling prevention wings 426" in a protruding or arm-like shape in front of the wings 424". These wings (424", 426") cooperate with the protrusions 218" provided at the inner walls of both lateral sides of the holder 200" to fulfill their functions. As shown in FIG. 39(*c*), the each protrusion 218" provided at the inner wall of the holder preferably has an inclined surface (i.e., tapered surface) wherein its rear-sided surface portion 217" extends outwardly in the backward direction.

As shown in FIG. 39(*c*), it is preferred that the each protrusion 218" of the holder has its front end surface 219" extending perpendicular or approximately perpendicular to the pricking direction. As a result, once the each wing 426" moves forwardly to ride over the each protrusion 218" upon the assembling of the device, the wing 426" cannot backwardly ride over the protrusion 218" any more. In other words, the falling prevention wing 426" of the trigger part 400" in the pricking device before use of the device is positioned in front of the protrusion 218" of the holder 200" so that the trigger 400" cannot move backwardly with respect to the holder 200", which serves to effectively prevent the trigger part 400" from falling from or coming off the holder 200".

After the lancet pricking device of the type C is used, the re-use preventing wings 424" provided behind the falling prevention wings 426" have returned to its original shape after its deformation in the same manner as the above the riding of the wings 426". That is, the each wing 424" is located in front of the protrusion 218" of the inner side wall of the holder 200", after riding over the protrusion 218" upon the pricking operation. As a result, the trigger 400" cannot be backwardly moved with respect to the holder 200" at a point in time after the device is used. This means that the positional relationship between the holder 200" and the trigger part 400" after the pricking cannot be returned to its original state of pre-pricking. In this regard, the opened arms of the trigger part cannot be closed again, and thus the engaged portion 421" of the trigger part cannot be again in engagement with the engagement portion 131" of the lancet body. Accordingly, the used lancet body cannot be any more ready for pricking so that the device cannot be used for another pricking operation. The deformation of the wings 424" and 426" and the restoring thereof to their original shapes can be easily achieved by forming the trigger part 400" with resin (for example, resin such as polyethylene and polystyrene), and then making use of the elastic property of such resin. For this reason, these wings preferably have flexibility as a whole.

The trigger part 400" has a spring attachment portion 450". The spring attachment portion can suitably work for the assembling of the lancet pricking device. This is the same as those of the pricking devices of the types A and B. Turning to FIG. 22, in a case where the spring attachment portion 450" of the trigger part is comprised of a bent elongated part having a free end and a fixed end, the assembling of the lancet pricking device (in particular, attaching of the launching spring 300") is effectively facilitated. That is, as shown in FIG. 22, when the spring attachment portion 450" is provided in the form of a hook (e.g., fishing-needle form or U-like form), the inward warping of the spring attachment portion 450" can be easily performed (see FIGS. 22(*a*) and 22(*b*)), so that the engagement of the launching spring coil with the attachment portion of the trigger part can be effectively facilitated. It is preferred that the spring attachment portion 450" has a protrusion 450a" that protrudes outwardly. In particular, a first protrusion $450a_1"$ is preferably provided at the free end of the bent elongated part, whereas a second protrusion $450a_2"$ is preferably provided at the fixed end of the bent elongated part as shown in FIG. 22(*a*). In this case, once the spring 300" increases its coil diameter to ride over the protrusions 450a", then the spring 300" is returned to have its original coil diameter. As a result, a joint between the spring 300" and the spring attachment portion 450" cannot be easily released any longer (see FIGS. 22(*a*) to 22(*c*)).

(Launching Spring)

Similarly to the launching springs of the types A and B, the launching spring 300" is used for shooting, firing or launching the lancet (more specifically, the lancet body with the tip of the pricking needle exposed therefrom). In other words, the launching spring 300" is a spring (for example, a coil spring) that gives an impellent force for launching the pricking needle 150", i.e., the lancet body including the exposed pricking needle, or a driving force for pricking.

(Pushing Prevention Mechanism of Trigger Part)

Now, a pushing prevention mechanism regarding the trigger part of the lancet pricking device of the type C will be described. Similarly to those of the types A and B, the lancet pricking device of the type C has such a mechanism that the parts other than the holding portion of the lancet cap serve to prevent the pushing of the trigger part due to the interaction of such parts with the holder. Especially as for the lancet pricking device of the type C, the trigger part 400" comprises a flexible portion (or flexible part) 490" at a lateral face 430" of the main body thereof, as shown in FIGS. 40 and 41 (particularly, FIG. 40(*b*)). The flexible portion 490" can cooperates with the holder and the cap portion other than the holding portion of the lancet cap.

As shown in FIGS. 40 and 41, it is preferred that the flexible portion 490" is formed integrally with the lateral wall of the trigger part (and thus, the flexible portion may be integrally molded with the trigger part). It is also preferred that the flexible portion comprises an elongated part with its frond side serving as a free end and its rear side serving as a fixed end. As shown in FIGS. 40 and 41, the flexible portion 490" is provided to be substantially flush with a flat surface of the lateral wall of the trigger part, and however at least a part of the flexible portion 490" (particularly, the free end of the flexible portion) preferably slightly protrudes outward beyond the lateral wall surface (see, especially, FIG. 41(*c*)). The expression "flexible" regarding the flexible portion 490" means an embodiment in which the portion 490" is capable of being displaced inwardly (that is, toward the inner side of the trigger part), more specifically the free end of the portion 490" is capable of moving inwardly.

As shown in FIG. 45(a), at a point time before the lancet cap 170" is removed from the lancet, the flexible portion 490" of the trigger part is positioned between the main body 172" of the lancet cap (i.e., a part enclosing the tip 150a" of the pricking needle) and a wall portion 290" of the holder. As shown in FIG. 45(a), it is preferred that the flexible portion 490" of the trigger part is positioned to be housed in a concave portion 295" provided at the wall portion 290" of the holder (also, see FIG. 39(b) for understanding the concave portion 295"). The flexible portion 490" and the concave portion 295" preferably have shapes substantially complementary to each other as a whole. Thus, the flexible portion 490' preferably has an elongated form, and whereas the concave portion 295" has a groove form.

When the trigger part is intended to be pushed into the holder by the pressing force from the outside (that is, even when the trigger part is intended to be pushed so as to move forwardly with respect to the holder) at a point in time before the lancet cap 170" is removed from the lancet, the flexible portion 490" of the trigger part 170" abuts against both the main body 172" of the lancet cap and the wall portion 290" of the holder. As a result, such pushing of the trigger part into the holder is prevented before the removal of the lancet cap. More specifically, even when the trigger part is intended to be pushed forwardly into the holder by the pressing force from the outside, the flexible portion 490" of the trigger part abuts against both a side wall surface 172a" of the main body 172" of the lancet cap and a wall surface 295a" of the groove-like concave portion 295" of the wall 290" of the holder. See FIG. 45(a). In this regard, the flexible portion 490" is held while being sandwiched between the side wall surface 172a" of the main body 172" of the cap and the wall surface 295a" of the groove-like concave portion 295", and thereby the pushing of the trigger part 400" into the holder is prevented. This means that, when the lancet cap is still attached to the lancet, the securing/engagement of the lancet body cannot be released, and thereby the launching of the pricking needle is prevented before the removal of the lancet cap. While on the other hand, after the lancet cap is removed as shown in FIG. 45(b), there is generated a movement space for the flexible portion 490" of the trigger part. As a result, the trigger part can be pushed into the holder by the pressing force from the outside. When the trigger part is pushed forwardly with respect to the holder due to no existence of the lancet cap, the flexible portion 490" is caused to warp (such warping is caused by a counteraction from the groove wall surface, attributed to the pressed flexible portion 490"), while sliding on a front sloped portion 295b" of the groove-like concave portion 295" or while moving on the front sloped portion 295b" under friction against the portion 295b". As a result, the flexible portion 490" can move forwardly so that the pushing of the trigger part into the holder is suitably performed (see FIG. 45(b)). Such forward moving of the trigger part causes the securing or locking of the engagement portions 131" of the lancet body 130" to the engaged portions 421" of the arms 420" of the trigger part 400" to be released, and thereby the pricking needle 150" can be launched (see FIG. 45(c)).

Now, the pricking procedure for pricking the region of interest using the pricking device 500" of the type C will be described with reference to the top views of FIGS. 46(a) to 46(e) and the perspective views of FIGS. 47(a) to 47(e).

Figure 46:
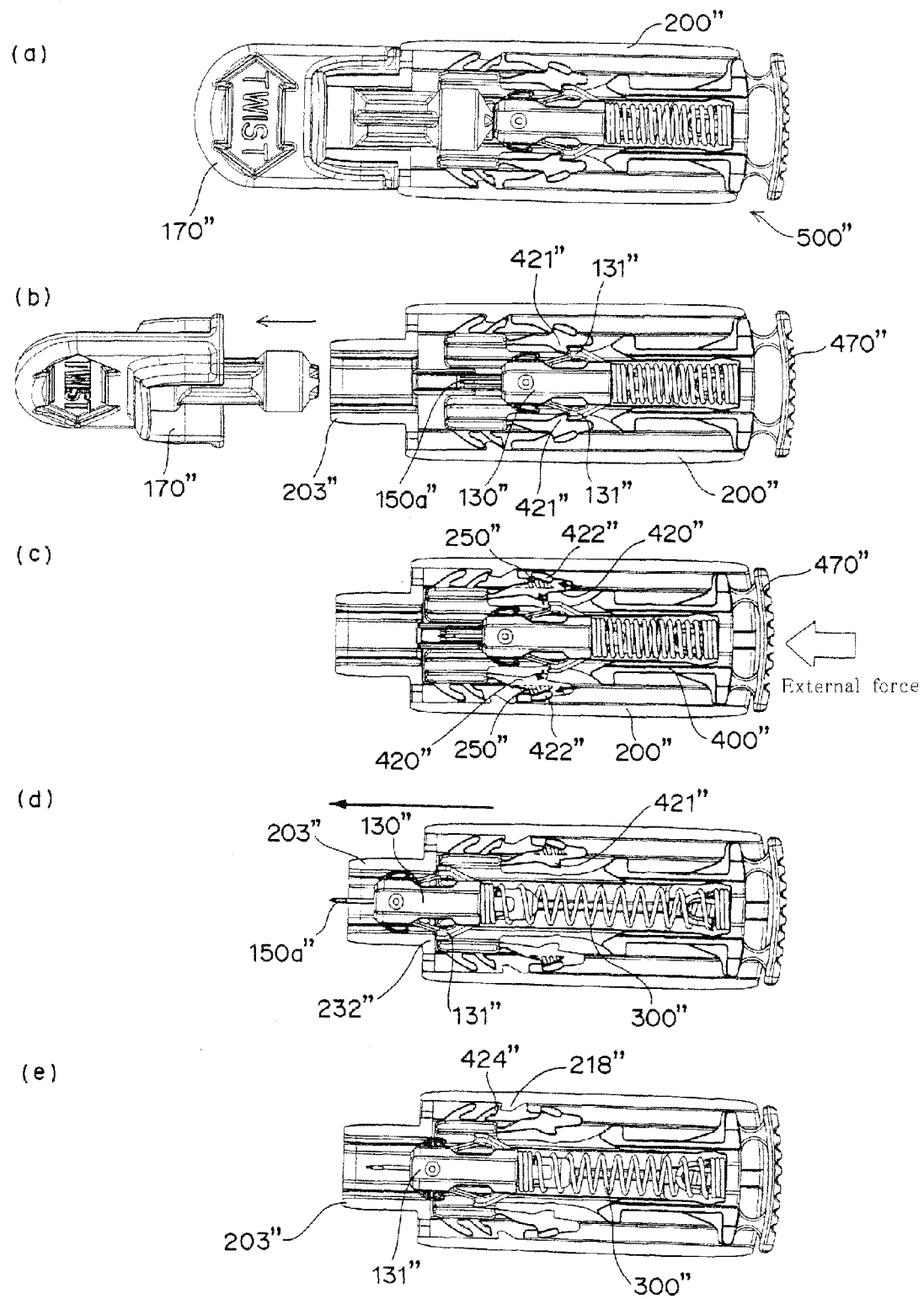
FIGS. 46(a) to 46(e) are top views schematically showing the changes in a lancet pricking device of Type C over time in its use.
Figure 47:
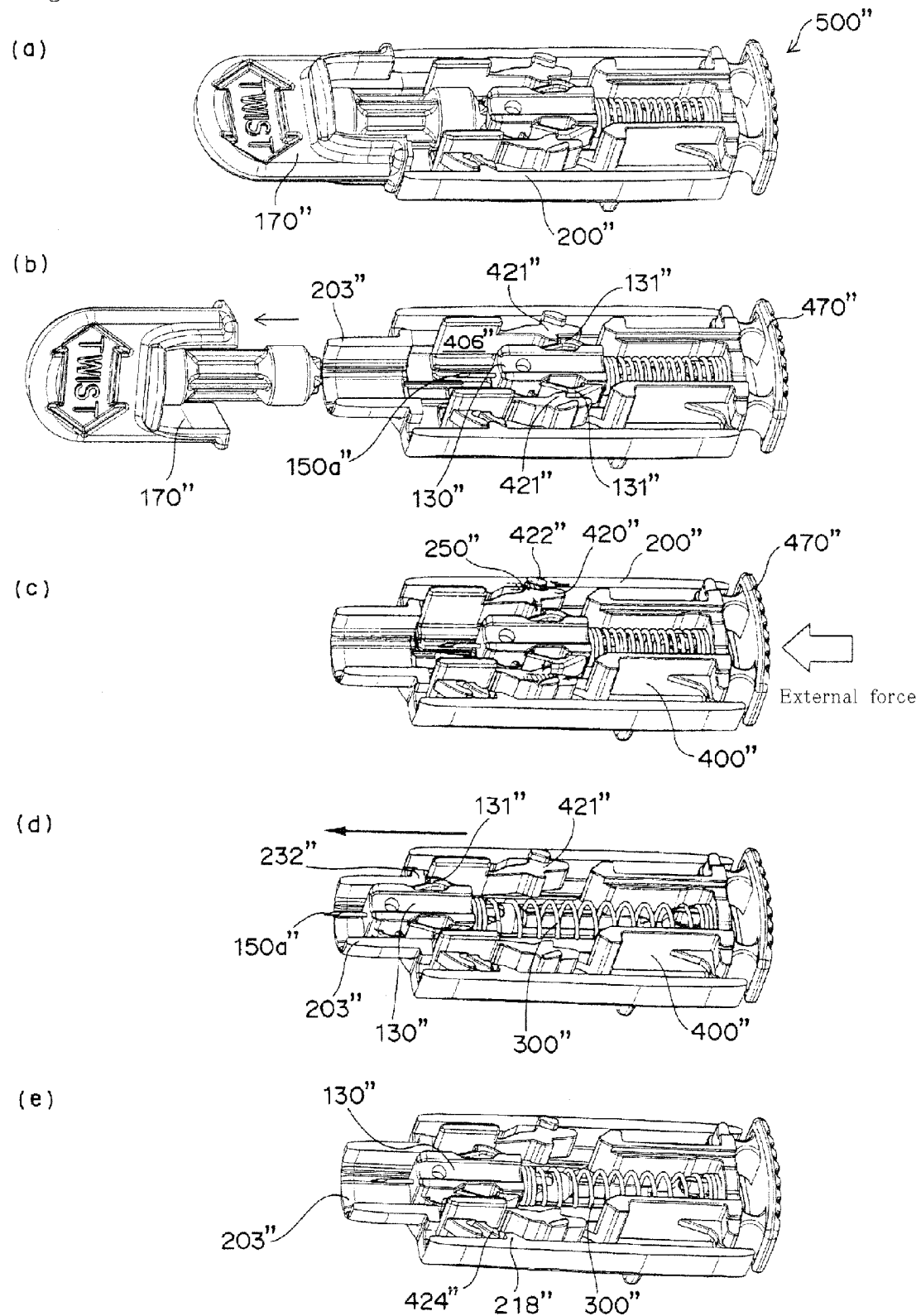
FIGS. 47(a) to 47(e) are perspective views schematically showing the changes in a lancet pricking device of Type C over time in use.

First, while the holder 200" of the lancet pricking device 500" of the type C shown in FIGS. 46(a) and 47(a) is held, the lancet cap 170" is twisted to break the "weakened part" of the lancet. During the twisting of the cap, as indicated by the arrows shown in FIGS. 46(b) and 47(b), the lancet cap 170" is forced to be spaced apart from the lancet body so that the tip 150a" of the pricking needle is exposed and thus it extends forwardly from the lancet body. In the state shown in FIGS. 46(b) and 47(b), the lancet body 130" with the tip 150a" of the pricking needle protruding therefrom is surely held within the space 406" of the trigger part 400" by the abutment relationship between the engagement portion 131" and the engaged portion 421".

Next, in the lancet pricking device 500" shown in FIGS. 46(b) and 47(b), the protruding pricking opening portion of the device, i.e., the front opening end 203" of the holder is applied to a region of interest to be pricked.

Thereafter, as shown in FIGS. 46(c) and 47(c), the external force is applied forwardly to the pressing portion 470" provided at the rear end of the trigger part. That is, the force for forwardly moving the trigger part 400" with respect to the holder 200" is applied.

During the forward moving of the trigger part 400" with respect to the holder 200", the sliding portion 422" of the each arm 420" moves forwardly on the sloped portion 250" provided in the each lateral inner wall of the holder 200". The sloped portion 250" has the sloped surface which is inclined closer to the inner lateral wall of the holder in the direction of front thereof. Accordingly, upon the forward moving of the trigger part 400", the sliding portion 422" moves not only forwardly but also outwardly (specifically, the sliding portion 422" moves forwardly and obliquely toward the outside). In this regard, the sliding portion 422" corresponds to a part of the each arm 420" of the trigger part, and thus the each arm 420" also moves outwardly as a whole, together with the sliding portion 422". That is, the outward expansion of the arms 420" is automatically performed during the pushing of the trigger part 420".

When the arms 420" are expanded outwardly, the engaged portions 421" of the trigger part also move outwardly. As a result, the abutment relationship between the engaged portions 421" of the trigger part and the engagement portion 131" of the lancet body cannot be maintained any longer. That is, the engagement between the engaged portions 421" and the engagement portion 131" ceases. When such engagement ceases, there is no means for preventing the forward movement of the lancet body 130", such forward movement being due to the compressed launching spring 300". Thus, the forward moving of the lancet body 130" with the tip of the needle exposed is instantly performed (see FIGS. 46(d) and 47(d)).

The launching spring 300" is instantly expanded from the compressed state thereof. Thus, the launching spring 300" becomes longer than its original size (i.e., longer than the state where it does not substantially receive the force). The expansion of the spring 300" causes at least one part of the tip 150a" of the pricking needle to protrude beyond the front opening end 203" of the holder. The front opening end 203" of the holder is in contact with the region of interest to be prickled, and thus the region of interest is prickled by the protruding tip of the needle. A part of the lancet body (e.g., engagement portion 131" in the embodiment shown in the drawings) collides with the inner wall surface 232" of the holder (the front opening end 203" of the holder 200" being defined by such inner wall surface 232") to thereby restrict the forward movement of the lancet body 130" (see FIGS. 46(d) and 47(d)).

In the state shown in FIG. 46(d) and FIG. 47(d), the launching spring 300" has been expanded longer than its original length as described above. Directly after the forward movement of the lancet body is achieved, the lancet body starts to move backward by the counteracting force attributed to the inner wall surface 232". The launching spring 300" is finally returned to its original shape. FIG. 46(e) and FIG. 47(e) show the state in which the launching spring has been returned to its original shape.

During the forward movement of the trigger part 400" with respect to the holder 200" upon the pushing of the trigger part 400", the re-use preventing wings 424" of the trigger part move forwardly so that they ride over the corresponding protrusions 218" provided at the lateral inner walls of the holder 200". Accordingly, in the state shown in FIG. 46(e) and FIG. 47(e), even when the trigger part 400" is intended to backwardly move with respect to the holder 200", the re-use preventing wings 424" abut against the protrusions 218", so that the trigger part cannot be backwardly moved any more.

Thus, once the state shown in FIGS. 46(e) and 47(e) is obtained, the positional relationship of the trigger part 400" with respect to the holder 200" cannot be substantially changed. This means that, even when the lancet body 130" is intended to be backwardly moved, the arms of the trigger part remain expanded, so that the abutment relationship between the engaged portion 421" of the trigger part and the engagement portion 131" of the lancet body cannot be provided again. As a result, the lancet body with the tip of the used pricking needle exposed therefrom cannot be reused for pricking. The used pricking needle cannot be reused, which is very desirable from the viewpoint of hygiene and safety. In light of the device embodiment with such re-use preventing mechanism, the lancet pricking device of the type C can be referred to as the "single use device", similarly to the lancet pricking devices of the types A and B.

Although a few embodiments of the present invention have been hereinbefore described, such embodiments are only for illustrative purpose regarding the typical examples, and thus the present invention is not limited to these embodiments. It will be readily appreciated by those skilled in the art that various modifications are possible without departing from the scope of the invention. For example, the following modified embodiments are possible.

Figure 48:
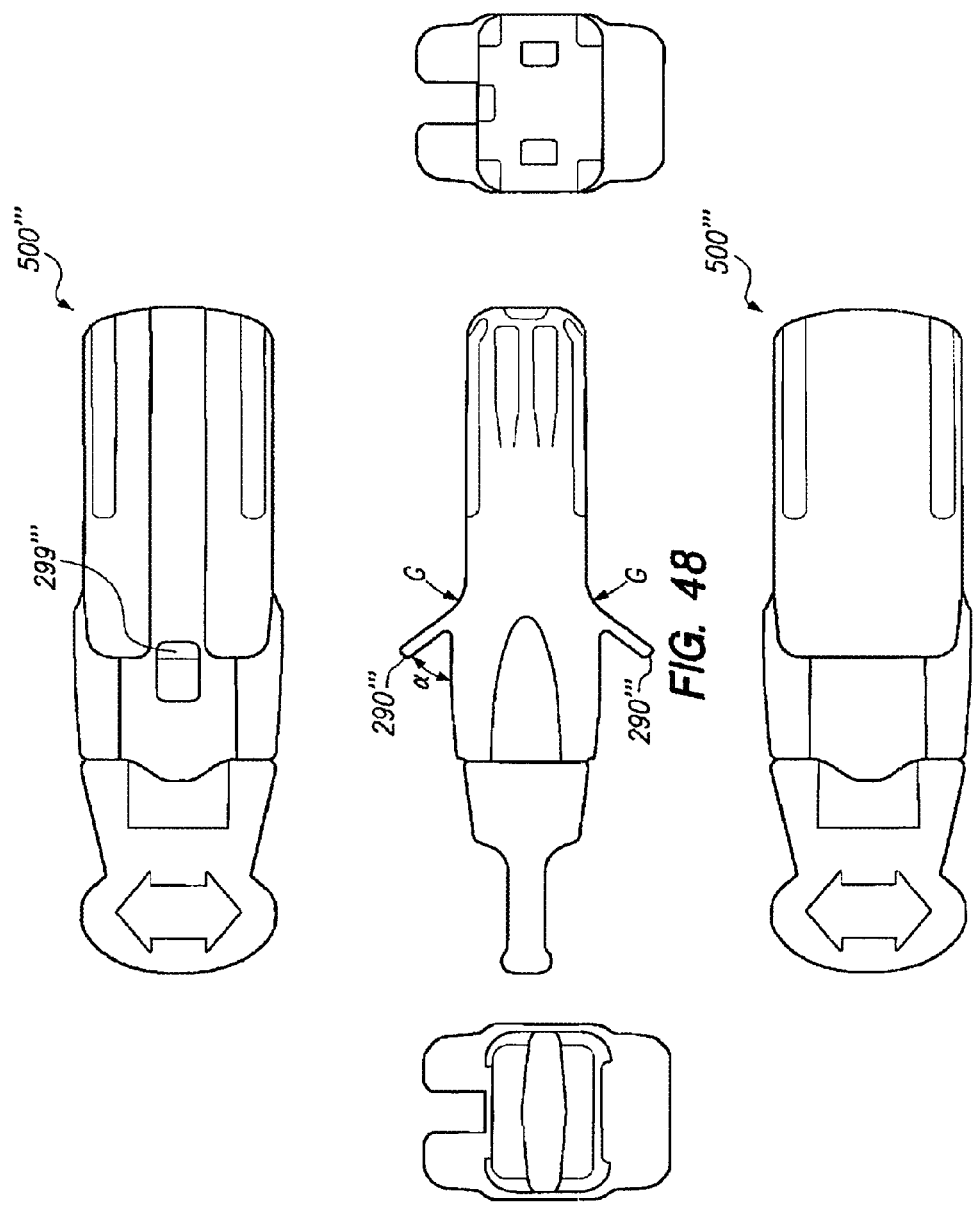
FIG. 48 are a top view, a side view, a bottom view and an end-surface view schematically showing an example of a modified appearance of a lancet pricking device of the present invention.
Figure 49:
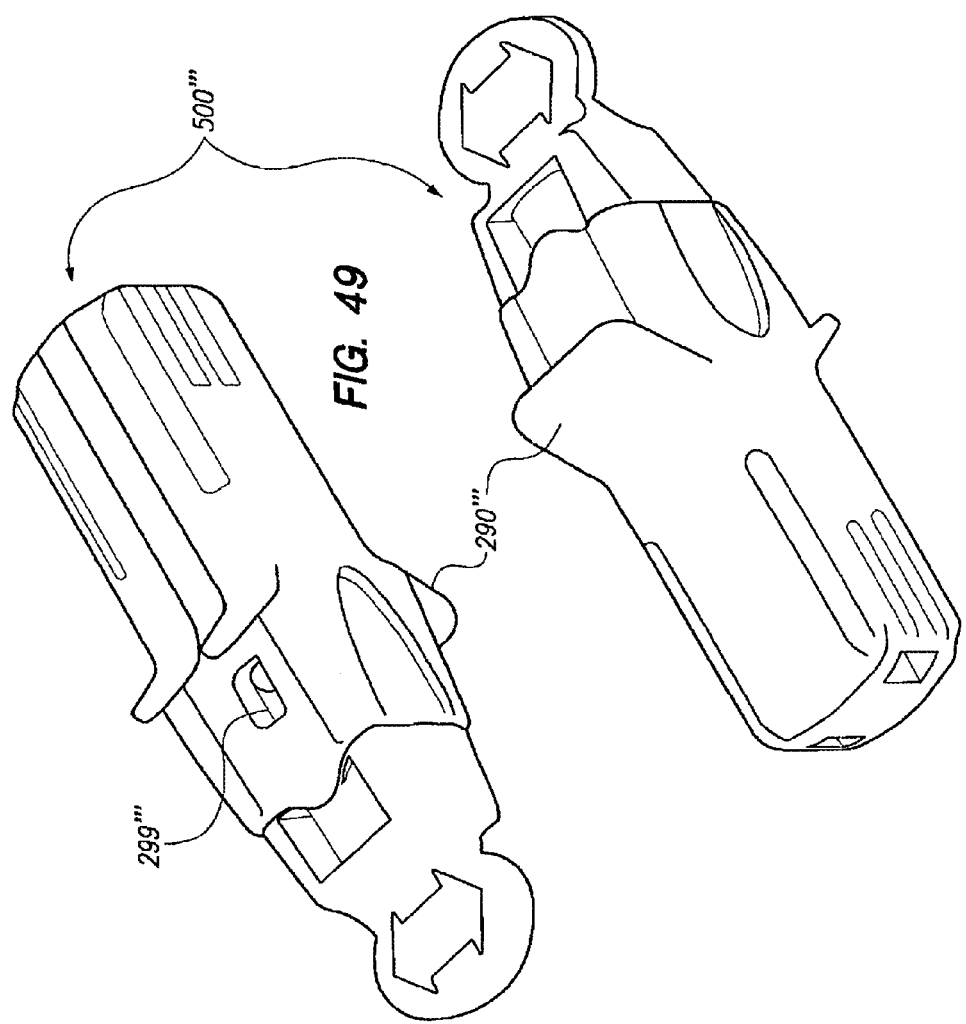
FIG. 49 is a perspective view of the lancet pricking device of FIG. 48.
Figure 50:
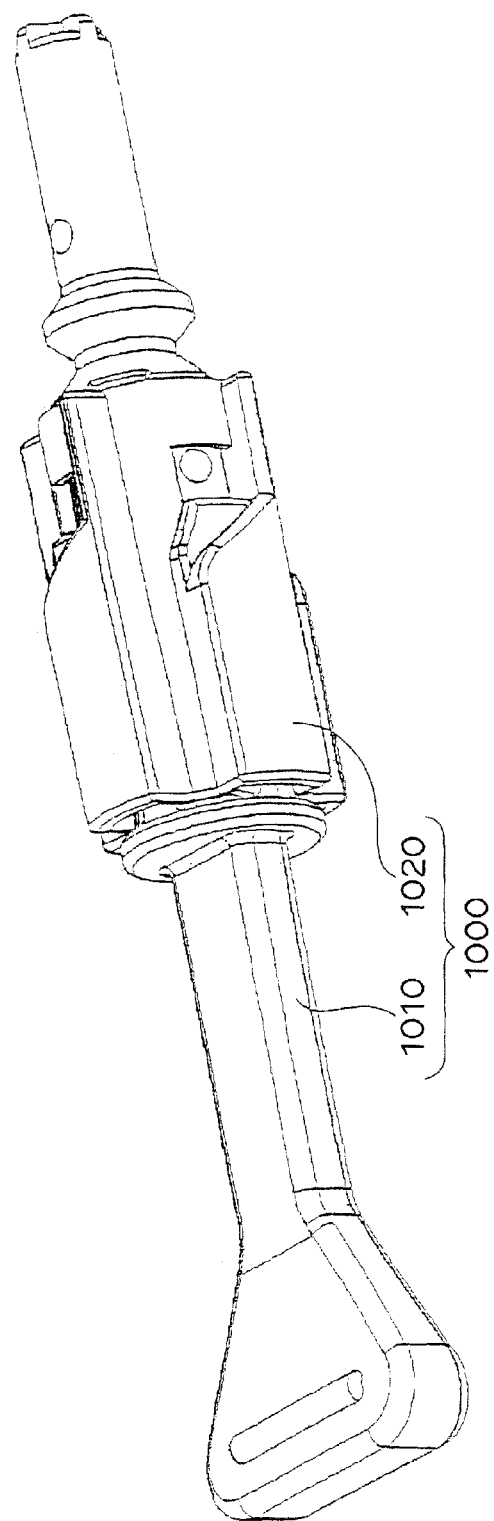
FIG. 50 is a perspective view showing an appearance of a lancet assembly.
Figure 51:
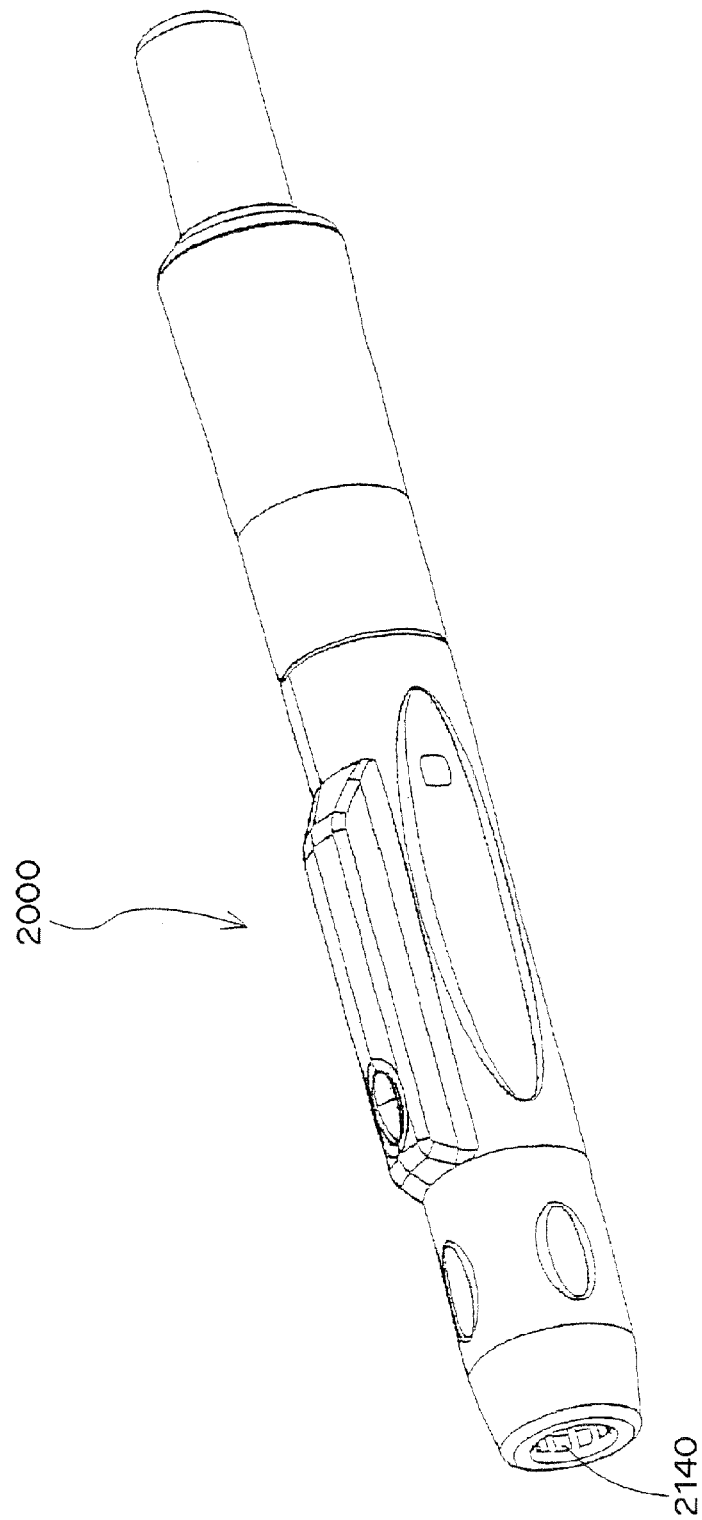
FIG. 51 is a perspective view showing an appearance of an injector.
Figure 52:
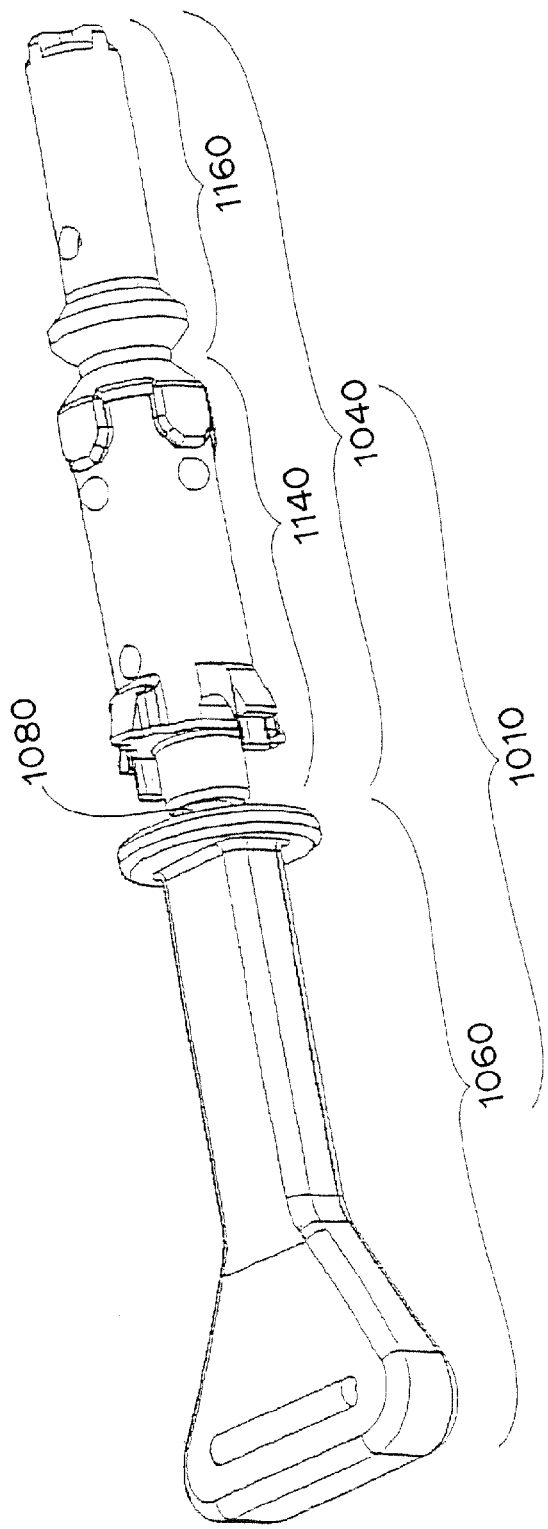
FIG. 52 is a perspective view showing an appearance of a lancet.
Figure 53:
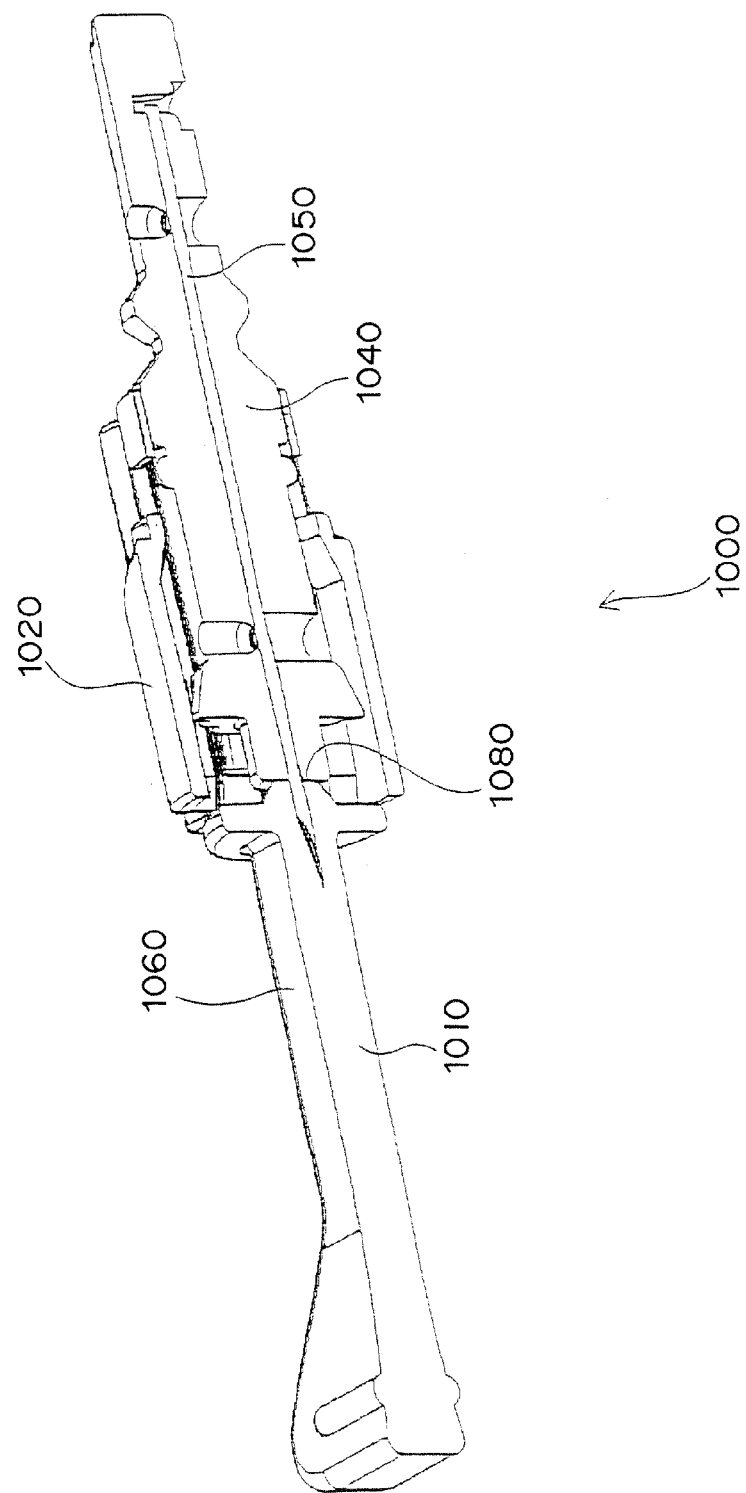
FIG. 53 is a perspective view showing a lancet of FIG. 50, cut away in half so as to make it easy to understand the inside of the lancet.
Figure 54:
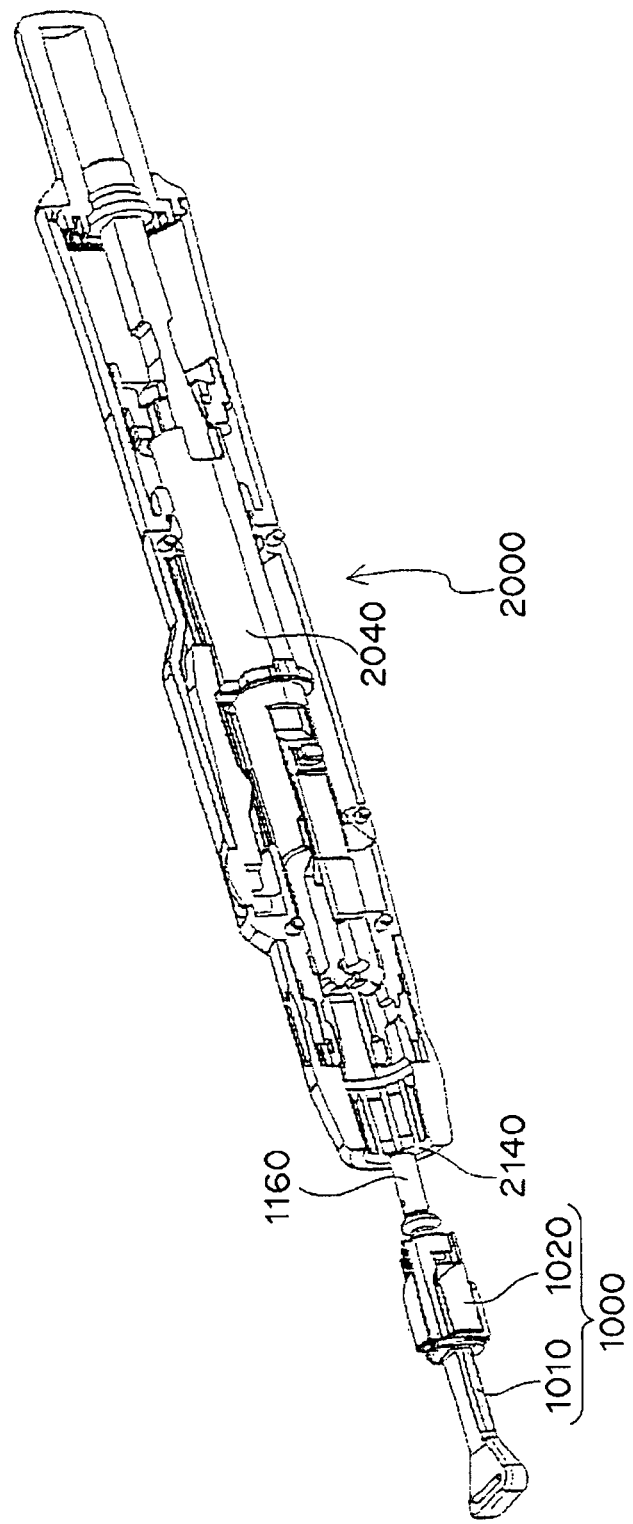
FIG. 54 is a perspective view showing the state before a lancet assembly is loaded into an injector.
Figure 55:
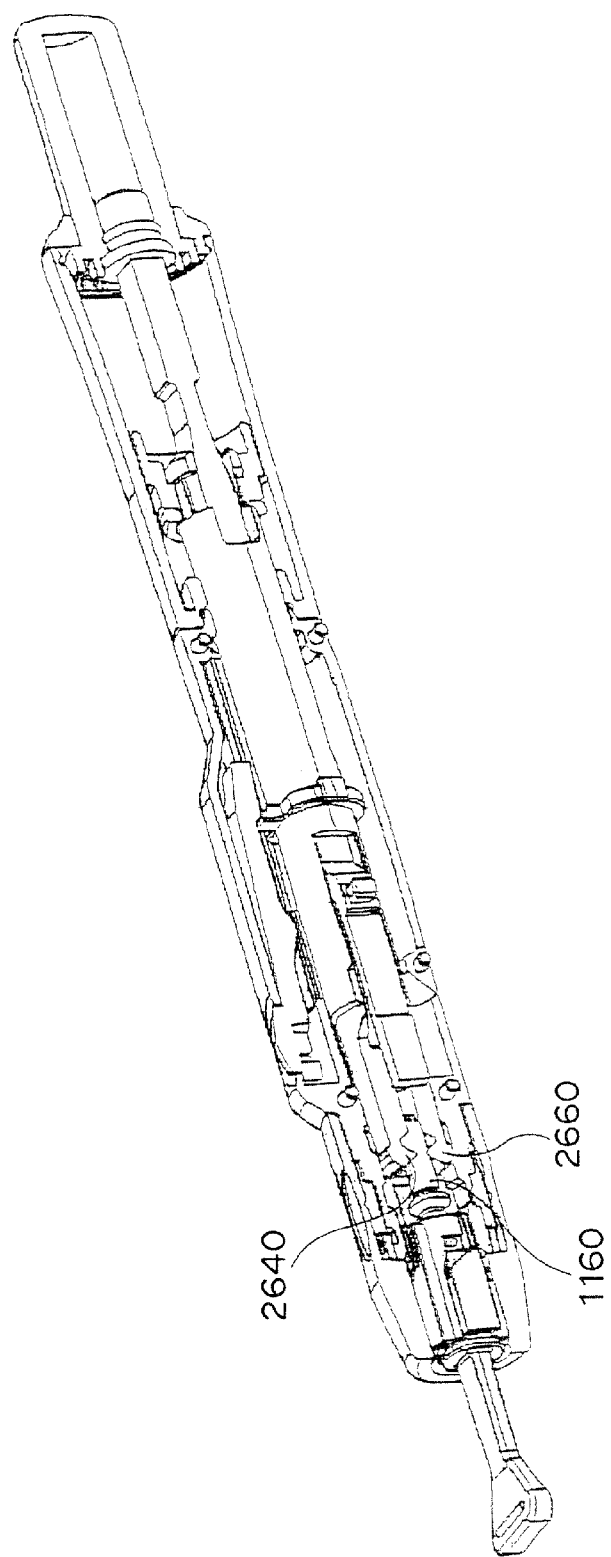
FIG. 55 is a perspective view showing the state in which a lancet is held by the tip of a plunger upon loading a lancet assembly.
Figure 56:
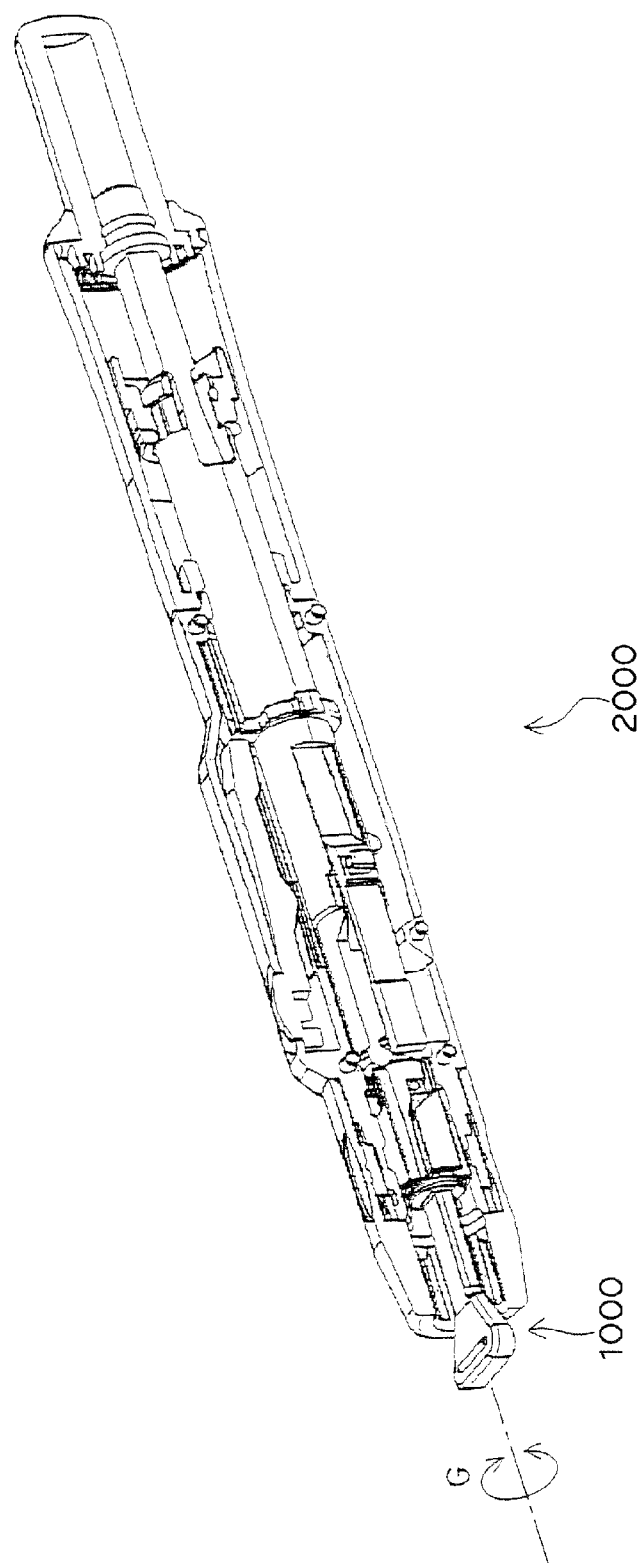
FIG. 56 is a perspective view showing the state of completion of loading a lancet assembly wherein a plunger cannot be retracted any more.
Figure 57:
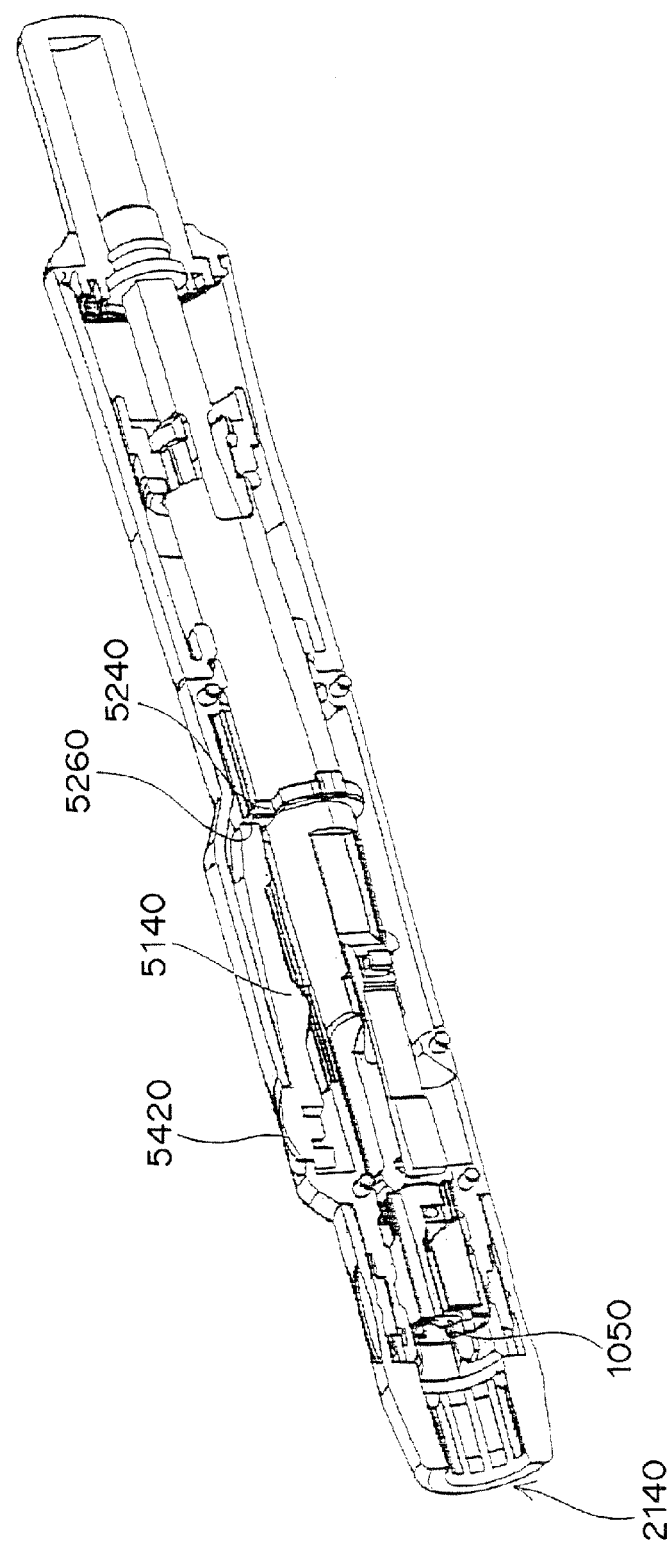
FIG. 57 is a perspective view sowing the state in which a lancet cap has been removed and thus a lancet is ready for pricking.

- In the accompanying drawings, the pricking needle (150, 150', 150") has a "needle form" whose uppermost is wholly sharpened, but is not necessarily limited thereto. For example, the pricking needle (150, 150', 150") may have a "blade form" having one side face of its tip sharpened.
- The appearance of the lancet pricking device of the present invention is not limited to those of the types A, B, and C, and thus the device of the present invention can be embodied with various appearances. For example, the lancet pricking devices of the invention may have the appearance as shown in FIGS. 48 and 49. In the device appearance shown in FIGS. 48 and 49, flange-like or brim-like protrusions 290''' are provided at the outer surface of the holder. The flange-like or brim-like protrusion 290''' serves to provide an appropriate gripping power when the pricking is performed through the "stamping" operation, which is especially true for the pricking device of the type B or the like. That is, when "G" portions shown in FIG. 48 are gripped with the fingers via the protrusions 290''', the holder can be surely held without causing the fingers to slip over the outer surface of the holder. As a result, the effective pushing of the pricking device against the predetermined region to be pricked can be performed. Such flange-like or brim-like protrusion 290''' also serves as a grip positioning effect that allows the fingers of the user to be guided to an appropriate position when the holder is held by the user. That is, even when the holder is held only according to a tactile sensing of the fingers to the holder, the contact between the brim-like protrusions 290''' and the fingers can make the user to indirectly understand a local position of the holder to be gripped.

Such flange-like or brim-like protrusion 290''' may be integrally molded with the holder (especially, integrally molded with the wall portion of the holder), and thus may be formed of the same resin as the raw material of the holder. According to the invention, the flange-like or brim-like protrusion 290''' is provided from the viewpoint of ergonomics. For instance, a protruding angle α of the protrusion 290''' (see FIG. 48) is preferably in the range of 10° to 90°, and more preferably in the range of 30° to 60° and for example about 45°. Also from the ergonomic viewpoint, the protrusions 290''' are provided at the front-sided outer surface of the holder. For example, the protrusions 290''' are located apart from the pricking opening end by about 10 mm to about 20 mm (for example, apart from the opening end by about 15 mm). Moreover, in order to allow the finger to suitably fit the rear side of the protrusion 290''', the protrusion 290''' or the rear side thereof may have an arc-like shape (or so-called "R" shape). For example, the protrusion 290''' or the rear side thereof may have the arc-like shape such as "50R" and "20R".

As shown in FIGS. 48 and 49, a window (window opening) 299''' through which the inside of the holder can be observed from the outside may be provided in the wall of the holder. Particularly, when the window (window opening) 299''' is provided in the shown position of the holder wall, the pricking needle of the lancet can be observed after the removal of the lancet cap. That is, in the device before the pricking operation or before the launching of the pricking needle, the pricking needle can be observed from the outside through the window (window opening) 299'''. In contrast, in the device after the pricking operation or after the launching of the pricking needle, the lancet body is positioned as a whole at the more front side of the device due to the expansion of the launching spring (i.e., due to the uncompressed state of the launching spring), so that the lancet body can be observed from the outside through the window (window opening) 299'''. It is therefore easy for the user to determine whether the present state is "before pricking" or "after pricking" by the observation of "pricking needle" or "lancet body" through the window 299'''.

Industrial Applicability

The lancet pricking device according to the present invention is compact in size and has a superior advantage in not only its operability but also its hygiene and safety. Accordingly, the lance pricking device of the present invention can be not only used to take blood from a patient with diabetes, but also suitably used for various other applications where the blood sampling is needed.

CROSS REFERENCE TO RELATED PATENT APPLICATION

The present application claims the right of priorities of Japan patent application No. 2009-233428 (filing date: Oct. 7, 2009, title of the invention: LANCET PRICKING DEVICE) and Japan patent application No. 2009-241385 (filing date: Oct. 20, 2009, title of the invention: PRICKING DEVICE), the whole contents of which are incorporated herein by reference.

The invention claimed is:
1. A lancet pricking device, comprising:
a lancet;
a launching spring;
a trigger part; and a holder for housing therein the lancet, the launching spring and the trigger part, wherein the lancet comprises a lancet body, a lancet cap and a pricking needle, and the pricking needle is disposed in both the lancet body and the lancet cap;

wherein the trigger part comprises a pair of arms positioned inside the holder;

wherein the launching spring is attached to the lancet body, and the lancet body is secured to the arms of the trigger part by an abutment of the lancet body on the arms such that the launching spring is kept compressed before a pricking operation;

wherein the trigger part cannot be pushed further into the holder at a point in time before the lancet cap is removed from the lancet, and whereas the trigger part can be pushed further into the holder at a point in time after the lancet cap is removed from the lancet;

wherein the arms of the trigger part become capable of warping upon the pushing of the trigger part to cause the secured lancet body to be released;

wherein the trigger part is disposed as a whole inside the holder such that only a pressing portion provided at a rear end of the trigger part protrudes outwardly from a rear opening end of the holder;

a front portion of the lancet cap protrudes outwardly from a front opening end of the holder, and a pair of parts provided at lateral sides of the front portion of the lancet cap is adjacent to a front end of the holder, or another part of the front portion of the lancet cap is adjacent to the front opening end of the holder such that a backward movement of the lancet with respect to the holder is prevented;

each of the arms of the trigger part has a front side serving as a fixed end and a rear side serving as a free end in which lateral sides of the lancet body are secured by abutting on the arms of the trigger part such that the launching spring is kept compressed before a pricking operation;

when the trigger part is forced to move forwardly with respect to the holder upon the pushing of the trigger part, each arm of the trigger part is expanded outwardly to cause the securing of each lateral side of the lancet body to each arm to be released;

wherein the trigger part comprises a flexible portion at a lateral face of a main body thereof; and at a point in time before the lancet cap is removed from the lancet, the flexible portion of the trigger part is positioned between a main body of the lancet cap and a wall of the holder.

2. The lancet pricking device according to claim 1, wherein the lancet cap comprises a holding portion in a front end thereof; and a lancet cap's portion other than the holding portion serves to prevent the pushing of the trigger part due to an interaction of the lancet cap's portion with the holder at a point in time before the lancet cap is removed from the lancet.

3. The lancet pricking device according to claim 1, wherein the lancet body and the pricking needle of the lancet and the launching spring are positioned inside the trigger part such that all of them do not protrude beyond the trigger part.

4. The lancet pricking device according to claim 1, wherein the launching spring is attached to a spring-attachment portion provided at a rear-sided inner wall of the trigger part; and the spring-attachment portion has a bent form of an elongated part with a free end and a fixed end.

5. The lancet pricking device according to claim 1, wherein, when the trigger part is forced to move forwardly with respect to the holder, the free end of the each arm of the trigger part slides on a sloped portion provided at a front-sided inner wall of the holder, and thereby the outward expansion of the each arm is automatically performed.

6. The lancet pricking device according to claim 1, wherein, at a point in time after the lancet cap is removed from the lancet, an external force applied to the pressing portion provided at the rear end of the trigger part serves to push the trigger part into the holder such that the trigger part moves forwardly with respect to the holder.

7. The lancet pricking device according to claim 1, wherein, at a point in time before the lancet cap is removed from the lancet, the flexible portion of the trigger part is positioned such that it is housed in a concave portion provided in the wall of the holder.

8. The lancet pricking device according to claim 1, wherein, at a point in time before the lancet cap is removed from the lancet, even when the trigger part is intended to be pushed into the holder due to a pressing force from the outside, the flexible portion of the trigger part abuts against both the main body of the lancet cap and the wall of the holder, whereby the pushing of the trigger part is prevented; and at a point in time after the lancet cap is removed from the lancet, when the trigger part is pushed into the holder by the pressing force from the outside, the flexible portion is caused to warp to perform the pushing of the trigger part.

9. The lancet pricking device according to claim 1, wherein a re-use preventing wing is provided at a front-sided outer face of the trigger part such that it extends backwardly and obliquely, and whereas a re-use preventing protrusion is provided at an inner wall of the holder;

upon the pushing of the trigger part in the pricking operation, the re-use preventing wing of the trigger part moves forwardly while contacting on the re-use preventing protrusion of the holder until the wing rides over the protrusion; and after the pricking operation, the re-use preventing wing is capable of abutting against the re-use preventing protrusion such that a backward movement of the trigger part is restricted, and thereby the trigger part after the pricking cannot be returned to its pre-pricking state.

10. A lancet pricking device, comprising:

a lancet;

a launching spring;

a trigger part; and a holder for housing therein the lancet, the launching spring and the trigger part, wherein the lancet comprises a lancet body, a lancet cap and a pricking needle, and the pricking needle is disposed in both the lancet body and the lancet cap;

wherein the trigger part comprises a pair of arms positioned inside the holder;

wherein the launching spring is attached to the lancet body, and the lancet body is secured to the arms of the trigger part by an abutment of the lancet body on the arms such that the launching spring is kept compressed before a pricking operation;

wherein the trigger part cannot be pushed further into the holder at a point in time before the lancet cap is removed from the lancet, and whereas the trigger part can be pushed further into the holder at a point in time after the lancet cap is removed from the lancet;

wherein the arms of the trigger part become capable of warping upon the pushing of the trigger part to cause the secured lancet body to be released;

wherein the trigger part comprises a flexible portion at a lateral face of a main body thereof;

at a point in time before the lancet cap is removed from the lancet, the flexible portion of the trigger part is positioned between a main body of the lancet cap and a wall of the holder; and wherein the lancet body and the pricking needle of the lancet and the launching spring are positioned inside the trigger part such that all of them do not protrude beyond the trigger part.

11. A lancet pricking device, comprising:

a lancet;

a launching spring;

a trigger part; and a holder for housing therein the lancet, the launching spring and the trigger part, wherein the lancet comprises a lancet body, a lancet cap and a pricking needle, and the pricking needle is disposed in both the lancet body and the lancet cap;

wherein the trigger part comprises a pair of arms positioned inside the holder;

wherein the launching spring is attached to the lancet body, and the lancet body is secured to the arms of the trigger part by an abutment of the lancet body on the arms such that the launching spring is kept compressed before a pricking operation;

wherein the trigger part cannot be pushed further into the holder at a point in time before the lancet cap is removed from the lancet, and whereas the trigger part can be pushed further into the holder at a point in time after the lancet cap is removed from the lancet;

wherein the arms of the trigger part become capable of warping upon the pushing of the trigger part to cause the secured lancet body to be released;

wherein the trigger part comprises a flexible portion at a lateral face of a main body thereof;

at a point in time before the lancet cap is removed from the lancet, the flexible portion of the trigger part is positioned between a main body of the lancet cap and a wall of the holder;

wherein, at a point in time before the lancet cap is removed from the lancet, even when the trigger part is intended to be pushed into the holder due to a pressing force from the outside, the flexible portion of the trigger part abuts against both the main body of the lancet cap and the wall of the holder, whereby the pushing of the trigger part is prevented; and at a point in time after the lancet cap is removed from the lancet, when the trigger part is pushed into the holder by the pressing force from the outside, the flexible portion is caused to warp to perform the pushing of the trigger part.

\* \* \* \* \*